US011016040B2

(12) United States Patent
Yamakawa et al.

(10) Patent No.: US 11,016,040 B2
(45) Date of Patent: May 25, 2021

(54) APPARATUS AND METHOD OF PROCESSING DATA ACQUIRED IN X-RAY EXAMINATION, AND X-RAY EXAMINATION SYSTEM EQUIPPED WITH THE APPARATUS

(71) Applicant: JOB CORPORATION, Kanagawa (JP)

(72) Inventors: Tsutomu Yamakawa, Kanagawa (JP); Shuichiro Yamamoto, Kanagawa (JP); Masahiro Okada, Kanagawa (JP)

(73) Assignee: JOB CORPORATION, Kanagawa (JP)

( * ) Notice: Subject to any disclaimer, the term of this patent is extended or adjusted under 35 U.S.C. 154(b) by 46 days.

(21) Appl. No.: 16/313,208

(22) PCT Filed: May 16, 2018

(86) PCT No.: PCT/JP2018/018867
§ 371 (c)(1),
(2) Date: Dec. 26, 2018

(87) PCT Pub. No.: WO2018/212217
PCT Pub. Date: Nov. 22, 2018

(65) Prior Publication Data
US 2019/0162679 A1    May 30, 2019

(30) Foreign Application Priority Data

May 16, 2017    (JP) .............................. JP2017-097603

(51) Int. Cl.
*G01N 23/00*       (2006.01)
*G01N 23/044*      (2018.01)
(Continued)

(52) U.S. Cl.
CPC ............. *G01N 23/044* (2018.02); *A61B 6/12* (2013.01); *A61B 6/4241* (2013.01); *A61B 6/463* (2013.01);
(Continued)

(58) Field of Classification Search
CPC ......... A61B 6/12; A61B 6/4241; A61B 6/463; A61B 6/466; A61B 6/469; A61B 6/482;
(Continued)

(56) References Cited

U.S. PATENT DOCUMENTS

2007/0030944 A1    2/2007   Grasruck et al.
2007/0092127 A1    4/2007   Grasruck et al.
(Continued)

FOREIGN PATENT DOCUMENTS

EP         3 644 048        4/2020
JP        2013-119000       6/2013
(Continued)

OTHER PUBLICATIONS

H. Watabiki et al., "Development of Dual-Energy X-Ray Inspection System", Anritsu Technical No. 87, Mar. 2012.

*Primary Examiner* — Dani Fox
(74) *Attorney, Agent, or Firm* — Clark & Brody LP

(57) ABSTRACT

In a data processing apparatus, image data are calculated based on photon counts of an X-ray beam transmitted through an object. Based on the image data, X-ray attenuation information is calculated. The attenuation information includes i) inherent information inherently depending on a type or a property of the object, the inherent information being indicated by a quantity of a vector in an n-dimensional coordinate whose dimension is equal in number to the n-piece energy ranges; and ii) associated information being associated with the inherent information and depending on a length of a path along which the X-ray beam passes though the object. From the attenuation information, only the inherent information is produced which is independent of the associated information. Scattering points corresponding to the inherent information are calculated to be mapped in the (Continued)

n-dimensional coordinate or in a coordinate whose dimension is less than the n-dimensional coordinate.

21 Claims, 38 Drawing Sheets

(51) Int. Cl.
    *G01N 23/083*     (2018.01)
    *G01N 23/18*     (2018.01)
    *A61B 6/00*     (2006.01)
    *A61B 6/12*     (2006.01)
    *G01N 23/087*     (2018.01)

(52) U.S. Cl.
    CPC .............. *A61B 6/466* (2013.01); *A61B 6/469* (2013.01); *A61B 6/482* (2013.01); *A61B 6/483* (2013.01); *A61B 6/502* (2013.01); *A61B 6/5217* (2013.01); *A61B 6/5282* (2013.01); *G01N 23/083* (2013.01); *G01N 23/087* (2013.01); *G01N 23/18* (2013.01); *G01N 2223/402* (2013.01); *G01N 2223/423* (2013.01); *G01N 2223/652* (2013.01)

(58) Field of Classification Search
    CPC ....... A61B 6/483; A61B 6/502; A61B 6/5217; A61B 6/5282; G01N 2223/402; G01N 2223/423; G01N 2223/652; G01N 23/044; G01N 23/083; G01N 23/18; G01N 33/02
    See application file for complete search history.

(56) References Cited

U.S. PATENT DOCUMENTS

| | | | |
|---|---|---|---|
| 2010/0226474 A1 | 9/2010 | Yamakawa et al. | |
| 2016/0038112 A1 | 2/2016 | Wiemker et al. | |
| 2016/0266054 A1* | 9/2016 | Cao ........................ | A61B 6/032 |
| 2018/0209922 A1 | 7/2018 | Yamakawa et al. | |
| 2018/0214113 A1 | 8/2018 | Yamakawa et al. | |

FOREIGN PATENT DOCUMENTS

| | | |
|---|---|---|
| JP | 2016-145778 | 8/2016 |
| WO | 2007/110465 | 10/2007 |
| WO | 2014/126189 | 8/2014 |
| WO | 2014/181889 | 11/2014 |
| WO | 2015/111728 | 7/2015 |

* cited by examiner

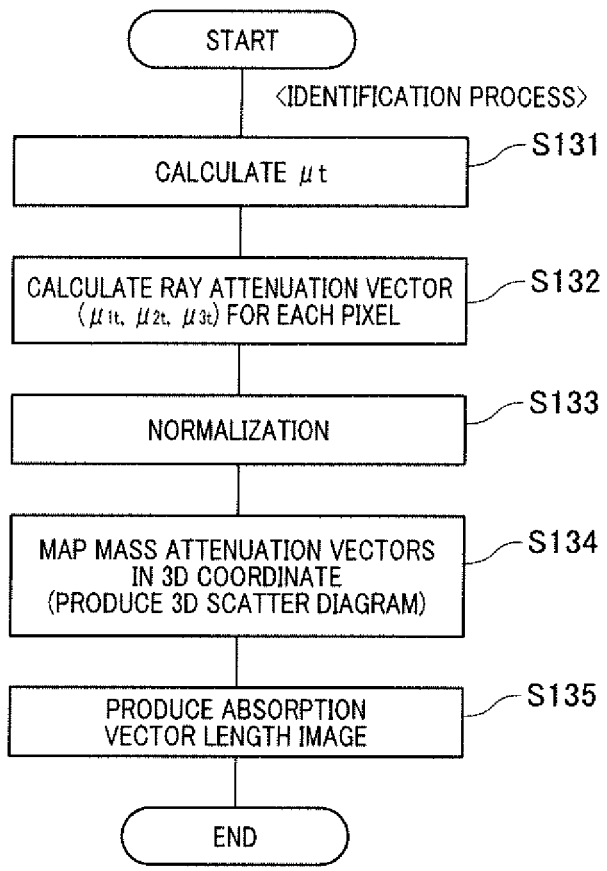
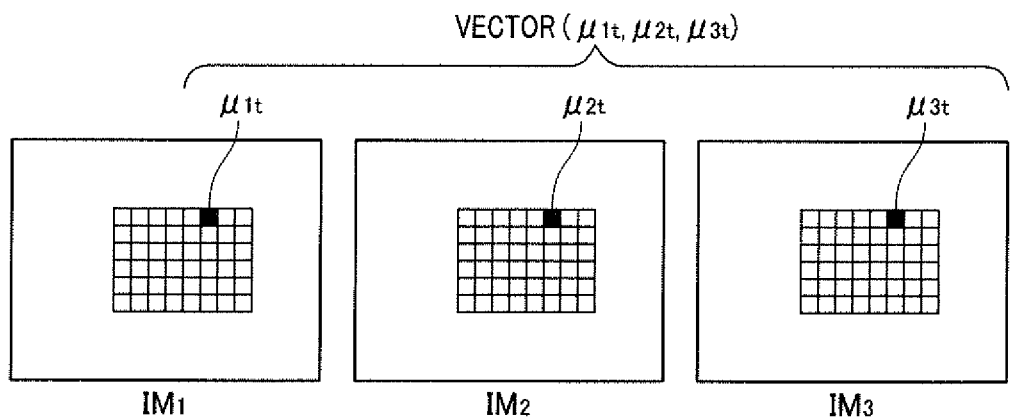

FIG.18
(A) 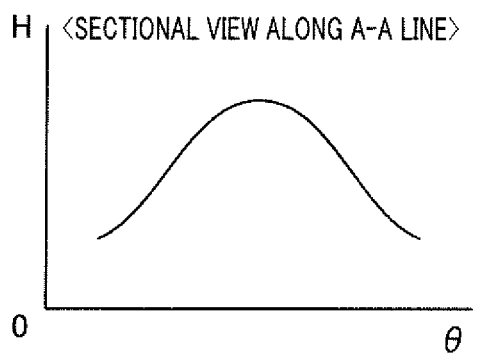
(B) 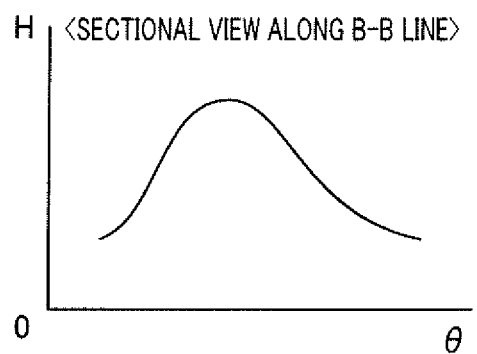
FIG.19
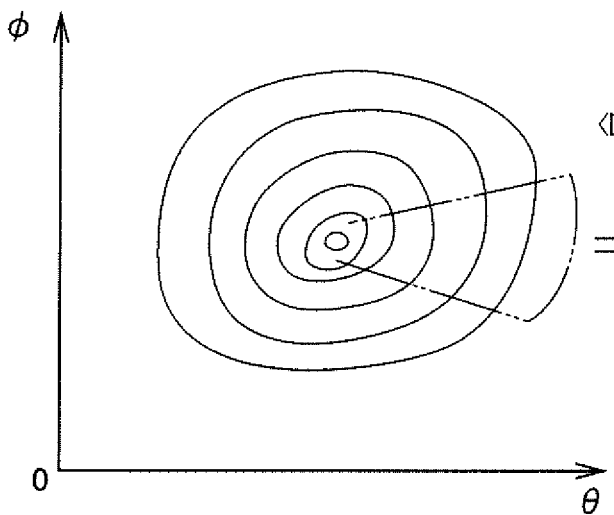
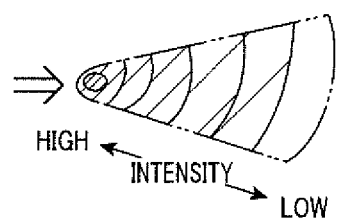

<SCATTER DIAGRAM OF ARGUMENT DATA: Fhen>

<CONTOUR LINE IMAGE: Fto>

FIG.36
<REFERENCE DATA FOR GRAVITY CENTER PATTERNS: PTGref>
(A)
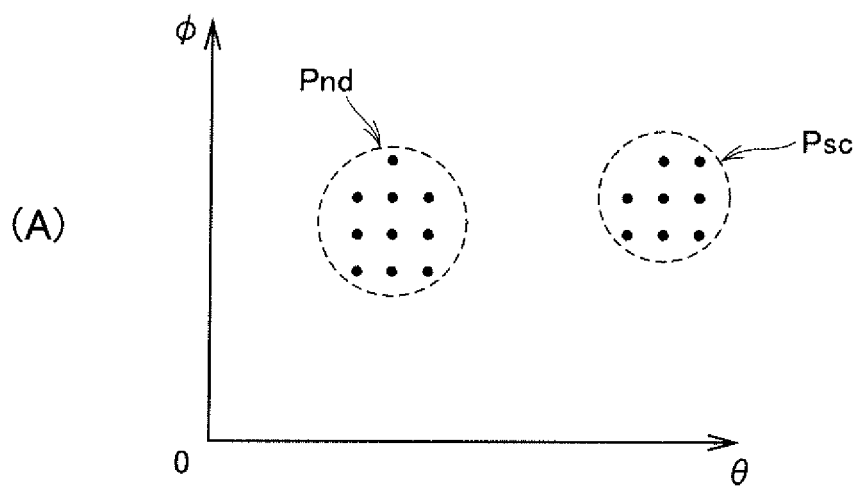
(B)
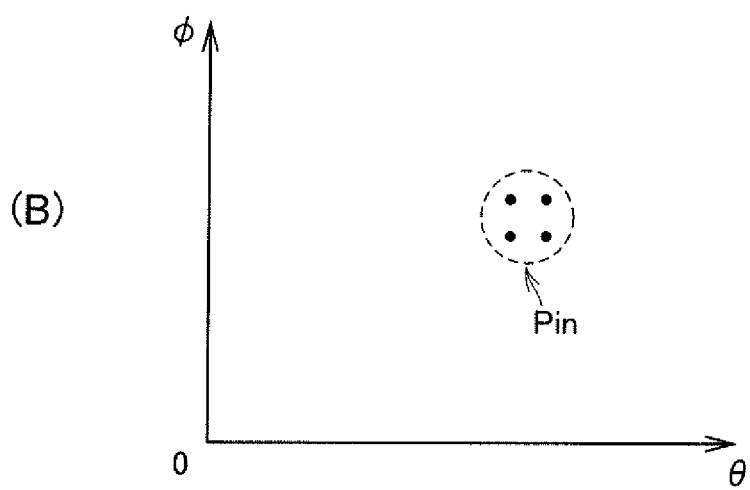

FIG.48
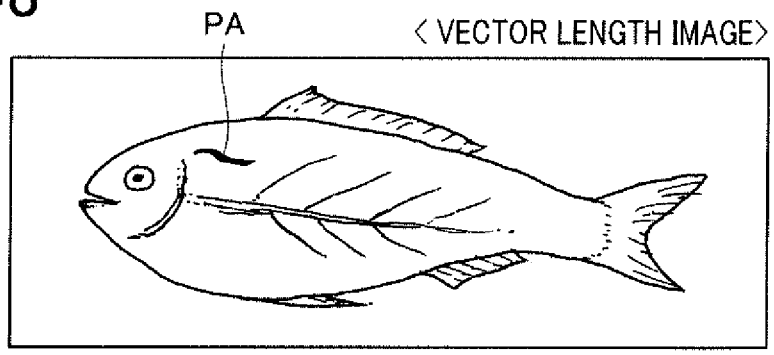
FIG.49
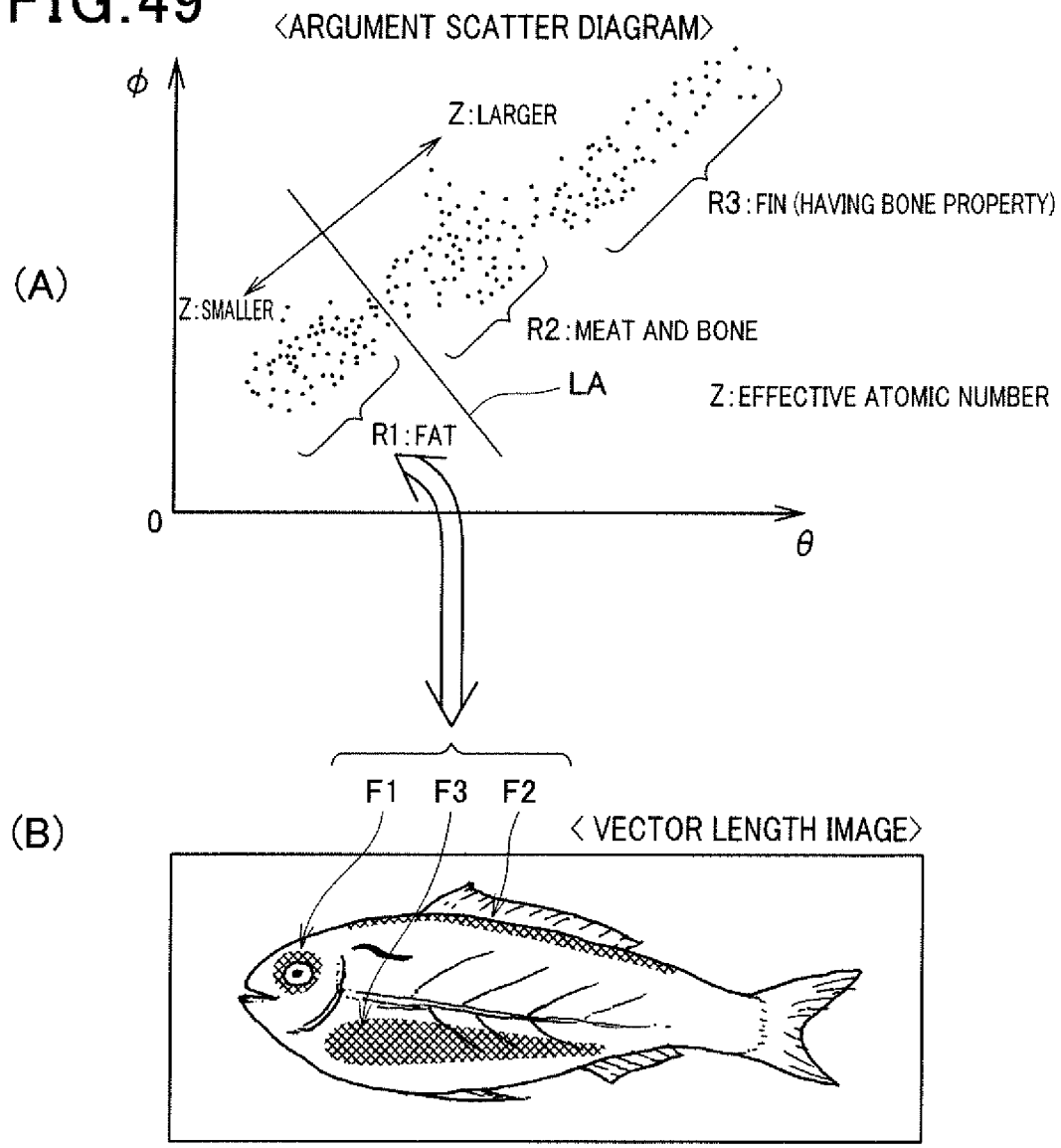
 : DISPLAY IN RED

<TWO-DIMENSIONAL CONTOUR LINE DISPLAY>

APPARATUS AND METHOD OF PROCESSING DATA ACQUIRED IN X-RAY EXAMINATION, AND X-RAY EXAMINATION SYSTEM EQUIPPED WITH THE APPARATUS

TECHNICAL FIELD

The present invention relates to a data processing apparatus and a data processing method, which are able to process X-ray transmission data acquired from an object by X-ray imaging, and an X-ray examination system equipped with the data processing apparatus. In particular, the present invention relates to man-machine interface functions, such as display or presentation of determined results depending on user's requests in a data processing apparatus, a data processing method, or an X-ray examination system, in which i) a type or property of a portion of interest of an object (such as food, industrial products, or part of a human body) or a substance (whose compositions differ from the object) which may be present inside the object or on the outer surface of the object is detected from X-ray transmission data, or ii) the type or property of an object is identified (determined or estimated) from X-ray transmission data.

RELATED ART

In recent years, the need for identifying the type and/or characteristics of an object by using X-rays has arisen in various places. An example can be seen in inspecting foreign materials which might be contained in various food items, which has shown a great rise in view of keeping public health and food safety.

For such a need, various kinds of X-ray inspection have been proposed. Among them, the most spotlighted inspection method is a method with which X-rays are radiated toward food so as to transmit therethrough so that data of transmitted X-rays are processed to acquire information of substances in or on the food. An example can be provided as an in-line X-ray inspection system in which an X-ray source and a detector are arranged with a conveyor's belt located therebetween, and food being inspected is placed on the belt. In this system, the food on the belt (line) is conveyed and passes an X-ray radiation field produced between the X-ray source and the detector. X-rays which have passed through the food are detected by the detector located under the belt, and processed into detection data from which images are generated. The images are then subjected to, for example, designated software processing so that a foreign matter which might have been contained in the food can be detected based on shadows of the images. In this case, objects being inspected are not necessarily limited to foreign matters, but may be substances which will cause contrast differences for the X-rays and whose sizes, shapes, and/or weights should be obtained more accurately.

In such an X-ray inspection, it has been desired to widen its applications more than now. For example, there is a need for security check in facilities such as airports, in which, without opening bags or mail articles, types and/or positions of unknown contents in such bags etc. are desired to be detected. In addition, the foregoing foreign matter inspection can be used in a case where a foreign matter (e.g., metal piece) might be contained in a previously known object (e.g., food item such as bread). In this case, there is also a need for detecting whether or not the foreign matter is present therein and, if there is a foreign matter, deciding the actual type of the matter. In other words, there has been a higher potential need for identifying, using the X-rays, the type and/or three-dimensional position of the object (substance). In the field of medical examinations, there are a wide variety of demands for detecting lesions occurring due to changes of properties of organs, which includes detection of cancer, tumor or calcification, which can be referred to as foreign matters, or detection of infarction portion of the heart.

In response to this growing need, there is a known technique explained in PTL 1: JP-A 2010-091483, for example. This PTL 1 provides a method and a system for detecting foreign matters, which is based on an examination technique referred to as a dual energy method (or a subtraction method). This examination method utilizes a difference in X-ray transmission information, which is caused when two types of energies (wavelengths) of X-rays pass through a substance. Practically, two types of X-rays having lower and higher energies are used to produce X-ray images from those X-rays, and the produced images are subjected to mutual subtraction, so that an image having pixel components showing a contaminated foreign matter can be extracted. This difference image is then subjected to comparison with a threshold, whereby the foreign matter is detected. This is the basic scheme of this examination. Especially, in the method disclosed by PTL 1, suitable parameters are automatically set for the difference computation, which is led to higher-sensitivity foreign matter detection.

Meanwhile, in the examination method based on the dual energy method, there is also a known technique disclosed by non-PTL 1. This non-PTL 1 provides a system employing the foregoing basic structure for the dual energy method and in addition to this, an improvement for objects overlapped on one another on the belt. Even if such overlapped objects are present on the belt, the system is devised to prevent such overlapped objects from being detected as a foreign matter, thereby enabling the system to detect the foreign matters with higher sensitivities.

It is possible to raise detection sensitivity of an object or foreign matters which might be contained in the object if the dual-energy method set forth in the foregoing PTL1 or non-PTL 1. However, it is very difficult to obtain information showing what kind of a foreign matter is contaminated in an object or, in addition to this, where the foreign matter is located three-dimensionally in the object, which are best interested in the foreign matter inspection.

That is, the difficulty of identifying (determining or estimating) the types or other information of a foreign matter results in difficulty of identifying the type of substance itself through which the X-rays pass or, in addition to this, the three-dimensional position of the substance. This is very inconvenient in cases where, for example, a foreign matter is desired to be inspected as to whether or not the foreign matter is truly contaminated in an object whose type itself is unknown.

In order to remove such a drawback, the methods disclosed by PTL 2 and PTL 3 are proposed.

This proposed configuration in PTL 2 uses images acquired from a tomographic apparatus or other apparatus which operates on a laminography technique to identify the types of substances contained in an object with precision in a convenient manner. Specifically, the energy of X-rays is divided into a plurality of energy ranges in which, each of the X-ray photons are counted and the counts are processed into reconstructed object images. These images are used to identify a substance which is present in the region of interest of the object. If using this method, a reference image is produced based on the counts obtained by imaging a substance whose thickness and density are uniform and the pixel values of the object image are normalized by, pixel by pixel, the pixel values of the object image by the pixel values of the reference image. From the normalized pixel values of the object image, a two-dimensional scatter diagram is produced which has two axes; one axis is assigned to X-ray absorption information and the other axis is assigned to X-ray beam hardening information. This scatter diagram is used to provide identification information which indicates the types of substances which are present in an imaged portion of an object.

In the proposed configuration in PTL 3, an X-ray beam is radiated from an X-ray tube (21) and transmitted through an object, and its photons are detected by a photon counting detection unit (26), so that counts of the X-ray photons are processed every X-ray energy range and detector pixel. Using the counts, an image of the object is calculated and a region of interest is set on the image. Pixel values which is a background for the object within the region of interest is then removed from the image. Based on the counts obtained every X-ray energy range and pixel in the region of interest, transmission characteristics of substances inherent to the X-ray are calculated every pixel as inherent information inherently indicating the substances. This inherent information indicates quantities which are based on linear attenuation coefficients in the respective X-ray paths, and calculated as the quantities which are independent of the lengths of X-ray transmission paths (which can be referred to as thicknesses of the object in the path directions) in the object and which are normalized. Such quantities are calculated for respective X-ray energy ranges. Accordingly, if the number of X-ray energy ranges being processed is three, the inherent information is calculated as three-dimensional mass attenuation vectors ($\mu_{1m}$, $\mu_{2m}$, $\mu_{3m}$), and mapped as a three-dimensional scatter diagram. If the number of X-ray energy ranges being processed is two, a one-dimensional scatter diagram is mapped.

In any of the scatter diagrams, the vectors are calculated at every detector pixel. Therefore, mapped scattering points on the scatter diagrams, that is, the gradients of the respective vectors, indicate X-ray transmission characteristics inherent to substances which exist in the X-ray transmission paths and function as the inherent information for the substances. This was found out by the inventors in PTL3, and confirmed by some simulations.

In substance identification technique taught by the PTLs 2 and 3, the two- or three-dimensional scatter diagram is used, thus providing visualization which is of some help for understanding substance components are mixed in what state.

CITATION LIST

Patent Literature

[PTL 1] JP-A 2010-091483
[PTL 2] JP-A 2013-119000
[PTL 3] WO 2016/171186
[Non-PTL 1] Anritsu Technical No. 87, March 2012, "Development of Dual-Energy X-Ray Inspection System"

SUMMARY OF INVENTION

Technical Problem

However, the scatter diagrams set forth in PTLs 2 and 3 have still suffered from an unsolved difficulty that how such scatter diagrams should be observed and interpreted. In other words, in understanding components of a substance being examined or information about foreign matters which may be contained in a substance being examined using such scatter diagrams, there has not been provided a sufficient interface between a scatter diagram displayed on a monitor and a user who interprets the scatter diagram. One example can be explained in observing a three-dimensional distribution diagram on a two-dimensional monitor screen. In this case, the scatter diagram two-dimensionally displayed depends on a view point (a viewing direction) at (along) which the scatter diagram is coveted to the two-dimensional diagram to be displayed. This is true of rotated display of a three-dimensional scatter diagram. Hence, it is desired to raise an interface function for display or analysis which is not seldom influenced by the forgoing difficult display conditions.

In view of the foregoing situations of the conventional X-ray inspection, the present invention is made and directed to provide i) a data processing apparatus and a data processing method, which are able to identify (estimate or determine) the type or characteristics of a substance composing an object being inspected or examined by X-rays or a part (an interested portion) of the object, and are able to display or analyze the determined results with no dependency on observation directions required when the display or analyzation is performed, so that interface functions for the degermation process can be provided sufficiently, and ii) an X-ray examination system equipped with such a data processing apparatus or capable of executing such a data processing method.

Solution to Problem

In order to accomplish the object, a data processing apparatus according to one aspect of the present invention includes count acquiring means configured to acquire a count of photons of an X-ray beam, the X-ray beam being radiated from an X-ray generator and transmitted through an object, and detected by a photon counting detector, the photons being counted every pixel of the detector and every one of n-pieces (n is a positive integer of two or more) energy ranges or every one of energy ranges whose number is less than n; image data calculating means configured to calculate image data indicative of a transmission state of the X-ray beam through the object, based on the count acquired by the count acquiring means; attenuation information calculating means configured to calculate attenuation information indicative of how the X-ray beam is attenuated during transmission through the object, based on the image data calculated by the image data calculating means, every one of the n-piece energy ranges or every one of the energy ranges whose number is less than n and every one of the pixels or every one of pixel groups into each of which the pixels are grouped, the attenuation information including i) inherent information inherently depending on a type or a property of the object, the inherent information being indicated by a quantity of a vector in an n-dimensional coordinate whose dimension is equal in number to the n-piece energy ranges; and ii) associated information being associated with the inherent information and depending on a length of a path along which the X-ray beam passes though the object; inherent information producing means configured to produce only the inherent information which is independent of the associated information, from the attenuation information calculated by the attenuation information calculating means; and scattering point calculating means configured to calculate scattering points to be mapped in the n-dimensional coordinate or a coordinate which is less in dimension than the n-dimensional coordinate, the scattering points depending on the inherent information produced by the inherent information producing means.

In this configuration, the counts acquired by the count acquiring means include counts measured in various other modes. For example, when an X-ray flat panel detector is adopted to perform photon counting X-ray detection, counts detected by the X-ray flat panel detector can also be adopted. Photon counts measured by an X-ray CT imaging can be adopted as well. Another example is originated from a line X-ray detector which is moved relatively to an object together with an X-ray generator for X-ray scanning. In this case, photon counts can also be acquired, so can be applied to the foregoing configuration. The X-ray detector can include a combination of a scintillator and a photoelectric conversion element (as this example, a silicon photomultiplier (SiPM) is preferred), or include a direct-conversion type of X-ray detector which directly converts the X-ray to electrical signals.

Another mode of the present invention relates to a processing method having the identical function as that of the foregoing processing apparatus and/or an X-ray examination system provided with the foregoing data processing apparatus (such as an X-ray non-destructive inspection equipment or an X-ray medial inspection equipment).

Main technical terms used in the invention are defined as follows.

First of all, the term "X-ray examination system" includes a medical X-ray radiographing apparatus and a medical X-ray diagnostic apparatus and also includes an X-ray nondestructive inspection apparatus. The term "X-ray inspection" also conceptually includes medial X-ray examination and nondestructive inspection.

In addition, the term "object being examined (simply object)" or "target" is defined as an object placed in the object space of an X-ray examination system, in which the object undergoes shot-imaging or scanning by X-rays for acquiring frame data as X-ray transmission data.

The term "the whole of an object being examined (object or target)" means the whole of substances composing each object. For example, when the object being examined is food (for instance, vegetables such as peppers or tomatoes, sandwich loafs, pot noodles, edible meats, or fishes), the whole of the object means individual items placed on the conveyor's belt of the X-ray examination system for inspection. When the object is composed of industrial products or pieces of baggage inspected in the airport, the whole of each object means each item subjected, as a separate thing, to inspection performed by the X-ray examination system.

In contrast, the term "part of an object being examined" is defined as a term which shows only a part of goods being examined. This part is, for example, designated automatically or by hand in an X-ray perspective image. By way of example, in inspecting foreign matters in vegetables, the part of such an object is referred to as a part of respective different vegetables (e.g., cucumbers or tomatoes) carried by the conveyor's belt of an X-ray examination system. In cases where a region of interest (i.e., a part of an object) designated in an X-ray perspective image of the object is different from the original composition of the object, it can be evaluated such that a foreign matter is contaminated in the part designated using the region of interest.

Incidentally, in this foreign matter inspection, the remaining parts other than the foreign matter is processed as background components in data processing. Hence, the background components are data derived from compositions (containing air) of the object itself, which are present in both the background region and the peripheries thereof. When the whole of an object is designated as a target region for identifying substances or determining characteristics, the background components are only known components including air and the conveyor's belt for the inspection.

In addition, the "identification" of a substance is to perform discrimination to determine what type of material that the substance is made of, so that this term, identification, can be replaced by "determination, estimation or evaluation" in this application. The "property(properties)" of a substance is to perform discrimination to determine the physical state and the compositions of the substance and if an edible meat block is picked up as an easily understandable example as an object being examined, this term, property, is referred to as a rate between muscle and fat contained in the edible meat block. In the dental field, the term property, can be, as one example explained as a degree of progress in the periodontal disease (how deeply a tissue or cell is denaturalized).

Further, "a substance present in a region of interest" i) may be the whole or a part of an object being examined (object or target), or ii) may be present in the region of interest but a substance (such as a substance of interest including foreign matters) which is different from the object itself.

In this way, the substance identification in the present invention includes various types of modes, which are to identify the type of an object itself, to identify properties of an object itself, to detect that there is a substance other than the compositions of an object itself, and to identify the type of a substance other than the components of an object itself. Accordingly, the object is provided as things that have a shape, which are composed of elements such as a substance, material or composition. The object may be an article of which components are unknown, foreign matters which may be contained in the article, portions such as human breasts or jaws, or lesions which may occur in such a portion.

Effect of the Invention

According to the present invention, in non-destructive inspection of items or medical examination, inherent information inherently indicating a state of X-rays transmitted through an object, and associated information associated with the inherent information and additionally composed of part of the inherent information are produced. Moreover, the inherent information is generated by removing or apparently disappearing the associated information from the attenuation information. Scattering points depending on only the inherent information are mapped in the n-dimensional (n: a two or more positive integer) coordinate or in a coordinate whose dimensions are less than the n-dimension. The inherent information does not depend on the thickness of a substance existing in each of the X-ray paths (i.e., the length of each X-ray path in the object), but indicates a degree of X-ray attenuation, thereby being handled as information showing an inherent characteristic to the object. Practically, this inherent information can be expressed by a gradient of each of the vectors. Only the gradient components are mapped in the coordinate for display, whereby a user can observe and interpret the mapped information. This makes it possible to observe identified types of substance elements (if the object is a human body, the elements are tissues) or elements (corresponding to an effective atomic number), without being influenced by a user's view point position and/or directions.

BRIEF DESCRIPTION OF DRAWINGS

In the accompanying drawings:

FIG. 8 is an outlined flowchart explaining a key part of the substance identification performed by the data processor in a first present embodiment;

FIG. 9 is an illustration explaining generation of a three-dimensional vector showing an X-ray absorption amount, from each of the respective pixels composing a region of interest in an image obtained in energy range;

FIG. 18 is an illustration explaining one step in the image process in the first first embodiment;

FIG. 19 is an illustration explaining one step in the image process in the first first embodiment;

FIG. 36 is a diagram explaining another step of the image process in the fifth embodiment;

FIG. 48 is a pictorial illustration indicative of a vector length image of fish (yellowtail is exemplified), which results from an experiment conducted as applied example;

FIG. 49 is an illustration showing an associated performance (relationship) between an argument-data scatter diagram and the vector length image according to the applied example;

DESCRIPTION OF EMBODIMENTS

Hereinafter, with reference to accompanying drawings, an embodiment of a data processing apparatus and a data processing method, which are for X-ray examination, will now be described, and embodiments of image processing performed by X-ray examination systems provided with the data processing apparatus will then be described as modifications.

First Embodiment

First, with referring to FIGS. 1 to 19, as one embodiment, a data processing apparatus and a data processing method for X-ray examination according to a mode of the present invention will now be described.

Figure 1:
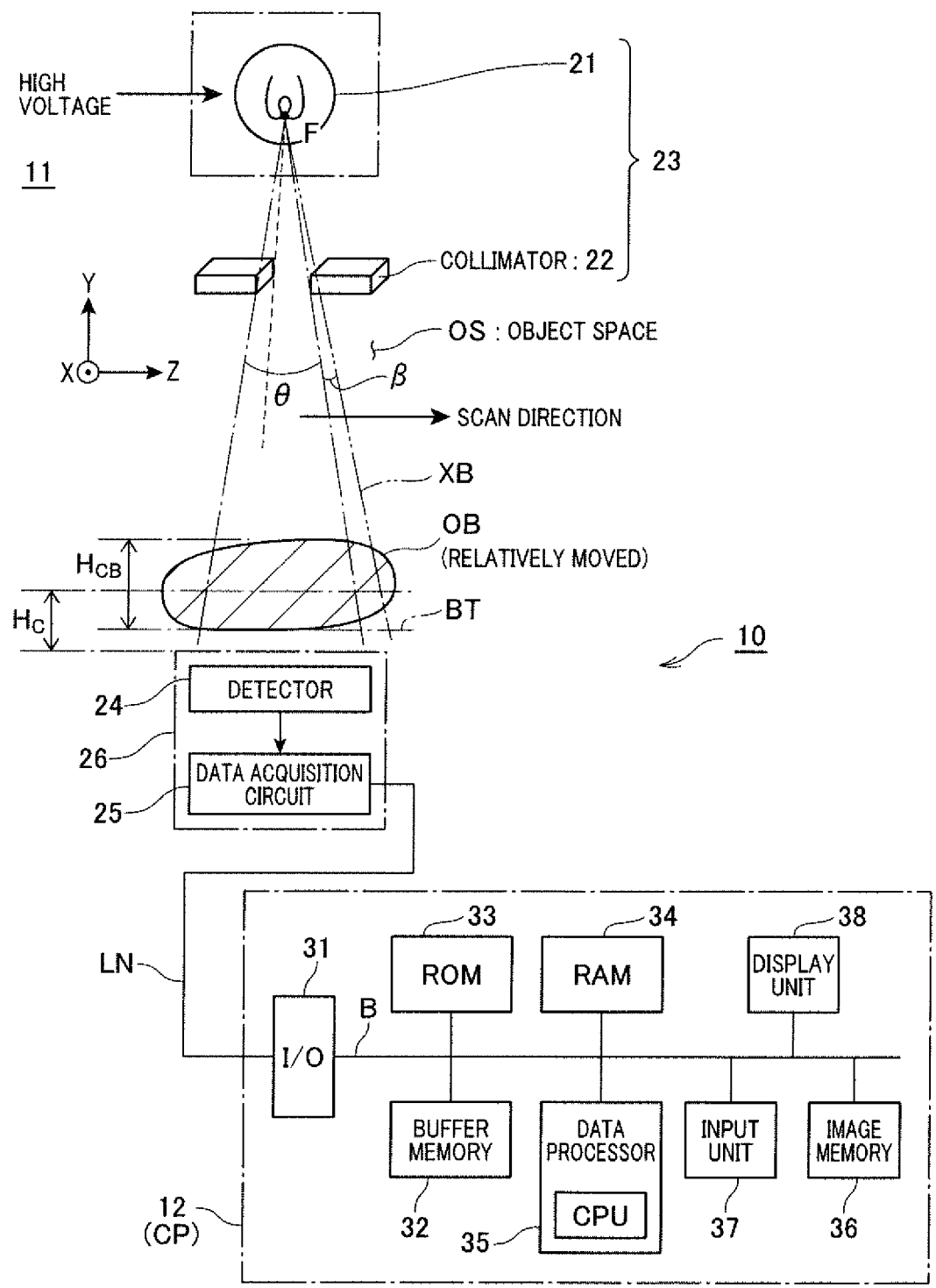
FIG. 1 is a block diagram outlining an X-ray examination system provided with a data processing apparatus according to an embodiment of the present invention.

FIG. 1 outlines the configuration of an X-ray examination system 10 (an X-ray examination apparatus). In the present embodiment, the data processing apparatus and a data processing method will now be focused, in which known configurations of this X-ray examination system 10 are simplified in explanations thereof.

The X-ray examination system 10 is provided with an examination (or diagnostic) main frame 11 and a data processing apparatus 12 communicably connected to the examination main frame 11 via a communication line LN.

The present embodiment features, as will be described later, that the data processing apparatus 12 is able to process data acquired by detecting X-rays from an object, based on a photon counting scheme for the X-rays. That is, the feature exists in that how an interface function is provided between the data processing apparatus 12 and a user when acquired data are analyzed and displayed. For this reason, it may be that photon counting data received by the data processing apparatus 12 are acquired in any kind of acquisition mode.

Figure 2:
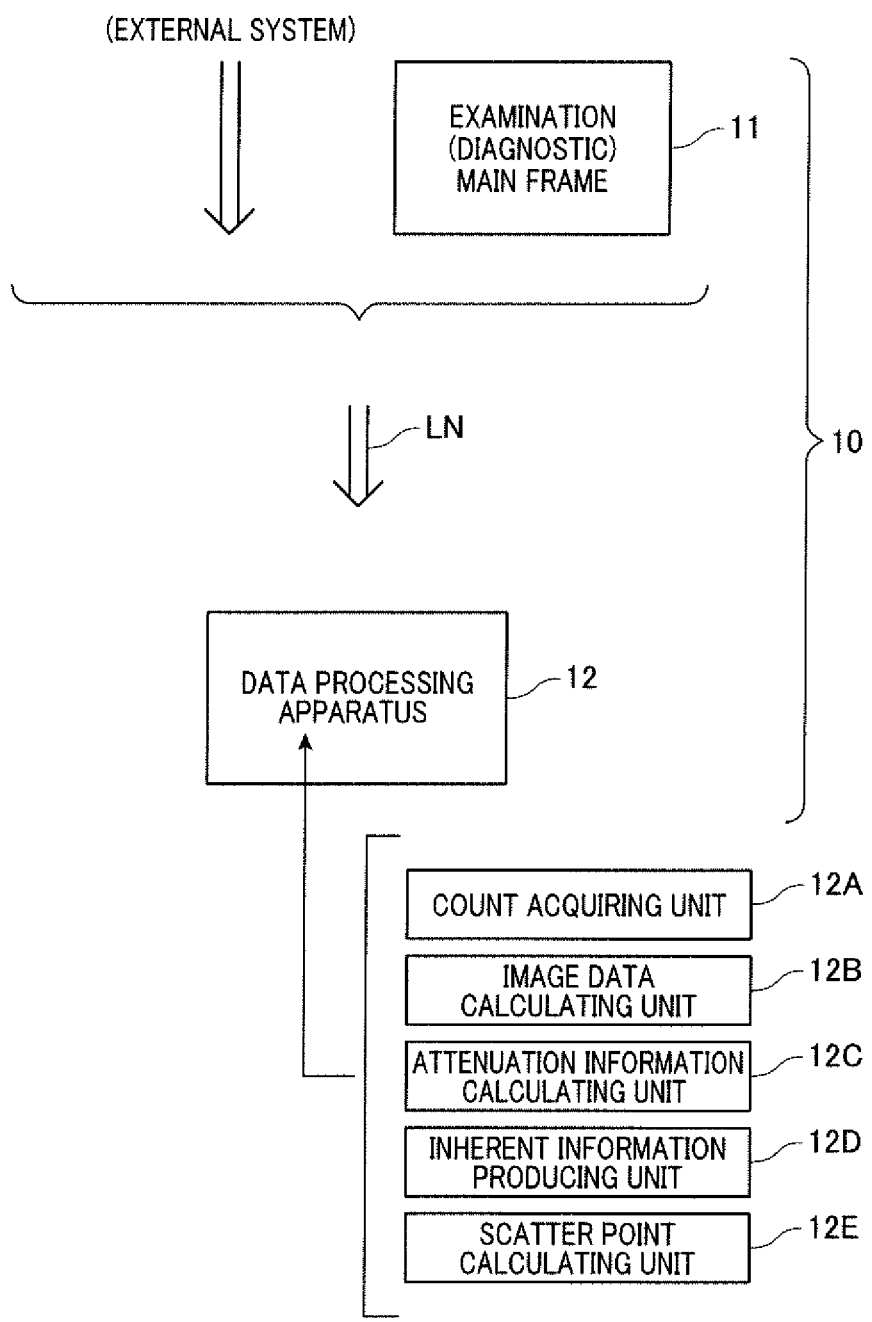
FIG. 2 is a block diagram illustrating how to acquire X-ray data which are provided to the data processing apparatus to which the present invention can be applied.

Hence, in a configuration pictorially shown in FIG. 2, the examination main frame 11 can be configured by any type as long as a photon counting data detection can be made to and from an object. For example, in this system, the data processing apparatus 12 can be functionally integrated with a controlling unit provided in the X-ray examination system 10 or can be arranged as a separate apparatus from the X-ray examination system 10. Alternatively, it may be configured that photon counting data which have been acquired by an external system are sent to the data processing apparatus 12 via a communication line such as Internet or a recording medium such as ROM.

In the pictorially shown configuration in FIG. 2, for instance, the examination main frame 11 can adopt an X-ray flat panel type of detector, in which the X-ray flat panel is used to detect X-ray beams on a photon counting scheme. An alternative is to receive photon counting data acquired by an X-ray CT scanner. Moreover, a linear detector may be adopted as the X-ray detector, in which the linear detector is arranged to be moved (scanned) relatively to an object together with an X-ray generator. In this configuration, the X-ray detector may be structured as a combination of a scintillator and a photoelectric conversion element (preferably, such as a silicone photomultiplier (SiPM)), or as a direct-conversion type of detector which is able to directly convert X-ray to corresponding electrical signals.

A system, which will be described later, is exemplified as a system provided with a direct-conversion X-ray detector which employs a semiconductor device directly convert X-ray to corresponding electrical signals and a circuitry configuration which allows this detector to perform photon counting.

Though being exemplified later, the configuration of the data processing apparatus 12 is generalized as below. The data processing apparatus 12 includes, at least, a count acquiring unit (count acquiring means) 12A configured to acquire a count of photons of an X-ray beam, the X-ray beam being radiated from an X-ray generator and transmitted through an object, and detected by a photon counting detector, the photons being counted every pixel of the detector and every one of n-pieces (n is a positive integer of two or more) energy ranges in an X-ray energy spectrum or every one of energy ranges whose number is less than n; an image data calculating unit (image data calculating means) 12B configured to calculate image data indicative of a transmission state of the X-ray beam through the object, based on the count acquired by the count acquiring unit 12A; an attenuation information calculating unit (attenuation information calculating means) 12C configured to calculate attenuation information indicative of how the X-ray beam is attenuated during transmission through the object, based on the image data calculated by the image data calculating unit 12B, every one of the n-piece energy ranges or every one of the energy ranges whose number is less than n and every one of the pixels or every one of pixel groups into each of which the pixels are grouped, the attenuation information including i) inherent information inherently depending on a type or a property of the object, the inherent information being indicated by a quantity of a vector in an n-dimensional coordinate whose dimension is equal in number to the n-piece energy ranges; and ii) associated information being associated with the inherent information and depending on a length of a path along which the X-ray beam passes though the object; an inherent information producing unit (inherent information producing means) 12D configured to produce only the inherent information which is independent of the associated information, from the attenuation information calculated by the attenuation information calculating unit 12C; and a scatter point calculating unit (scattering point calculating means) 12E configured to calculate scattering points to be mapped in the n-dimensional coordinate or a coordinate which is less in dimension than the n-dimensional coordinate, the scattering points depending on the inherent information produced by the inherent information producing unit 12D. The respective units 12A to 12E can be realized functionally by making a computer execute preset software programs or by employing electronic hardware circuitry such as FPGA (field-programmable gate array).

The explanation will now return to FIG. 1. The X-ray examination system 10 is employed as, for example, an X-ray nondestructive inspection system or a medical X-ray panoramic radiography system. An object being examined by this X-ray examination system 10 ranges widely, such as food, industrial products, or patient's breasts. An easier comprehensive example of this system is an in-line food inspection apparatus used to inspect whether or not food (e.g., vegetables such as sausages or peppers) contains foreign matters, but is not always confined to this example. Besides being these examples, the food may be exemplified as fresh fishes, and in such a case, the fishes are subjected to inspection of whether or not foreign matters such as fishhooks are left in the fishes. In other words, if interpreting the meaning of the foreign matter in other ways, this examination system can be applied to estimation of characteristics of various items, including checking a content rate of fat in a block of edible meat block, a mixture of foreign matters or bones in a block of edible meat, and a content of voids or water in wood. For the industrial products, the system can be applied to checking of various kinds, including checking states of electric substrate parts or contact states within soldered bumps. In the mammography for medically checking human body breasts, the system can be used for finding out lesions such as calcification and/or masses in the breasts or determining a content rate of mammary glands at higher accuracies.

In performing the nondestructive inspection or the X-ray panoramic radiography, the data processing apparatus and the data processing method for X-ray examination according to the embodiment are operative based on abruption information (or attenuation information) of X-rays when the X-rays are transmitted through a substance, and process such information so as to identify (or determine, distinguish, detect, or decide) the type or characteristics (or aspects or states) of the substance. This process is a basic factor of this system. In the following description, this process is called "substance identification" as a whole, if desired.

As shown in FIG. 1, the X-ray examination system 10 has the examination main frame 11 and, in this main frame 11, there is provided an object space OS in which X-, Y- and Z-axes are virtually set for an orthogonal coordinate system. For nondestructive inspection, the system 10 is provided with an X-ray generator 23 with an X-ray tube 21 and a collimator 22. The X-ray generator 23 generates X-ray beams into the object space OS, in which the X-ray beams have a preset cone angle θ in a scan direction (the Z-axis direction) and a preset fan angle β in a direction (the Y-axis direction) along a section (an XY plane) perpendicular to the scan direction. The X-ray tube 21 has a spot-shaped X-ray focal point F (having a radius of for example 1.0 mmφ) and is constructed in a rotating anode X-ray tube, for instance. To this X-ray tube 21, a driving high voltage is supplied from a not-shown X-ray high voltage generator for X-ray radiation.

The X-ray examination system 10 is also provided with an X-ray detector 24 (hereinafter simply referred to as a detector) movably arranged so as to be opposed to the X-ray tube 21 with a predetermined distance apart therebetween. The detector 24 is configured by linearly connecting a plurality of modules and, due to this connection, as a whole, the detector 24 has a thin and rectangular X-ray incidence window. Each of the modules is formed as, what is called, a direct conversion type of X-ray detecting member which directly converts X-rays to electrical signals. Each module has a detection layer composed of a semiconductor material, such as CdTe or CZT, in which, for example, pixels of 20×80 (each pixel has a size of 0.2 mm×0.2 mm) are formed on the detection layer. Though not shown, on both sides of the detection layer having the plural pixels, charging and collecting electrodes are arranged for applying a bias voltage between the electrodes.

Figure 3:
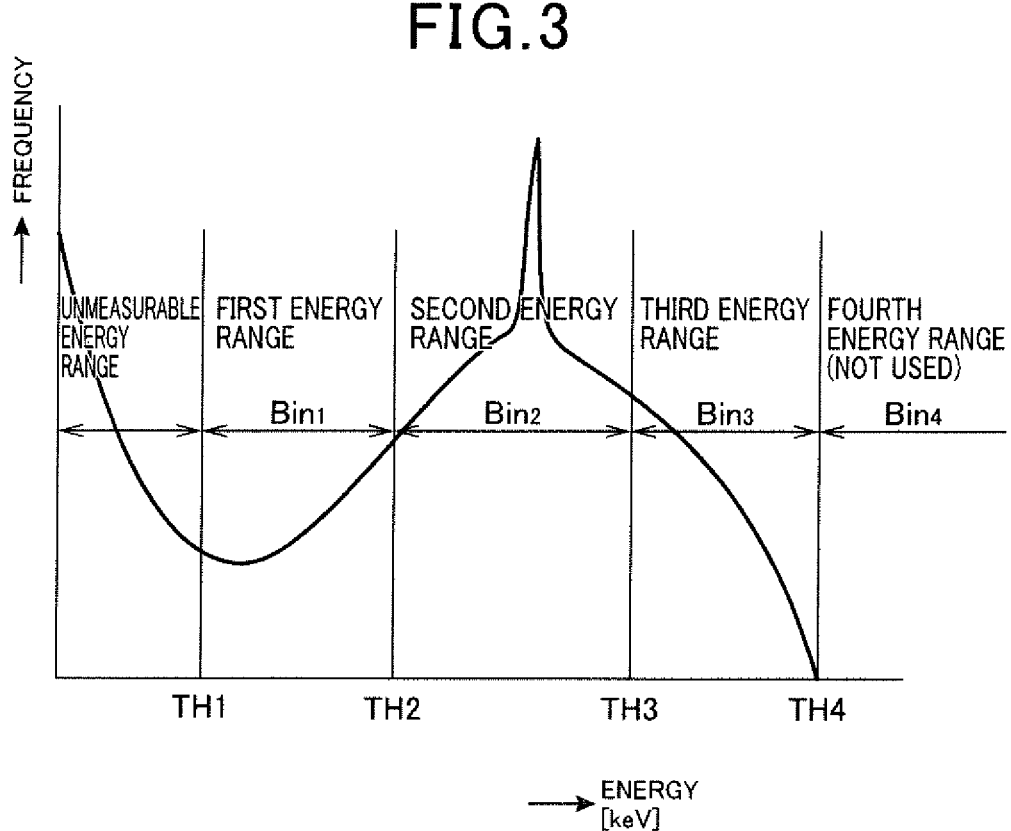
FIG. 3 is a graph exemplifying energy ranges which are set to a photon counting detector and an X-ray energy spectrum.

This detector 24 is a photon counting detector (a photon counting type of detector), which regards X-rays as an aggregate of photons having various energies and is capable of detecting of measuring the number of photons of the X-rays every energy range set to the X-rays. As shown in FIG. 3, the energy ranges are set for example as four energy ranges $Bin_1$ to $Bin_4$. The number of energy ranges is not limited to four, and may be any number chosen as two or more regions.

By this detector 24, X-ray intensities are detected as digitized counts (integrated numbers) showing the number of photons at intervals, at every pixel and in every energy range Bin. When a signal photon impinges into one pixel, an electric pulse signal is generated at this pixel, whose wave height is pending on the energy amount of that photon. The wave height of this electric signal, that is, an energy amount is classified into a corresponding energy range Bin, in which the count increases by one. The counts in the respective energy ranges Bin are acquired as their accumulated amounts (in the digital signal form) at the respective pixels.

This acquisition process is performed by a data acquisition circuit 25 incorporated as an ASIC layer under the detection layer of the detector 24. The detector 24 and the data acquisition circuit 25 configure a detection unit 26. It is therefore possible that the detection unit 26, practically the data acquisition circuit 25, sends X-ray transmission data (in the form of frame data) at the designated frame rate, to the data processing apparatus 12.

The X-ray examination system 10 having this configuration is exemplified in publications of, for example, JP-A 2007-136163, WO 2007/110465 A1, and WO 2013/047778 A1. In addition, the foregoing photo counting detector 24 is also exemplified by WO 2012/144589 A1.

In cases where this X-ray examination system 10 is used for a dental X-ray panoramic radiography for instance, the object OB being examined is a patient's head. In such a case, the pair of the X-ray generator 23 and the detector 24 is moved around the head so as to rotate on a rotation axis which is defined for example as a head center which is a line in the X-axis direction. This scanning structure for the X-ray panoramic radiography is also shown in JP-A 2007-136163, by way of example.

Furthermore, the data processing apparatus 12 is configured to receive, via the communication line LN, the X-ray transmission data (i.e., frame data) from the X-ray examination system 10. This data processing apparatus 12 can be provided as either an apparatus or an inspection system which is integral with the X-ray examination system 10. Additionally, when the data processing apparatus 12 is communicably connected to the X-ray examination system 10 as shown in this embodiment, the connection may be established in either always-on connection or whenever necessary. The data processing apparatus 12 may be provided as a stand-alone form.

As detailed later, the data processing apparatus 12 is configured to process the received X-ray transmission data in order to provide information inherent to the types or characteristics of substances which compose the object itself and/or substances present in a region of interest of an object, and further, to test whether or not the other substances such as foreign matters are mixed with an object. In addition, it can be rephrased such that differences in types or properties of substances mean differences or changes in the effective atomic numbers of the substances.

[Acquisition of Inherent Information to Substance and Details of Data Processing]

Hereinafter, the data processing apparatus 12 will be detailed in its structure and action, together with a scheme for acquiring the inherent information of substances, which is one of the features of the present information.

The data processing apparatus 12 is configured, by way of example, as a computer system CP. This computer system CP itself may be a computer system having known calculation functions, in which an interface (I/O) 31 is provided which is connected to the detection unit 26 via the communication line LN. To the interface 41, via inner buses B, a data processor 35 (simply, a processor or a computer) equipped with a buffer memory 32, a ROM (read-only memory) 33 (which foundations as a non-transitory computer readable medium), a RAM (random access memory) 34, and a CPU (central processing unit); an image memory 36; an input unit 37; and a display unit 38 are communicably connected with each other.

The ROM 33 is provided to previously memorize computer-readable programs for identifying substances, which enables the data processor 35 to read the programs and store them in its work area for execution. The data processor 35 is a CPU dedicated to image processing. In the present embodiment, the ROM 33 is a representative of "Non-transitory computer recording readable mediums", which are practically composed of flash memories, EEPROMs or EPROMs. This non-transitory computer recording readable medium can be provided as a magneto-optical disk or a hard disk.

The buffer memory 32 is provided to temporarily memorize the frame data sent from the detection unit 26. The RAM is provided to temporarily memorize data required during processing of the data processor 35.

The image memory 36 is provided to store therein various image data and various kinds of information processed by the data processor 35. The input unit 37 and the display unit 38 function as a man-machine interface with users, in which the input unit 37 receives input information given by users and the display unit 38 presents images and others under control of the data processor 35. The interface 31, the input unit 37, and the display unit 38 configure an interface section which acquires information from the outside (for example, information given by users).

Figure 4:
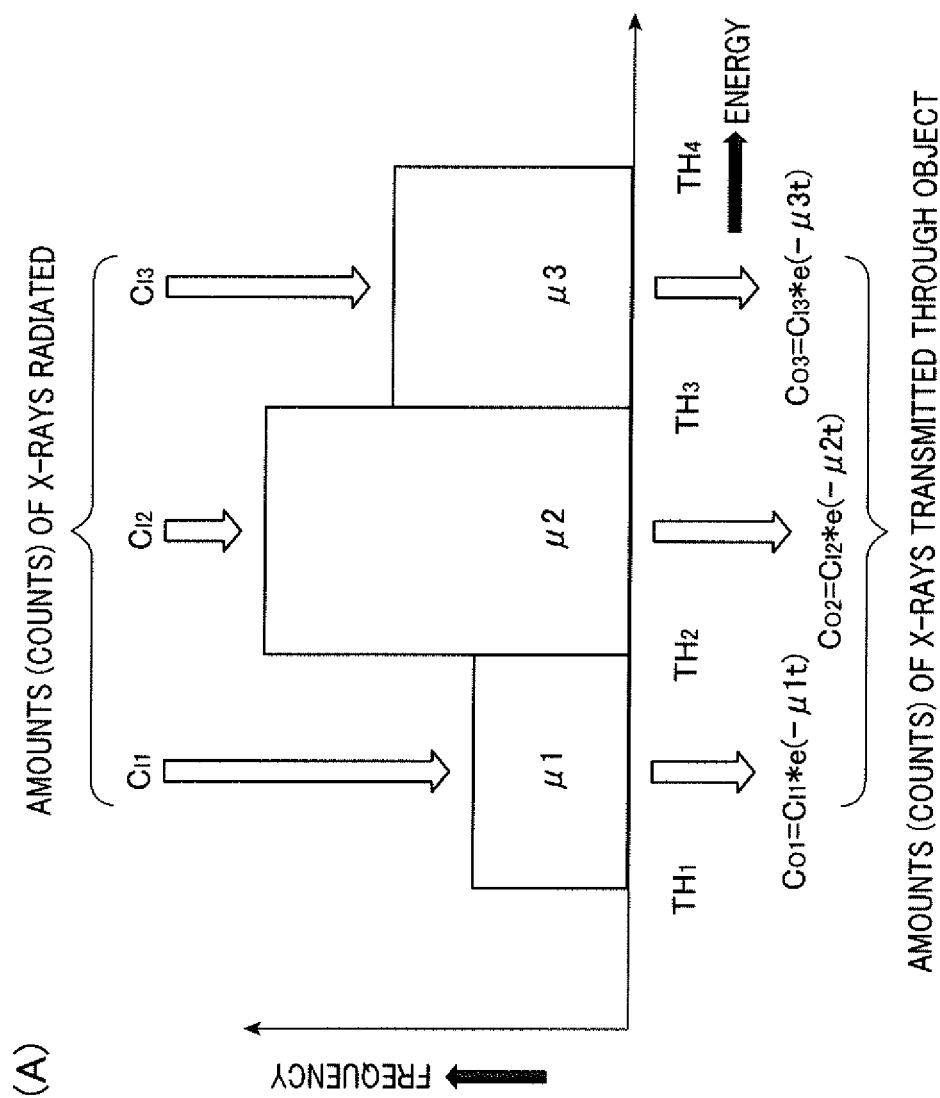
FIG. 4 shows views explaining a relationship between a single substance model and photon counting in each of the energy ranges.
Figure 5:
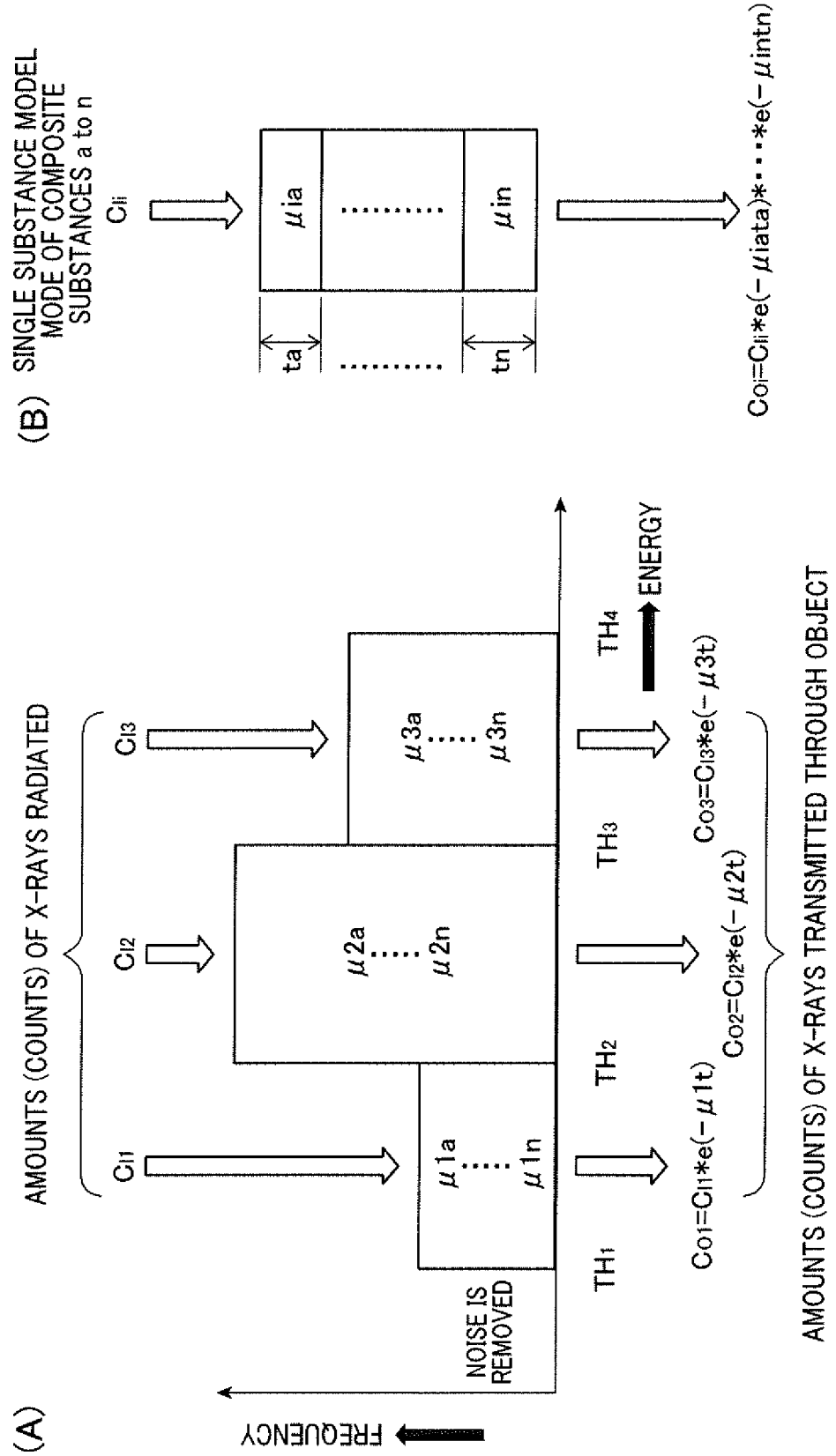
FIG. 5 shows views explaining a relationship between a model composed of a plurality of substances and photon counting in each of the energy ranges.

Relationship Between Data Acquisition and Substance Model on Photon Counting Method With reference to FIGS. 3 to 5, a concept for data accusation for each substance model will now be described, in which X-rays (fan-shaped X-ray beams), which are radiated from the X-ray tube 21, are transmitted through an object OB and the transmitted X-rays are detected by the detector 24 in the photon counting manner.

FIG. 3 shows a general profile in which the lateral axis indicates amounts of X-ray energy [keV] and the longitudinal axis indicates incidence frequencies (counts) of photons composing the X-rays. In the photon counting, as is known, the energy range shown by the lateral axis is divided into a plurality of energy ranges Bin so that thresholds TH are set to the lateral axis. In the example shown in FIG. 3, four thresholds $TH_1$, $TH_2$, $TH_3$, and $TH_4$ are set in the form of suitable reference voltage values applied to comparators (not shown), whereby the first to third energy ranges $Bin_1$, $Bin_2$, and $Bin_3$ are set as usable ranges. Incidentally, energy amounts lower than the first energy range $Bin_1$ fall into unmeasurable energy range due to much noise, while the fourth energy range $Bin_4$ upper than the largest threshold $TH_4$ is not used because this range $Bin_4$ is not related to counting the photons. As a result, in this example, the three energy ranges $Bin_1$, $Bin_2$ and $Bin_3$, which are the first to third energy ranges and which exclude the lowest and highest energy ranges, are used for the photon counting.

The shape of a frequency profile shown in FIG. 3 is decided by the type of material composing the anode of the X-ray tube 21 and voltage applied to the tube, and, as a typical example shown, the counts in the second energy range $Bin^2$ are the largest. Hence, the thresholds TH are decided in appropriate consideration for a balance among the values (i.e., frequencies or counts) counted in the respective energy ranges. These four thresholds $TH_1$ to $TH_4$ are set as voltage thresholds applied to each comparator assigned to each pixel of the detector 24 in the ASIC structure configured as the data acquisition circuit 25. Accordingly, the X-ray photons are counted for every pixel and every energy range. As a modification, any number of 3 or more can be adopted as the number of thresholds TH assigned to each pixel. If the number of thresholds TH is three, the number of usable energy ranges is two.

In producing X-ray transmissive images (density images), various modes can be adopted. Count information is obtained at each of the pixels forming the X-ray incidence window of the detector 24 and in each of the energy range Bin. Hence, by multiplying a count at each pixel in each energy range Bin by appropriately chosen weighting coefficients and performing a shift and add process with the multiplied counts, X-ray transmissive data (frame data) for each energy Bin can be obtained. In this process, any two or all among the three energy ranges Bin1 to Bin3 are selected, and the counts in such selected energy ranges can be subjected to multiplication of appropriately chosen coefficients and then to the shift and add computation, thereby producing one frame of X-ray transmissive data.

In this way, the energy information depending on the number of X-ray photons is collected at each of the pixels and in each of the energy ranges Bin. It is therefore possible to use the collected energy information in image formation or in other processes with consideration for a contribution of photon energies to the pixels. Further, depending on applications, any energy-weighted images can be produced, thus providing advantages over the convectional integration-type of X-ray remissions data acquisition.

In applying the photon counting technique to the substance identification according to the present application, it is reasonable to take it into account that a substance is composed of a single tissue or a plurality of tissues, and in each case, take X-ray absorption rates of the respective tissues into account. This is because a substance present in region being examined of an object OB may be tissue composing the object itself or may be another substance other than the substance composing the object.

(i) In Case a Substance is Composed of a Single Tissue (a Single Substance Model):

In the single substance model, as shown in FIG. 4(A), there are provided linear attenuation coefficients $\mu_1$, $\mu_2$, and $\mu_3$ (cm$^{-1}$) representing the first to third energy ranges $Bin_1$ to $Bin_3$, respectively. The linear attenuation coefficients are indices inherently indicating X-ray transmission characteristics of a substance.

When X-rays enter a substance, whose thickness is a thickness t (cm), having ray attenuation coefficients $\mu_1$, $\mu_2$, and $\mu_3$ which differ from each other among the energy ranges Bin, a substance model is represented as shown in the figure. Practically, the amounts (i.e., the number of photons) $C_{I1}$, $C_{I2}$, and $C_{I3}$ of incident X-rays are subjected to attenuation depending on both the thickness t and the ray attenuation to coefficients $\mu_1$, $\mu_2$, and $\mu_3$, respectively, and the amounts (i.e., the number of photons) of the output X-rays can be represented by:

$$C_{o1} = C_{I1} \times e^{-\mu_1 t}$$

$$C_{o2} = C_{I2} \times e^{-\mu_2 t}$$

$$C_{o3} = C_{I3} \times e^{-\mu_3 t} \qquad (1).$$

Hence, for the signal substance model composed of a single type of tissue, as shown in FIG. 4(B), responsively to the incidence of X-ray amounts $C_{Ii}$ (the number of photons) to the substance of a ray attenuation coefficients $\mu_i$ and a thickness t, the output X-ray amounts (the number of photons) can be represented by:

$$C_{oi} = C_{Ii} \times e^{-\mu_i t}$$

$$(i=1\sim 3) \quad (2).$$

(ii) In Case a Substance is Composed of a Plurality of Tissues (a Plural-Substance Model):

For the plural-substance model, from a viewpoint of X-ray absorption, as shown in FIG. 4(B), it can be presented that the substance is formed to have a layer structure composed of a layer having a thickness $t_a$ and a ray attenuation coefficients $\mu_{ia}$, a layer having a thickness $t_b$ and a ray attenuation coefficients $\mu_{ib}$, ..., a layer having a thickness $t_n$ and a ray attenuation coefficients $\mu_{in}$ are layered on one another. Hence, it is said that, as shown in FIG. 4(A), the first to third energy ranges $Bin_1$ to $Bin_3$ are represented respectively, in terms of X-ray attenuation, by ray attenuation coefficients $\mu_{1a}, \ldots, \mu_{1n}; \mu_{2a}, \ldots, \mu_{2n}; \mu_{3a}, \ldots, \mu_{3n}$ (cm$^{-1}$). When X-rays enter this layered substance, which has the ray attenuation coefficients $\mu_{1a}, \ldots, \mu_{1n}; \mu_{2a}, \ldots, \mu_{2n}; \mu_{3a}, \ldots, \mu_{3n}$ which are different from each other for the respective energy ranges Bin and which has the layer thicknesses $t_a, \ldots, t_n$ (cm), can be modeled as shown in the figure. In other words, the incident X-ray amounts (the number of photons) $C_{I1}$, $C_{I2}$, and $C_{I3}$ are attenuated depending on the ray attenuation coefficients $\mu_{1a}, \ldots, \mu_{1n}; \mu_{2a}, \ldots, \mu_{2n}; \mu_{3a}, \ldots, \mu_{3n}$ and the thicknesses $t_a, \ldots, t_n$, and their outputted X-ray amounts (the number of photons) can be represented by:

$$C_{o1} = C_{I1} \times e^{-\mu_{1a} t_a} \times \ldots \times e^{-\mu_{1n} t_n}$$

$$C_{o2} = C_{I2} \times e^{-\mu_{2a} t_a} \times \ldots \times e^{-\mu_{2n} t_n}$$

$$C_{o3} = C_{I3} \times e^{-\mu_{3a} t_a} \times \ldots \times e^{-\mu_{3n} t_n} \quad (3).$$

It is thus possible to represent the plural-substance model composed of a plurality of compositions such that, as shown in FIG. 5(B), when receiving incidence of X-ray amounts $C_{Ii}$ (the number of photons), the outputted X-ray amounts (the number of photons) are defined as:

$$C_{oi} = C_{Ii} \times e^{-\mu_{ia} t_a} \times \ldots \times e^{-\mu_{in} t_n}$$

$$(i=1\sim 3) \quad (4)$$

[Processing Procedures]

On the assumption the photon counting and the linear attenuation amounts pt are related to each other based on the foregoing substance model, a process for substance identification, which is executed by the data processing apparatus 12, will now be described. In the data processing apparatus 12, the data processor 35 is configured to perform preassigned programs, thus providing the substance identification which is according to a procedure shown in FIG. 6.

[Preprocessing]

First, the data processor 35 determines whether or not it is necessary to acquire images, for example, automatically or interactively with a user (step S1), and waits for timing of the image acquisition. When it is determined that the image acquisition is necessary (YES at step S1), the data processor reads frame data previously stored in the butter memory 32 and place them in the RAM 34 for example (step S2). Pictorially shown in FIG. 6, the frame data are composed of i) three frame data $FD_1$, $FD_2$ and $FD_3$ each consisting of the counts of the X-ray photons whose energy amounts belong a corresponding one of the three energy ranges $Bin_1$, $Bin_2$ and $Bin_3$ and ii) a frame data $FD_{all}$ consisting of the counts of the X-ray photons whose energy amounts belong to an all energy range $Bin\_{all}$ ($Bin_1 + Bin_2 + Bin_3$).

The data processor 35 then determines whether or not the substance should be identified, interactively with user's instructions or in response to automatic instructions (step S3). Until receiving instructions for the substance identification, the processing waits, and when receiving instructions for ending the substance identification, the processing will be ended (step S4).

[Production of Focused Image]

When the data processor 35 determines execution of the substance identification at step S3 (YES at step S3), the processor then designates a section, for example, which intersects with an object OB being examined, automatically or interactively with the user (step S5).

By way of example, in interactively designating a position of the section, a user can use the input unit 37 to specify a height $H_C$ from the detector 24, as shown in FIG. 1. For example, if it is known that the height of the object OB put on the conveyor's belt (not shown) in the height direction (the Y-axis direction) in FIG. 1 is $H_{OB}$ or more, the section at the height $H_C$ approximately equal to the center of the object OB in the height direction may be designated. Of course, in this example, the detection unit 26 is located under the conveyor's belt, so that the height $H_C$ is designated by taking it account a gap between the conveyor's belt and the detection surface of the detector 24 of the detection unit 26. In cases where the height of the object is unknown or has irregularities, the height $H_C$ may be set to be equal to the upper surface of the conveyor's belt. Alternatively, at the entrance of the conveyor's belt, there can be provided with a device for sensing the height of the object OB, which is for example an optical device, thereby providing height information.

Meanwhile, in automatically designating the section of the object OB, the specified information indicating a section at step S5 is not for the height $H_C$, but is for setting an all-pixel focused plane in an image along which is focused pixel by pixel. In this case, the height of the all-pixel focused plane is not always constant (flat), and irregular, in many cases, where the height intersects with the object OB but, when seen finely, the pixels may have different heights, on account of being optimally focused at each pixel. The scheme for producing the all-pixel focused plane is exemplified by for example U.S. Pat. No. 8,433,033 and PCT/JP2010/62842. The scheme according to such exemplifications uses a laminography (or called a tomosynthesis technique).

After this setting of the section, the data processor 35 produces a tomographic image at the designated section, by using a plurality of frame data $FD_{all}$ derived from the all energy range $Bin\_{all}$, for instance (step S6).

This image production is performed such that, if a constant height $H_C$ has been designated, the plurality of frame data $FD_{all}$ are overlapped on one the others and subjected to pixel value addition at the respective pixels, with being shifted by a shift amount corresponding to the height $H_C$ after each addition, which are main processes in the laminography. This way produces a tomographic image (a laminography image) $IM_{all}$ whose optimum focusing height position is fixed to the designated height $H_C$ (refer to FIG. 7). Though being limited to the height $H_C$ in the focusing height position, this image $IM_{all}$ is one type of focused images.

Figure 7:
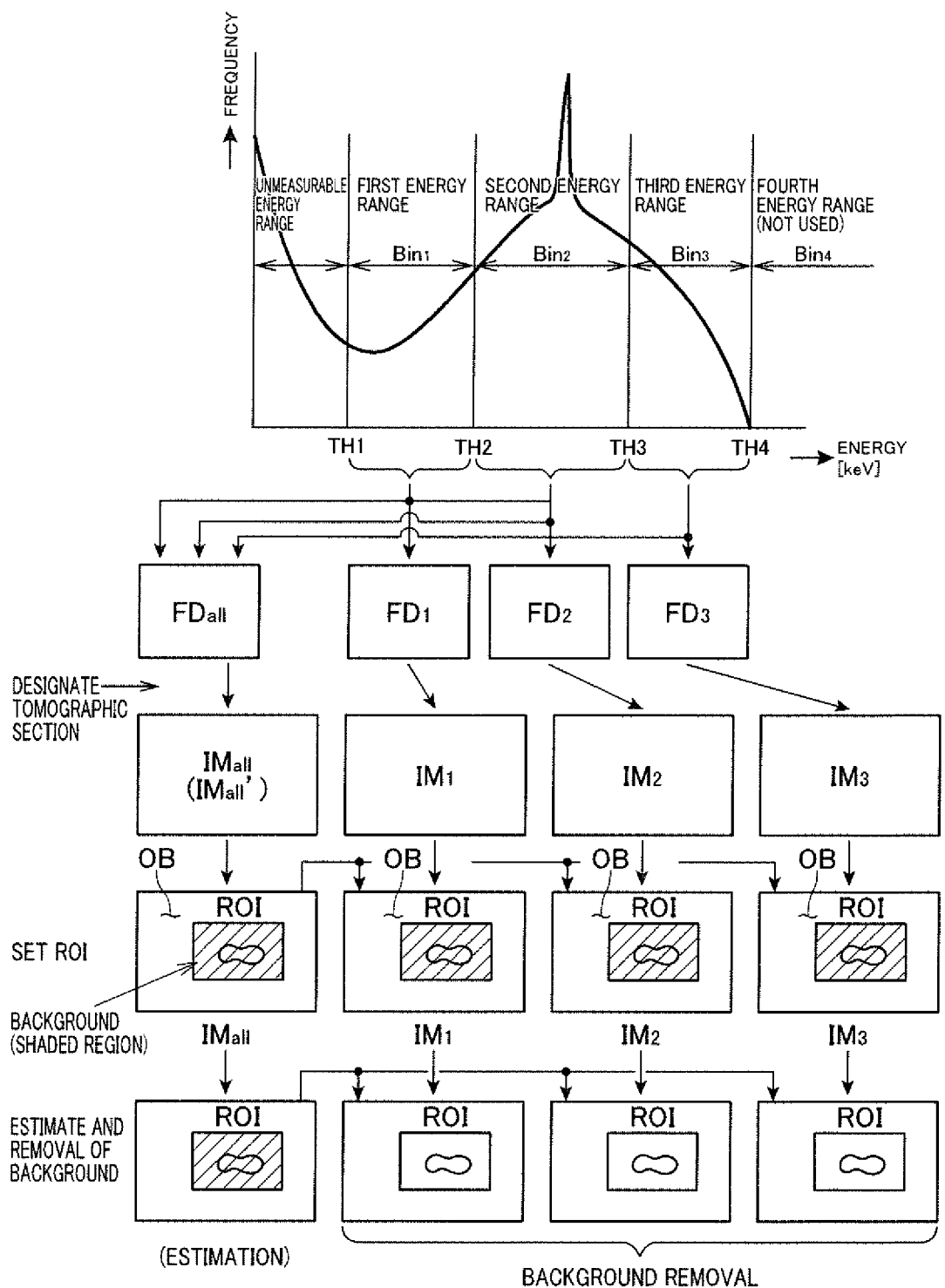
FIG. 7 is an illustration explaining pre-processing for the substance identification performed by the data processor.
Figure 10:
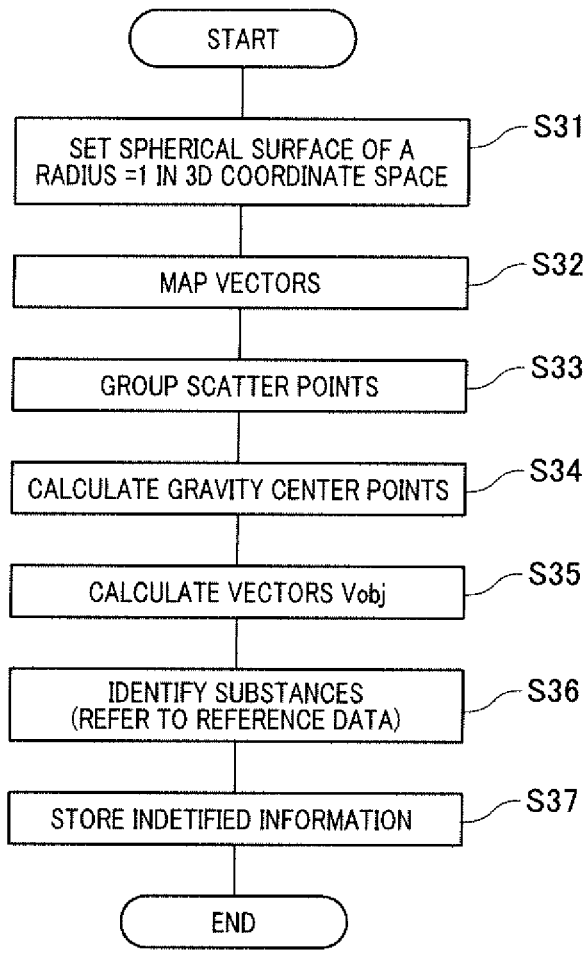
FIG. 10 is an outlined flowchart explaining a process performed in stages from generation of a three-dimensional scatter diagram to presentation of identified information in the first embodiment.

Alternatively, when setting of an all-pixel focused plane of the object OB is ordered, a plurality of frame data $FD_{all}$ derived from, for example, the all energy region $Bin_{all}$ among the collected frame data are used to produce an all-pixel focused image $IM_{all}'$ in the laminography technique (refer to FIG. 7). The object OB is depicted in this all-pixel focused image $IM_{all}'$, which is a tomographic image optimally focused pixel by pixel in the height direction or the X-ray radiating direction. This tomographic image is exemplified in U.S. Pat. No. 8,433,033 and PCT/JP2010/62842, in the same production as described before. These known publications show examples of dental applications, and, by converting a pseudo three-dimensional curved image produced according to these known techniques to a two-dimensional image, the converted two-dimensional image is available in the present embodiment as a two-dimensional focused tomographic image. This two-dimensional tomographic image is finer in focusing levels than the focused image $IM_{all}$ obtained at the constant (flat) height described before, thanks to the focusing process applied to each pixel. Any type of focused image is usable in the present embodiment, so that, in the following, the foregoing various focused images are simply referred to as a focused image $IM_{all}$. Alternatively, in the present embodiment, a two-dimensional image may be used instead of the foregoing two-dimensional image obtained by using an X-ray flat panel detector, as explained before.

The data processor 35 then uses the frame data $FD_1$, $FD_2$, $FD_3$ acquired in the three energy ranges Bin1, Bin2 and Bin3 to consecutively produce tomographic images with the laminography technique, where the tomographic images are made at the designated height $H_C$ or an average height of, for example, the all-pixel focused plane (steps S7, S8 and S9). By this, as pictorially shown in FIG. 7, three focused images $IM_1$, $IM_2$ and $IM_3$ are reconstructed for the three energy ranges. These three focused images $IM_1$, $IM_2$ and $IM_3$ can be reconstructed in any sequential order. Of course, these three focused images $IM_1$, $IM_2$ and $IM_3$ can be produced as all-pixel focused images which have been explained.

[Setting Region of Interest]

Then, on the all-pixel focused image $IM_{all}$, the data processor 35 sets a region of interest ROI automatically or interactively with the user (step S10). For example, when it is desired to identify the type of a substance composing the object OB, the region of interest ROI is set to have an appropriate size which can encircle an area of the object OB in the focused image $IM_{all}$, on the assumption that the area is composed of only the same type of substance(s). The thickness of such area may be changed positionally. On the other hand, in detecting foreign matters or identifying a lesion, the region of interest ROI is set to have a size which can encircle a doubtful area for foreign matters or a medically interceded area (refer to FIG. 7).

When the region of interest ROI has been decided on the all-pixel focused image $IM_{all}$, information indicative of this region is used to set this region of interest ROI on each of the three focused images $IM_1$, $IM_2$ and $IM_3$ in the same way as above (refer to FIG. 7).

[Estimation and Deletion of Background]

Then, on the focused image $IM_{all}$, the data processor 35 estimates pixel components (background components) which compose a background of the region of interest ROI (step S11). These background components depend on what kind of information is desired to be identified, as explained. In identifying or determining the type(s) or properties of a substance(s), the background components are known components of carrying means including the conveyor's belt and the air, in many cases. In identifying (or estimating) the type(s) of foreign matters or states of a lesion, the background components include, in addition to the foregoing known components, components of the object OB itself. If the background components are known, a fixed value corresponding to such background components is subtracted from the pixel values forming the region of interest ROI on the three focused images $IM_1$, $IM_2$ and $IM_3$ for the respective energy ranges (step S12).

In contrast, if amounts of the background components are unknown, it is necessary to estimate the amounts thereof. As this estimation technique, appropriate techniques, such as an interpolation technique which uses values of pixels at mutually separated plural locations outside the region of interest, can be employed.

The foregoing pre-processing is mainly intended to set the region of interest ROI on each of the focused images $IM_1$, $IM_2$ and $IM_3$ obtained from the three energy ranges and remove the background components from those images. It is therefore possible to perform the preprocessing with any of the focused images $IM_1$, $IM_2$ and $IM_3$, in place of producing the all-pixel focused image $IM_{all}$ obtained from all the energy ranges.

[Main Process for Substance Identification]

After the preprocessing, the data processor 35 perform a main process for the substance identification (step S13). This main process is shown in FIG. 8.

[Calculation of Linear Attenuation Value μt]

First, in the data processor 35, values of pixels which are encircled by the region of interest ROI on the three focused images $IM_1$, $IM_2$ and $IM_3$ and from which the background components are removed are used to linear attenuation values pt (step S131 in FIG. 8). The symbol μ indicates a linear attenuation coefficient (simply referred to as an attenuation coefficient) of a substance and the symbol t indicates the thickness of the substance along a radiation direction of X-ray beams transmitting through the substance.

Using the foregoing single-substance and plural-substance models, the linear attenuation value pt can be calculated, every pixel, in each of the energy ranges $Bin_i$ (i=1 to 3) on the basis of the following formulae.

$$\mu_i t = \ln Cl_i - \ln Co_i \quad (5)$$

$(i = 1 \text{ to } 3: \text{ in case of the single-substance model})$

[formula 1]

$$\sum_{j=a}^{n} \mu_{ij} t_j = \ln Cl_i - \ln Co_i \quad (6)$$

$(i = 1 \text{ to } 3, j = a \text{ to } n: \text{ in case of the plural-substance model})$ The symbol "ln" in the formulae shows the computation of natural logarithm.

From these formulae, it is understood that, if the number of photons which have entered a substance and the number of photons which have outputted therethrough are known, the linear attenuation value pt can be calculated. The number of outputted photons, $Co_i$, is detected, pixel by pixel, as the number of photons by the detector 24 in each of the energy ranges. The symbol, $Cl_i$ indicates the number of incidence photons under the same conditions as those in actual X-ray examinations, and is a known value which will can be preset. Of course, when necessary, the number of incidence photons, $Cl_i$, can be estimated for the substance identification, with consideration for differences in actual X-ray conditions.

In the medical examinations, soft tissue of human breasts or limbs may be regarded as being composed of substances which can structurally be simplified. Moreover, devices for pressing or fixing a human part being imaged in the examinations are plate-shaped, with the result that the linear attenuation value pt can be calculated accurately. Similarly, in the nondestructive inspections for food or other items, as long as it is possible to estimate the background components as described above, the linear attenuation value pt can be calculated accurately based on information of pixels from which the background components were removed.

Then, from each of the focused images $IM_1$ to $IM_3$ for the foregoing three energy regions Bin1 to $Bin_3$, the data processor 35 extracts the linear attenuation values μt of the respective pixels composing the region of interests, ROI, and vectorize the extracted values (step S132: refer to FIG. 8).

Practically, the data processor 35 produces a three-dimensional linear attenuation vector ($\mu_1 t$, $\mu_2 t$, $\mu_3 t$) for each of the pixels in each of the region of interests (refer to FIG. 9). Since the three-dimensional linear attenuation vectors ($\mu_1 t$, $\mu_2 t$, $\mu_3 t$) still include factors showing the thickness t and the density, these vectors themselves only show X-linear attenuation amounts derived from such thickness t and the density, not showing indexes inherent to a substance(s). The reason is that, similarly to X-ray scanogram or simply X-ray radiography, the thickness is an unknown factor in the ordinary condition, so that linear attenuation coefficients $\mu_1$, $\mu_2$ and $\mu_3$ inherent to a substance cannot be obtained. Even more, a single three-dimensional linear attenuation vectors ($\mu_1 t$, $\mu_2 t$, $\mu_3 t$) is not enough, because this vector is buried in noise components, whereby it is difficult to obtain information inherently identifying a substance.

With consideration such difficulties, the inventors have found that a substance(s) can be identified if the three-dimensional linear attenuation vectors ($\mu_1 t$, $\mu_2 t$, $\mu_3 t$) are normalized and treated as a group of such vectors.

Practically, the respective three-dimensional linear attenuation vectors ($\mu_1 t$, $\mu_2 t$, $\mu_3 t$) are normalized into unit lengths (having a length of 1) according to the following formula (7), thus producing three-dimensional mass attenuation vectors ($\mu_{1m}$, $\mu_{2m}$, $\mu_{3m}$) which exclude the factors of both thickness t and density (step S133).

$$(\mu_{1m}, \mu_{2m}, \mu_{3m}) = (\mu_1 t, \mu_2 t, \mu_3 t)/((\mu_1 t)^2 + (\mu_2 t)^2 + (\mu_3 t)^2)^{1/2} \quad (7)$$
$$= (\mu_1, \mu_2, \mu_3)/(\mu_1^2 + \mu_2^2 + \mu_3^2)^{1/2}$$

As a matter of fact, this normalization is to equalize the lengths of the respective three-dimensional mass attenuation vectors ($\mu_{1m}$, $\mu_{2m}$, $\mu_{3m}$), so that the equalized length is not limited to 1, but any length can be adopted. Incidentally, the symbol p indicates the linear attenuation coefficient provided before the normalization, while the symbol $\mu_m$ indicates the linear attenuation coefficient obtained by the normalization. Incidentally, in the attenuation coefficients $\mu_m$ shown in FIG. 11 indicate components (coefficients) of the normalized three-dimensional mass attenuation vectors ($\mu_{1m}$, $\mu_{2m}$, $\mu_{3m}$), which are referred to as mass attenuation coefficients in the present embodiment.

Thus, by the normalization, the factors of both thickness t and density can be deleted from the coefficients, so that the respective mass attenuation vectors ($\mu_{1m}$, $\mu_{2m}$, $\mu_{3m}$) can be presented in a three-dimensional coordinate system such that start points of the respective vectors are put at the coordinate origin (step S134). The three mutually orthogonal axes of this coordinate system are respectively assigned to the linear attenuation coefficients $\mu_{1m}$, $\mu_{2m}$, and $\mu_{3m}$. Hence, the coordinate positions of end points of such respective vectors, that is, gradients of such vectors in three-dimensional coordinate, indicate information inherently indicating a substance(s) (i.e., information showing the type(s) and/or property(s) of substance(s)).

In the present embodiment, in this way, the vectors showing the X-linear attenuation are treated as the linear attenuation vectors (pit, $\mu_2 t$, $\mu_3 t$) before the normalization, and treated as the mass attenuation vectors ($\mu_{1m}$, $\mu_{2m}$, $\mu_{3m}$) after the normalization. In the present embodiment, the information about these vectors is processed three-dimensionally, but may also be processed two-dimensionally.

The process at step S134 is performed in the order shown in FIG. 8, as an example. That is, mutually-orthogonal three-axis coordinate data corresponding to the mass attenuation coefficients $\mu_{1m}$, $\mu_{2m}$, $\mu_{3m}$, which are previously stored in the ROM 33, are read for producing display space (step S134-1), and a partial spherical surface passing each of the three axes at a length of 1 is set in a memory space (step S134-2). Then, one end of each of the respective three-dimensional mass attenuation vectors ($\mu_{1m}$, $\mu_{2m}$, $\mu_{3m}$) is arranged at the coordinate origin, while the other end, i.e., the tip, of each the vectors ($\mu_{1m}$, $\mu_{2m}$, $\mu_{3m}$) is arranged (dotted or mapped) at an intersecting point with the partial spherical surface (step S134-3).

The three-dimensional gradient information of the three-dimensional mass attenuation vectors ($\mu_{1m}$, $\mu_{2m}$, $\mu_{3m}$), which is replaced by the normalizing formula (7) at each pixel, changes depending on types and/or characteristics of substances in the three-dimensional space. Thus, this three-dimensional gradient information can also be interpreted as scatter data of energy corresponding to information inherent to the substances, i.e., inherent information, in a pseudo (virtually) way. By the inventors, the positions pointed by the tips of the three-dimensional mass attenuation vectors ($\mu_{1m}$, $\mu_{2m}$, $\mu_{3m}$), i.e., a map of pieces of information (practically the scattering points) showing the gradients of such vectors is also called a three-dimensional scatter diagram. In other words, depending on substances, the gradients of the three-dimensional mass attenuation vectors ($\mu_{1m}$, $\mu_{2m}$, $\mu_{3m}$) change, whereby three-dimensional positions (i.e., positions of scattering points) pointed by the vector tips also change. Information of such three-dimensional positions of the vectors reflect energy distributions of the X-ray photons.

In addition, the data processor 35 calculates the lengths of the respective three-dimensional linear attenuation vectors ($\mu_1 t$, $\mu_2 t$, $\mu_3 t$) for each pixel, according to the following formula.

$$((\mu_1 t)^2 + (\mu_2 t)^2 + (\mu_3 t)^2)^{1/2} \quad (8)$$

The amounts rendered by this formula indicate absorption amounts of X-rays which have not been transmitted through a substance, through which part of the X-rays has been transmitted through. In other words, such amounts according to this formula (8) shows a physical amount which depends on the length of each of the X-ray paths transmitted in the object (which can be referred to as a thickness of the object along each X-ray path). Since such absorption amounts include the factor of liner attenuation coefficients μ, the amounts can indicate the type or property of a substance, except that scalar values calculated on the formula (8) become coincidentally equal to each other. From this point of view, the absorption amount is associated with the inherent information and is able to function as information including a factor still indicative of the type or property of the substance. Accordingly, the absorption amount calculated by the formula (8) for every detector pixel becomes information associated with (or supplementing) the inherent information, thus still be used to indicate the type or property of the substance in almost all examinations and diagnoses. Image data composed of the absorption amounts can be alternatives to the conventional absorption images.

Hence, there is an image produced whose pixel values are given by graduating the absorption amounts of the X-rays which have not been transmitted (step S135). By the present inventors, the lengths of the three-dimensional mass attenuation vectors are referred, in a pseudo (or virtual) way, to as "absorption vector lengths", which correspond to X-ray attenuation amounts. An image whose pixel values indicate the absorption vector lengths is referred to an "absorption vector length image (or a pseudo absorption image when referring to a conventional absorption image)". This absorption vector length image is not easily dependent on shapes of X-ray incidence energy spectrums, thus providing stable images and reflecting the linear attenuation values pt as a whole. In consequence, the absorption vector length image provides higher contrast. This absorption vector length image can be stored in the image memory 36, and can be displayed by the display unit 38 when needed. In particular, by this absorption vector length image, distinguishing images are provided to a substance having a larger mass with larger X-ray beam hardening.

Figure 6:
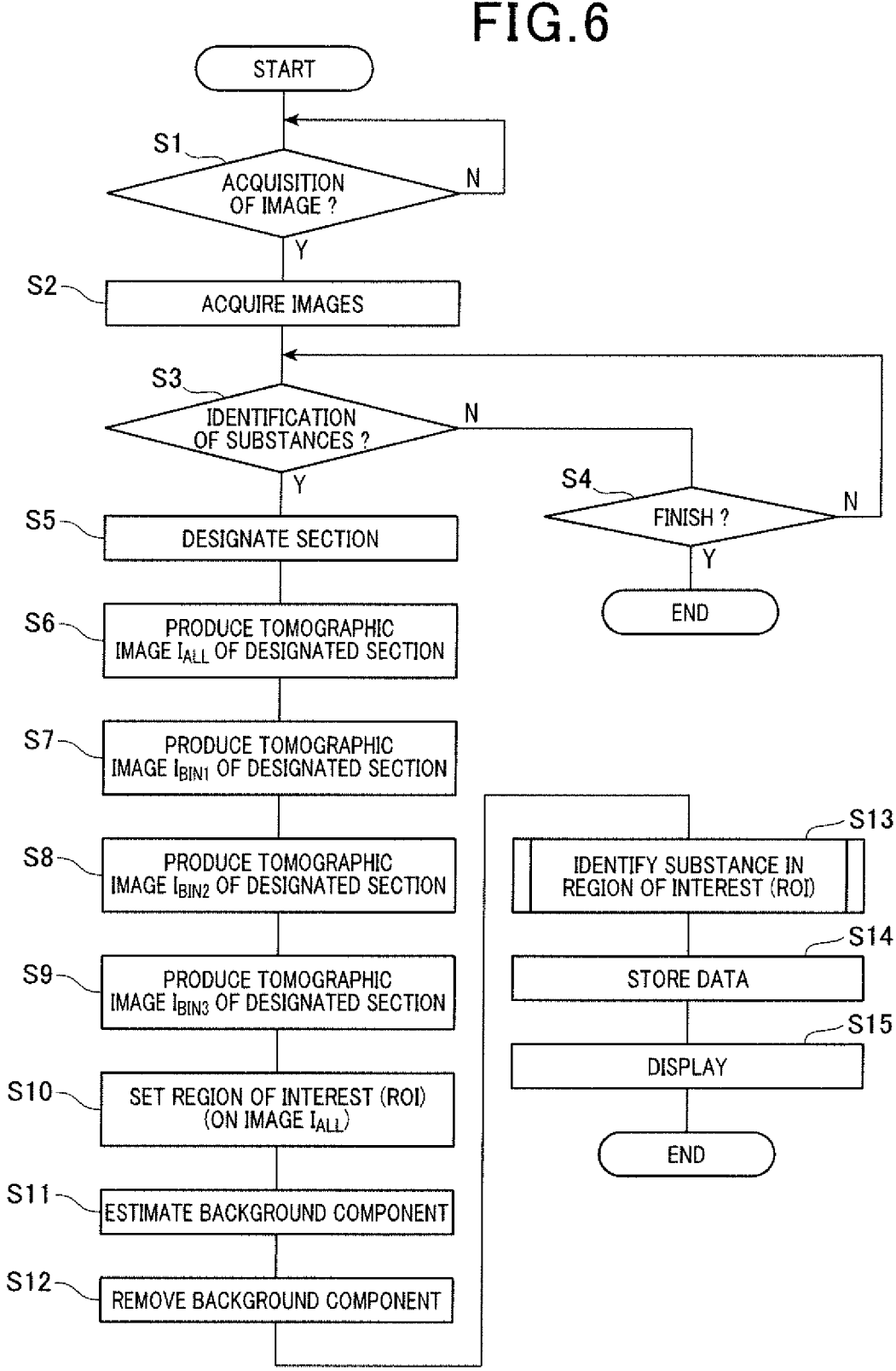
FIG. 6 is a flowchart outlining processing for substance identification and pre-processing thereof, which are performed by a data processor.

Finally, the data processor 35 stores, into the image memory 36, data of the foregoing three-dimensional scatter diagram as information inherent to the substance (in respect to the type or property thereof), and data of the absorption victor length image as associated information (or complementary information) associated with the inherent information for the substance identification (FIG. 6, step S14). On command, such images are presented to a user via for example the display unit 38 (step S15).

Accordingly, based on the X-ray photon counts for each of the respective energy range, which are detected by the photon counting detector 24, information inherently identifying an object can be obtained, regardless of being how large the thicknesses of objects OB are. This operation can provide greater advances if combined with display and/or analysis of the substance inherent information.

[One Example of Display and Analysis of Substance Inherent Information]

The display and analysis of this substance-inherent information are carried out as one step in step S15, for example. The data processor 35 responds to instructions from a user, for example, to present the foregoing substance-inherent information. Practically, a spherical surface of a radius 1 is set in the three-dimensional coordinate system whose three axes are assigned to the normalized linear attenuation coefficients $\mu_1$, $\mu_2$ and $\mu_3$ (refer to FIG. 10, step S31).

A three-dimensional scatter diagram composed of the three-dimensional mass attenuation vectors ($\mu_{1m}$, $\mu_{2m}$, $\mu_{3m}$) for the respective pixels is displayed in the three-dimensional coordinate space, where the vectors start from the origin of the coordinate system and the ends of the vectors are arranged (dotted or mapped), for example, on the signal spherical surface (whose radius is normalized as the radius of 1). The mapped end points on the spherical surface are aggregated based on substance-inherent information, thus providing aggregations (or gathering) of the scattering points inherent to the substance(s). Hence, even if a substance is assigned to an object, whose thickness t changes among some or all the pixel positions, the scattering points are aggregated independent of the factor of the thickness t.

Figure 11:
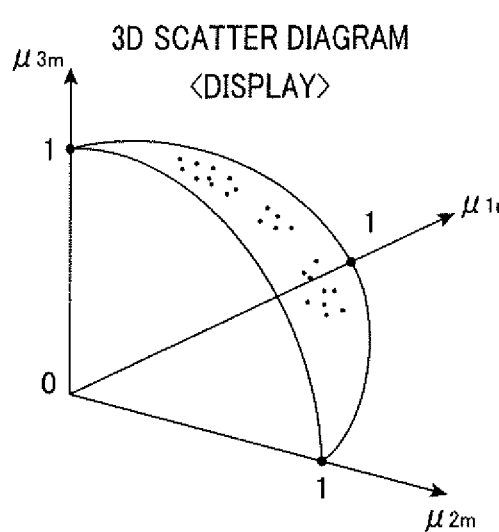
FIG. 11 is a perspective view pictorially explaining a normalized three-dimensional scatter diagram.

FIG. 11 pictorially shows an example in which the groups of the scattering points are mapped on part of a normalized spherical surface (the part of the same single surface) as three-dimensional scatter diagrams.

As shown in FIG. 12(A), the data processor 35 then groups the scattering points (refer to dotted-lines: step S33), and as shown in FIG. 12(B), calculates the positions of the center of gravity GR of the grouped scattering points (step S34). Then, as shown in FIG. 12(C), the data processor 35 calculates vectors Vobj each connecting the origin and each of the positions of the center of gravity GR derived from the respective scattering point groups (step S35).

The data processor 35 then compares the vectors Vobj with predetermined and preset reference data to identify or determine the type and/or properties of a substance(s) (step S36). The reference data include a memory table, for example, in which three-dimensional gradients of the vectors Vobj are memorized together with their allowances, which gradients were measured beforehand with changing various types and/or properties of reference substances. Accordingly, when it is determined whether each of the calculated vectors Vobj falls into the allowances, the substance(s) can be identified in its type and vector information which is noise is excluded as well. The identified information is preserved (step S36).

Incidentally, at step S15 described, the three-dimensional scatter diagrams and the absorption vector length image can be presented and provided in other various modes. For example, the data processor 35 is able to display on the display unit 38 both the three-dimensional scatter diagrams and the absorption vector length image in a divided manner. In such a case, the three-dimensional scatter diagrams may first be displayed, and, responsively to a user's request, the absorption vector length image may be displayed auxiliary.

[Unique Image Display Process According to the Present Invention]

A unique image display process in the first embodiment will now be described.

This image display process is an image processing technique which is referred as contour line display of a scatter diagram by the present inventors. This process technique will now be described with reference to FIG. 13 to FIG. 19.

First of all, the data processor 35 reads from, for example, the image memory 36, data indicative of the vectors at the respective pixels calculated at step S132 or S133 in FIG. 8 described already. Namely, such vectors are the three-dimensional linear attenuation vectors ($\mu_1 t$, $\mu_2 t$, $\mu_3 t$) obtained before the normalization or the three-dimensional mass attenuation vectors ($\mu_{1m}$, $\mu_{2m}$, $\mu_{3m}$) obtained after the normalization. In the present embodiment, these two types of vectors are represented by the before-normalized three-dimensional linear attenuation vectors ($\mu_1 t$, $\mu_2 t$, $\mu_3 t$).

Figure 14:
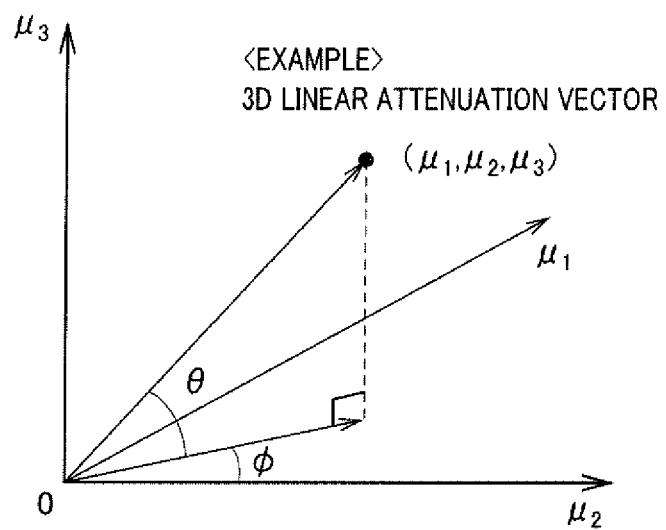
FIG. 14 is an illustration explaining one step in the image process in the first first embodiment.

The three-dimensional linear attenuation vectors ($\mu_1 t$, $\mu_2 t$, $\mu_3 t$) the respective pixels are three-dimensionally displayed as shown in FIG. 14. The data processor 35 thus proceeds to dissolve the three-dimensional vectors into corresponding arguments $\theta$ and $\phi$, for every pixel, and produce data displayed in the polar coordinate (step S42). Hence, by this production, the dimension of the thickness t is removed from the polar-coordinate display data. The resultant polar-coordinate display data ($\theta$, $\phi$) are displayed on the display unit 38 (step S43), as exemplified in its display in FIG. 15.

The data processor 35 then determines, in an interactive manner, whether or not the user desires to observe the currently displayed image on the display unit 38, that is, a two-dimensional spread of scattering points displayed as the polar-coordinate data (θ, φ) (step S44). When this determination is YES, the processing is made to wait for the next user's command (step S45). In contrast, when it is determined to be NO at step S43, the data processor 35 sets grid-shaped regions $ROI_{div}$ (i.e., a region of interest) in response to a user's command (step S46; refer to FIG. 16). These grid-shaped regions, ROI, are intended to re-count a two-dimensional spread of the scattering points into a plurality of predetermined regions which are divided into finer shapes and sizes, so that the divides sizes and shapes can be set to be arbitrary.

The data processor 35 then collects, every one of the plurality of regions $ROI_{div}$, the number of scattering points H classified into the respective regions $ROI_{div}$ and temporarily stores the counted numbers H in the image memory 36 (step S47). Then the data processor 35 reads, from the image processor 36, the collected numbers H (i.e., the number of scattering points at each region (functioning as added information)), and, as pictorially shown in FIG. 17, maps the two arguments θ and φ and the collected numbers H assigned to the axes of the three-dimensional coordinate system (step S48). The data processor 35 calculates contour lines on the collected numbers H (step S49), and displays the calculated contour lines on the display unit 38 (step S50). It is preferred that a smoothing process for the collected numbers H is involved in calculating the contour lines, thereby resulting in a reduction in statistic noise in the calculation of the contour lines.

Figure 17:
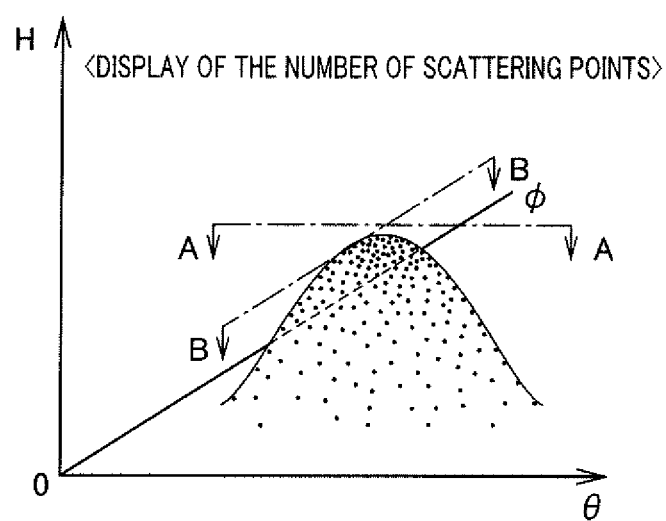
FIG. 17 is an illustration explaining one step in the image process in the first first embodiment.

As can be understood from (A) and (B) of FIG. 18, the three-dimensional representation of the height H is shown by pixel values whose intensities are dependent on the number H of scattering points respectively indicating the effective atomic numbers of compositions of the object OB, that is, the effective atomic numbers of one or more types of elements contained in the object OB. Hence, when contour lines are depicted, every width of designated intensifies, on this height representation (step S49), it is possible to provide a contour-line representation in the same way on the maps (refer to FIG. 19). When referring to these contour lines, the two-dimensional contour-line representation map has one or more peaks or spreads which are dependent on the number of scattering points (indicating the height information functioning as added information). Of course, in an actual application, these peaks or spreads become more complex based on types of elements (further, dependent on whether or not a foreign matter(s) is contained in the object) or the effective atomic numbers thereof. And the respective peaks indicate distributions (or spread area, aggregated area) of the scattering points which form a sharp peak(s) or a relatively flat plot area. FIG. 17 shows a simplified peak represented by the contour lines.

In this two-dimensional contour-line representation, the number of scattering points, H, becomes larger as approaching the peak of each spread or distribution, which indicates that the density of the composition having the same atomic number becomes higher. Hence, in most cases, if a composition (substance) having a higher density is found, it is possible to know the type or property of a region of interest of the object OB or a foreign matter which may be present in the object. If it can be assumed that one kind of substance which has only a particular atomic number is subjected to an examination and there is noise in the acquired X-ray transmission data, there can be provided only one sharp peak in this two-dimensional contour-line representation diagram. However, actual measurement systems involve noise and compositions having various atomic numbers, including air, are contained in an object, it is frequent that this complex diagram shows complex contour-line patterns corresponding to complex various patterns composed of the scattering points. It is also always true that objects being examined contain a plurality of elements, an effective atomic number is used as a representative for the atomic numbers of such elements.

Then, interactively with the user, the data processor 35 proceeds with the analysis of three-dimensional scattering states on the two-dimensional contour-line representation diagram, and then an analysis and identification of the types and/or properties of compositions (substances) composing the object OB (step S50). This analysis technique can be provided by various methods including comparing the obtained types and/or properties with reference scatter data obtained from reference objects, and calculating deviations among the peaks on the diagram. The analyzed and identified results are provided to the user by the display unit 38, for example (step S51).

Figure 15:
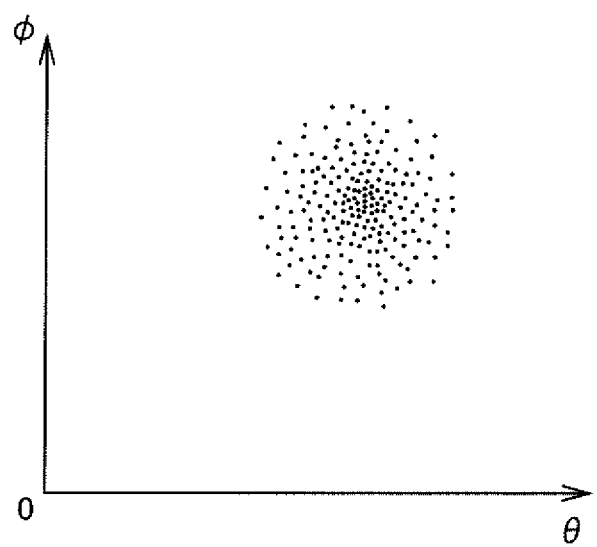
FIG. 15 is an illustration explaining one step in the image process in the first first embodiment.
Figure 16:
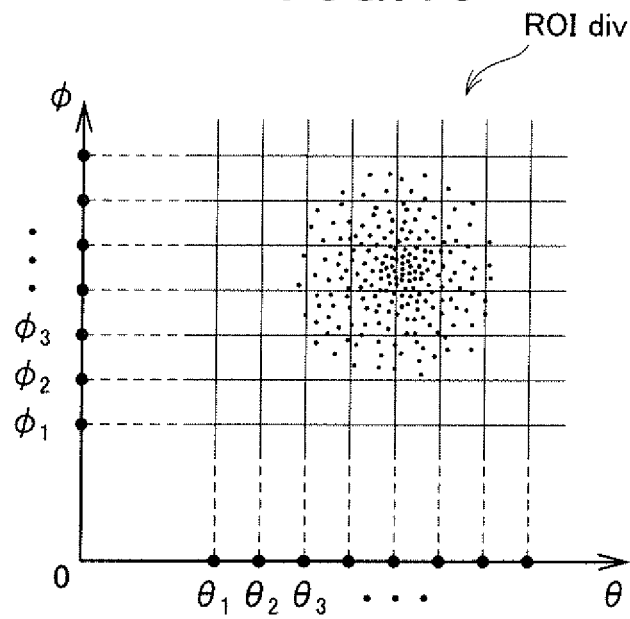
FIG. 16 is an illustration explaining one step in the image process in the first first embodiment.

Accordingly, in this first embodiment, it is possible to display, as the three-dimensional scatter diagram, the three-dimensional linear attenuation vectors ($\mu_1 t$, $\mu_2 t$, $\mu_3 t$) acquired at the respective pixels in a simpler manner, and how to display such vectors can be enriched in its variations. Particularly, this two-dimensional contour-line representation diagram has a big feature that the diagram is produced via a conversion to the two-dimensional argument data θ and φ, as shown in FIG. 15.

Figure 12:
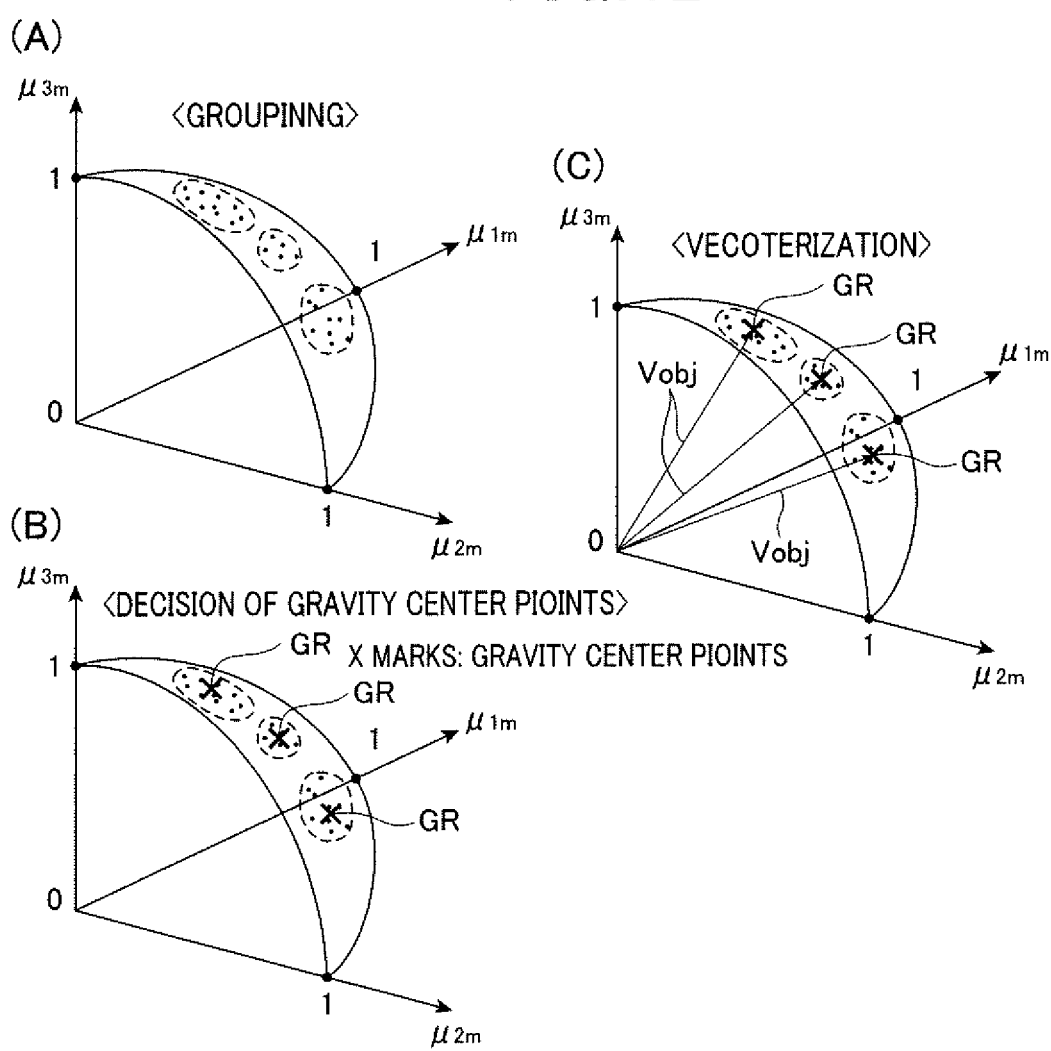
FIG. 12 shows perspective views explaining production of three-dimensional vectors from the three-dimensional scatter diagram, based on scattering points inherent to a substance
Figure 13:
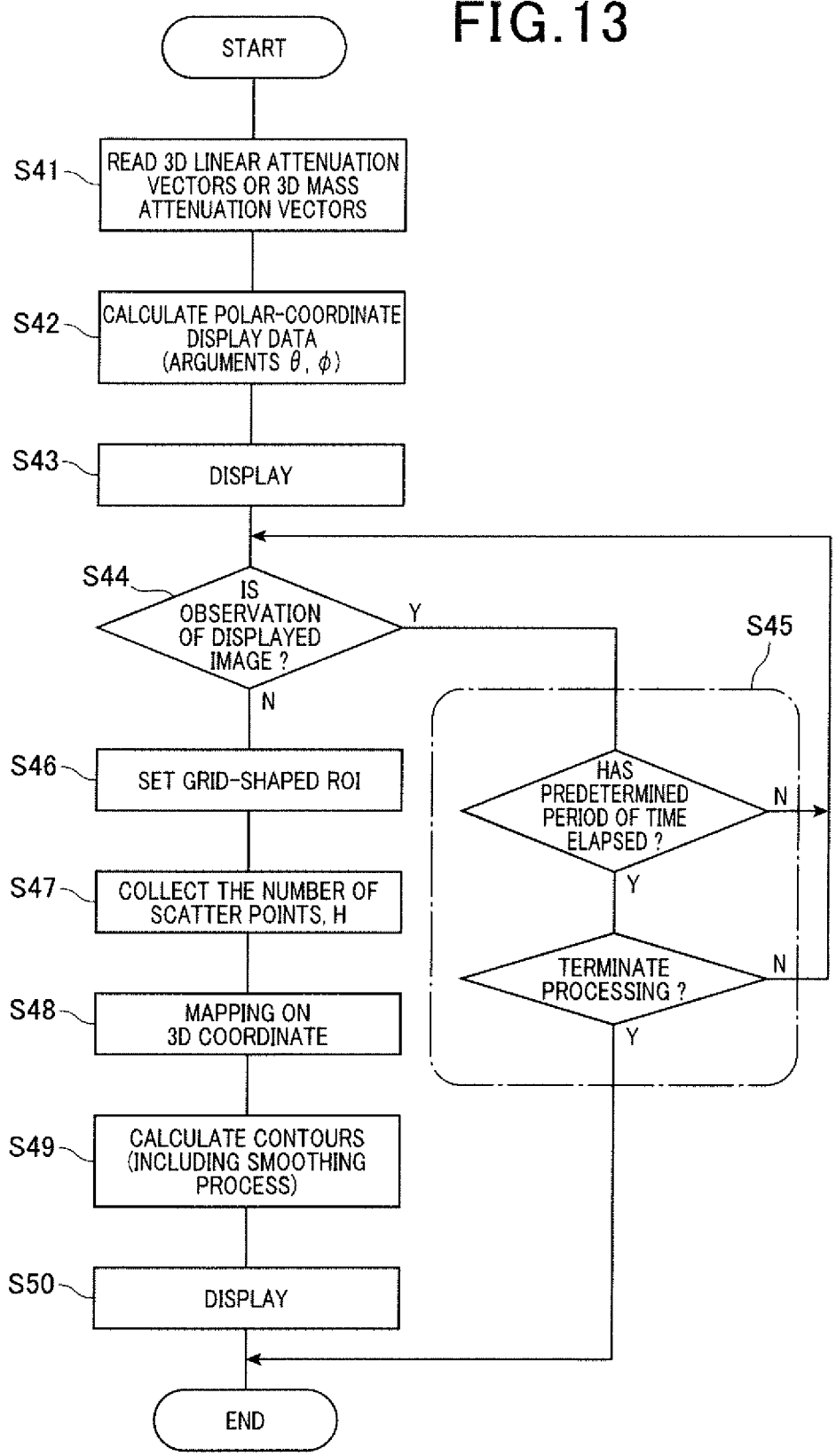
FIG. 13 shows a flowchart outlining an image process for substance indentation executed by the data processor employed in the first embodiment.

It is also a feature that the distributions of the two-dimensional argument data θ and φ are not affected by a position of an observer's view point in the three-dimensional scatter diagram (refer to FIGS. 11 and 12). This observer's view point means a perspective view point necessary in making three-dimensional or two-dimensional display data. Hence, with a consideration that it is desired to exclude dependency of how the scatter diagram is seen on view-point positions and directions when observing how the scattering points are distributed, the normalized image is displayed, leading to a steadier display in identifying a substance(s) and/or foreign matter(s) (i.e., substance(s)).

As a modification, the contour-line representation in the foregoing embodiment can further be developed. For instance, at step S49, it is possible to calculate data indicative of density display in which gray levels can be changed every designated density width. Alternatively, at step S49, it is still possible to calculate data give a height peak at a distribution area whose number of scattering points is the highest, for example, a color among the three primary colors, and gradations of a color(s) (or a hue(s)) to areas surrounding the central height peak. This provides gradation display based on color densities (hues). This is exemplified as part (A) of FIG. 19, in which, in addition to a simple contour-line exaggerated display, a diagram which details the widths of intervals between the contour lines, whereby the display is enriched in its variations.

Second Embodiment

A second embodiment still relates to the foregoing contour-line display of a scatter diagram, in which the process for the display is developed to involve a subtraction technique.

In the second embodiment and subsequent embodiments following the second embodiment, components which are the same or functionally equivalent as or to those in the foregoing first embodiment will be assigned to the same reference numerals and symbols explained in the first embodiment, whereby the explanations are simplified. This explanation will also true for the third embodiment and embodiments following the third embodiment. In the second embodiment and subsequent embodiment thereto, the processing will be executed automatically by the data processor 35 via default setting or interactively with a user.

With reference to FIGS. 20 to 26, a foreign-matter examination process which is for checking whether or not a foreign matter, such as a cockroach, is contaminated in a noodle pot will now be described.

Figure 20:
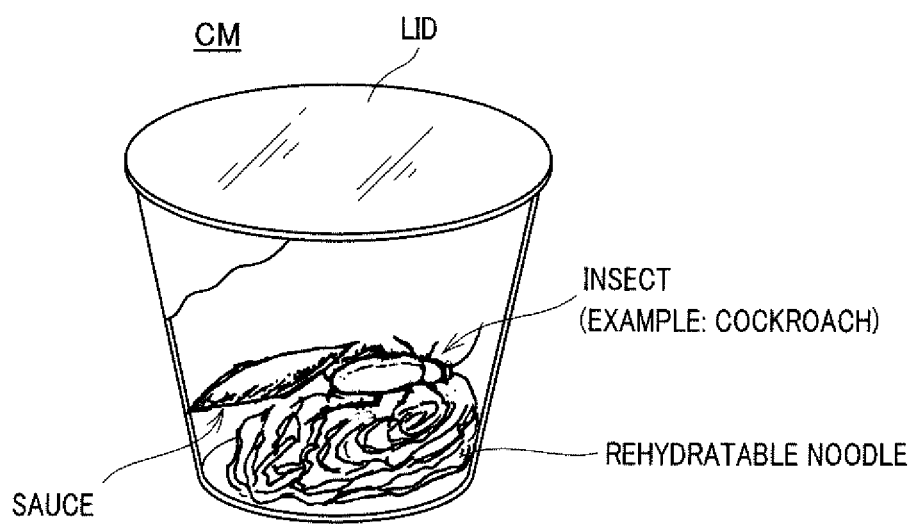
FIG. 20 is a pictorial illustration of a noodle pot exemplified as an object for a foreign matter inspection performed by the data processor in the second embodiment.

The present embodiment explains the X-ray examination system, shown in FIG. 1, which is used as an in-line type foreign-matter examining system. As shown in FIG. 20, a noodle pot CM, which can be commercially available, is put on the belt conveyer BT, during which time the data processor 35 equipped in the data processing apparatus 12 executes a foreign-matter examination process exemplified in FIG. 21, repeatedly every a preset period of time Δt.

Figure 21:
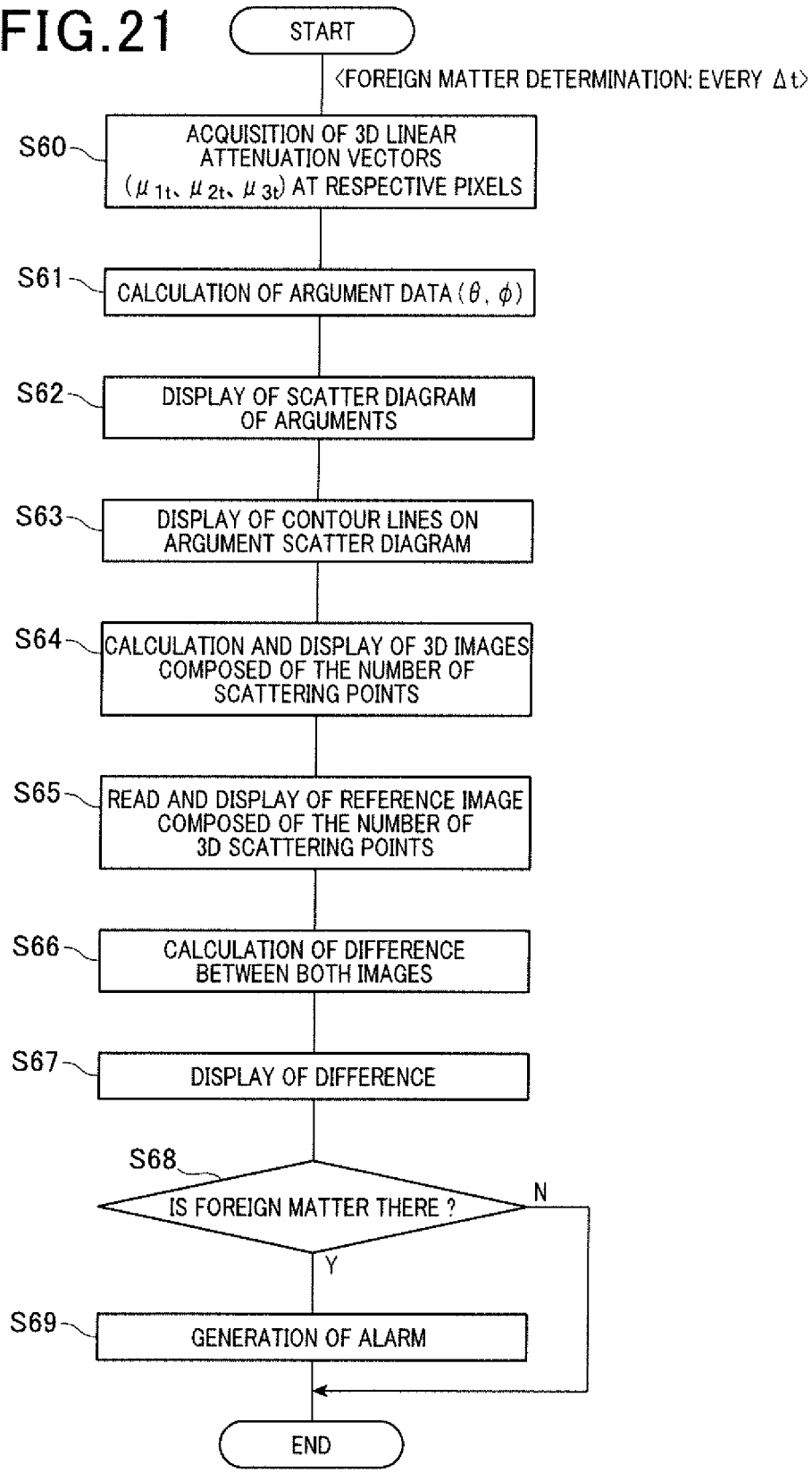
FIG. 21 is a flowchart outlining an image process for the foreign matter inspection in the second embodiment.

Similarly to that explained in the first embodiment, the data processor 35 acquires, every pixel, three-dimensional linear attenuation vectors ($\mu_1 t, \mu_2 t, \mu_3 t$) acquired by scanning the noodle pot CM (refer to FIG. 21, step S60). The data processor 35 then calculates two-dimensional argument data ($\theta, \phi$) from coordinate-system data showing the vector amounts, in the same manner as described before (step S61). As an instance, the noodle pot CM contains dried noodle and a flavoring sauce pouch.

Figure 22:
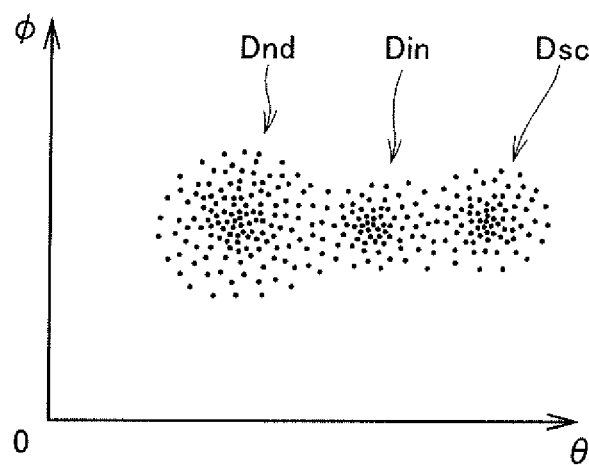
FIG. 22 is a diagram explaining one step of the image process in the second embodiment.
Figure 23:
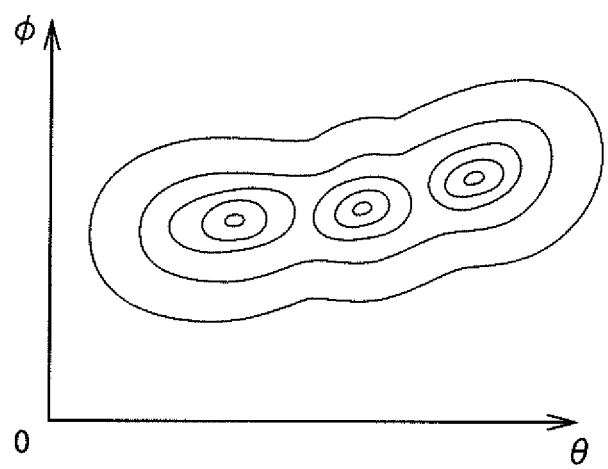
FIG. 23 is a diagram explaining another step of the image process in the second embodiment.
Figure 24:
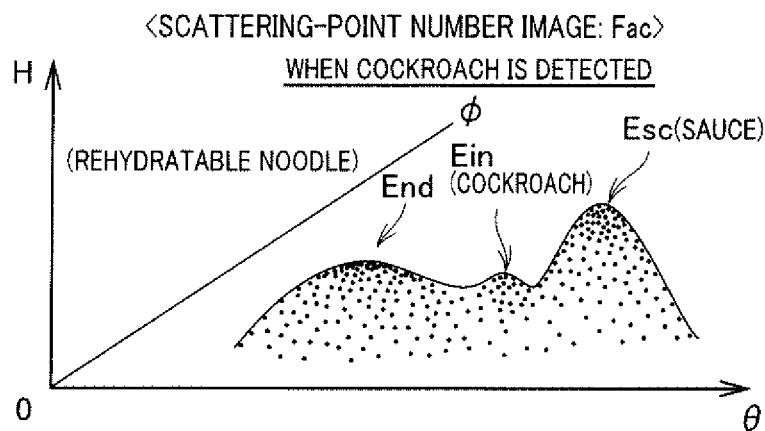
FIG. 24 is a diagram explaining another step of the image process in the second embodiment.

The two-dimensional argument data ($\theta, \phi$) are then displayed on the display unit 38 (step S62) so as to provide an argument-data scattering diagram image Fhen. In this image Fhen, as shown in FIG. 22, there appear a distribution Dnd resulting from the dried noodle and a distribution Dsc resulting from the sauce, as well as a distribution Din resulting from an inspect only if the insect is contaminated as a foreign matter in the pot. The distribution Din is located between both of the distributions Dnd and Dsc in the image. Then the data processor 35 calculates contour-line data of the pixel values of those distributions Dnd, Dsc, and Din and display the calculated distributions (step S63). By this step, a contour-line image Fto illustrated in FIG. 23 can be obtained. Based on this contour-line image Fto, a three-dimensional scattering-point number image is calculated and displayed (step S64), which has another dimension composed of the number of scattering points, H, measured every small area having a designated size on the image Fto. This provides a three-dimensional scattering-point number image Fac as illustrated in FIG. 24. As a modification, it is also possible that the three-dimensional scattering-point number image Fac as illustrated in FIG. 24 can be calculated directly from the argument-data scattering diagram image Fhen shown in FIG. 22 without being routed via the contour-line image Fto shown in FIG. 23, for the purpose of direct display.

Figure 25:
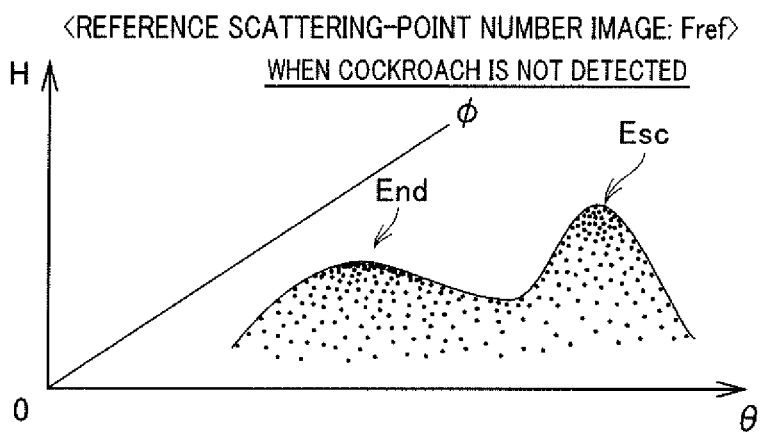
FIG. 25 is a diagram explaining another step of the image process in the second embodiment.

On the three-dimensional scattering-point number image Fac as illustrated in FIG. 24, displayed are the following: a contour-line distribution End indicative of the dried noodle, a contour-line distribution Esc indicative of the sauce, and a contour-line distribution Ein indicative of an insect which is a foreign matter in the pot. It is normal that the peak value and the spread of the contour-line distribution Ein indicating the insect are relatively smaller than those of the other distributions. The data processor 35 reads, from the ROM 33 or another memory device, preset and preserved data indicative of a reference scattering-point number image Fref into a work area thereof (step S65). This reference scattering-point number image Fref is obtained, as shown in FIG. 25, as a three-dimensional reference image which can be acquired via X-ray scanning from a normal noodle pot with no foreign matter, such as an insect, contaminated. That is, on the reference scattering-point number image Fref, a contour-line distribution End showing the dried noodle and a contour-line distribution Esc showing the sauce are depicted, which serve as normal reference data.

The data processor 35 calculates a mutual difference, every pixel, between the three-dimensional scattering-point number image Fac and the reference scattering-point number image Fref, which are shown in FIGS. 24 and 25 respectively (step S66). Since it is unknown before the examination that the noodle pots are contaminated with foreign matters, the foregoing difference calculation is sequentially, at a designated interval, and every pixel, applied to both images Fac and Fref obtained by X-ray scanning each of the noodle pots CM passing through the inspection space on the belt conveyor. A scattering-point number image Fdif resulting from the difference in calculation is also displayed (step S68).

Figure 26:
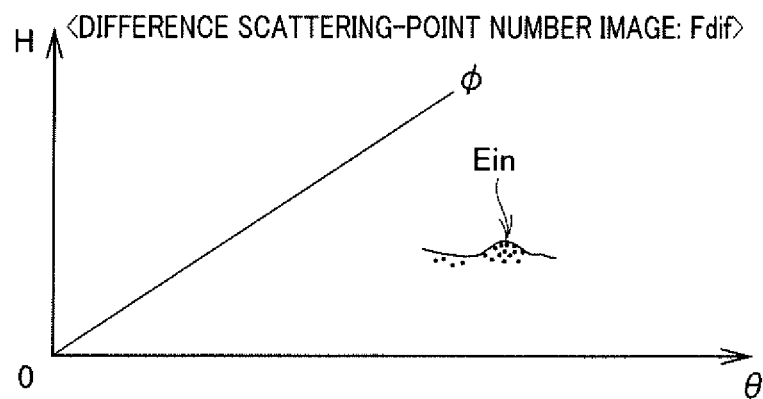
FIG. 26 is a diagram explaining another step of the image process in the second embodiment.

The data processor 35 then determines whether or not, in the scattering-point number image Fdif, there are a distribution Din resulting from an insect, whose number of scattering points, H, which are higher than a predetermined threshold (step S68). If there is an insect contained as a foreign matter in the noodle pot CM, only a contour-line distribution Ein showing the existence of the insect remain in the image Fdif, as shown in FIG. 26. Therefore, when the data processor 35 determines YES at step S68 (i.e., there is a foreign matter contaminated), the data processor commands issue of an alarm for the contamination (step S69). When it is determined that there is no contamination of such a foreign matter, the alarm will not be issued, thus returning the processing to the initial step.

In addition to the foregoing advantageous operations explained in the first embodiment, the present embodiment can provide the three-dimensional scattering-point number image Fdif by the difference in calculation. This image can easily capture small changes due to contamination of a foreign matter which is both minute in size and in an amount of X-ray absorption. Such changes are depicted independently of the position at which the foreign matter is contaminated in the noodle pot. This regard is advantageous over the conventional examination technique depending on local position-by-position changes of gray levels in an X-ray transmission image.

Third Embodiment

Figure 27:
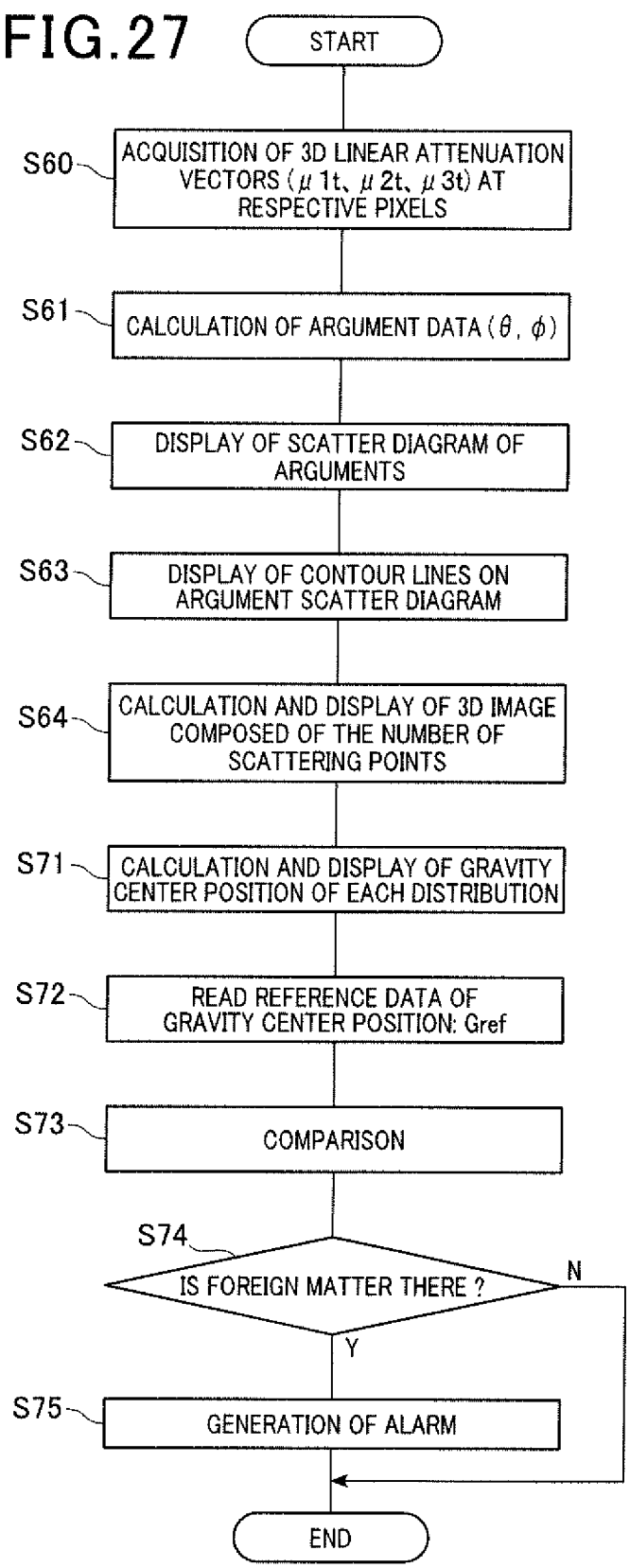
FIG. 27 is a flowchart outlining an image process for a foreign matter inspection performed in a third embodiment.
Figure 28:
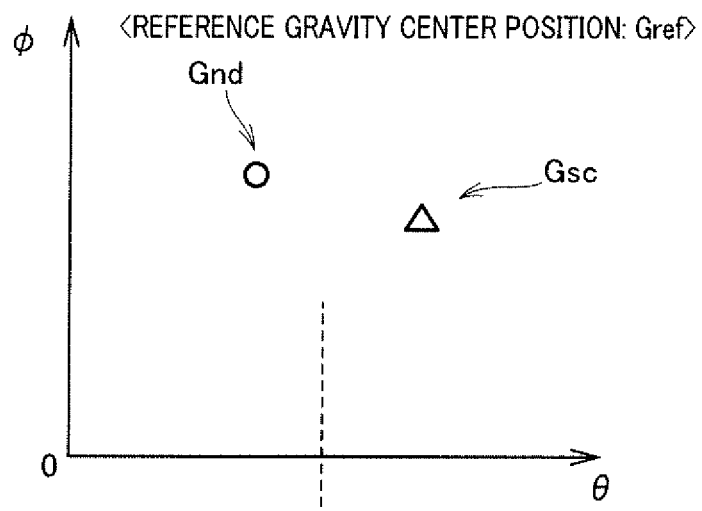
FIG. 28 is a diagram explaining one step of the image process performed by the data processor in the third embodiment.
Figure 29:
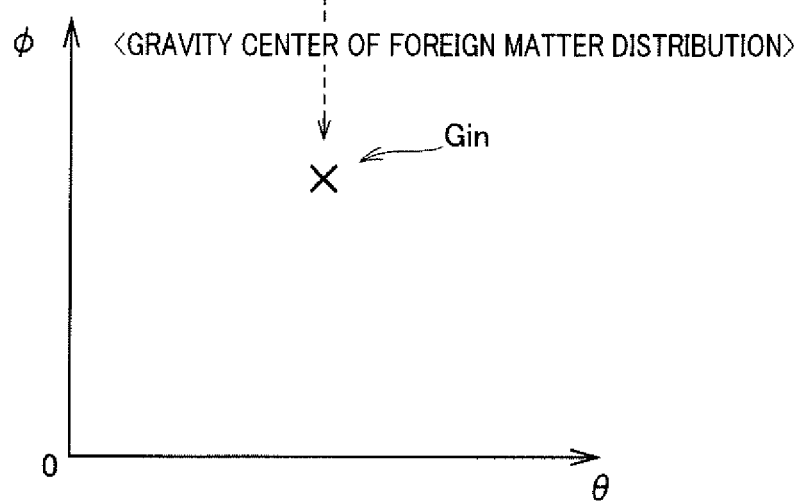
FIG. 29 is a diagram explaining another step of the image process in the third embodiment.

A third embodiment concerns with a technique provided by developing the process for the foregoing "contour-line display of scatter diagrams" to a gravity-center comparison technique. With reference to FIGS. 27 to 29, this developed technique will be now explained based on a foreign matter examination for the foregoing noodle pot.

A foreign-matter examination system capable of performing the foregoing technique is structured identically to that of the second embodiment. The data processor 35 is thus able perform the processes at steps S60 to S63 shown in FIG. 27 in the same way as those in FIG. 21.

Based on the contour-line image Fto obtained as step S63, The data processor 35 calculates the gravity center positions Gnd, Gsc, and Gin of the distribution Dnd indicative of the dried noodle, the distribution Dsc indicative of the sauce, and the distribution Din indicative of an insect when such an insect is contained as a foreign matter, which are supposed to be depicted in the image, and displays those gravity center positions on, for example, the contour-line image Fto (step S71). This distribution Din indicating an insect is carried out only when the insect exists in the noodle pot, but, at this stage, the data processor 35 cannot interpret that the distribution Din is generated due to existence of the insect.

The data processor 35 then reads from the ROM 33 predetermined and preset reference gravity-center position data Gref (step S72). As shown in FIG. 28, this data Gref functions as reference information obtained in the normal state where there is no foreign matter such as an insect within the noodle pot CM, and have a center gravity position Gnd for the noodle itself and a center gravity position Gscf of the sauce. After this, the data processor 35 compares the respective positions of the gravity centers on the contour-line image Fto with the reference gravity-center position data Gref by using mutual difference calculation (step S73), which makes the data processor 35 check whether or not the foreign matter is present (step S74). Hence, if an amount of the difference exceeds the allowable range that is set to the distribution Din for a foreign matter, which should not be found if the pot is normally packed (as illustrated in FIG. 29), it is recognized by the data processor that there is a foreign matter within the pot.

Then the processing continues, in the same way as described, to issuing an alarm to notice the presence of the foreign matter (step S75).

As a result, the present embodiment makes it possible to check presence of foregoing matters by using the relatively simpler process based on calculation of the gravity center positions of the respective distributions and comparison of such positions with the reference data.

Fourth Embodiment

Figure 30:
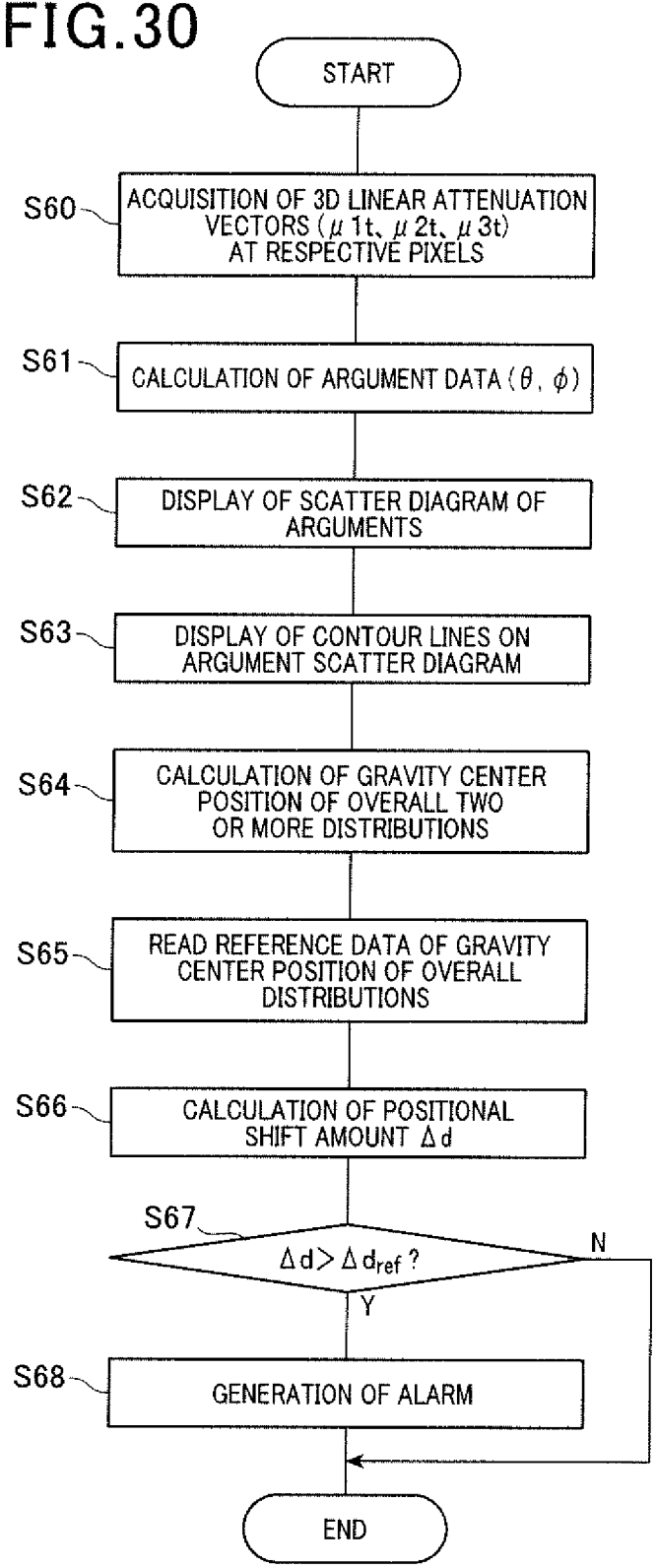
FIG. 30 is a flowchart outlining an image process for a foreign matter inspection performed by the data processor in a fourth embodiment.
Figure 31:
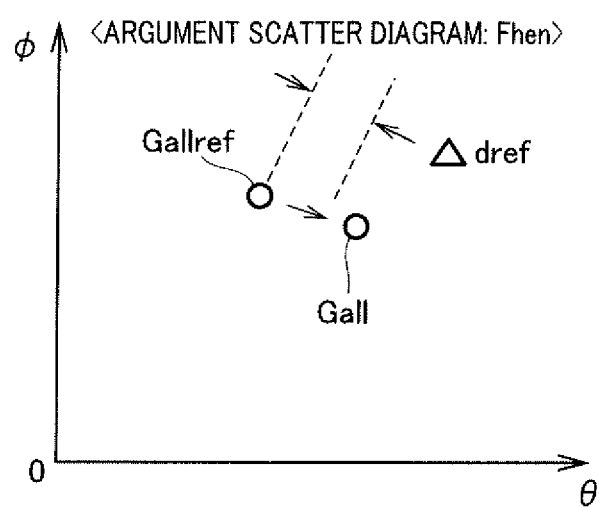
FIG. 31 is a diagram explaining one step of the image process in the fourth embodiment.

A fourth embodiment relates to a technique with which the process for the foregoing scatter-diagram contour-line display is developed to a process for a gravity-center comparison method, which simplifies the gravity-center method according to the third embodiment. With reference to FIGS. 30 and 31, and also using the structural components of the third embodiment, the fourth embodiment will now be described.

The data processor 35 will perform the processes at the foregoing steps S60 to S63 (refer to FIG. 30). The data processor 35 then proceeds to calculate the center gravity position $G_{all}$ of all of the plurality of distributions Dnd, Dsc, (Din) on the scatter diagram Fhen composed of the argument data $\theta$ and $\phi$ (step S64). By this calculation, as shown in FIG. 31 for instance, a single point $G_{all}$ is designated on the scatter diagram of the argument data $\theta$ and $\phi$. Then, in the same way as forgoing, a reference data $G_{allref}$ given for all the distributions obtained with no foreign matter are read the ROM 33, for example, in which such reference data are previously measured and stored in the ROM 33 (step S65: refer to FIG. 31). The actual gravity-center position Gall is positionally shifted by an amount of $\Delta d$ on the scatter diagram image Fhen, from the reference data $G_{allref}$, due to the presence of a foreign matter.

The data processor thus detects this positional shift amount $\Delta d$, and compares the detected positional shift amount $\Delta d$ with a preset threshold $\Delta d_{ref}$ (step S66 and S56). If this comparison shows $\Delta d > \Delta d_{ref}$, it is determined that there is a foreign matter contained and an alarm is issued (step S68).

In this way, the present embodiment is able to provide the same or similar advantageous operations as or to those in the previous embodiments.

Fifth Embodiment

A fifth embodiment exemplifies a modification which is provided by modifying the center-gravity comparison technique explained in the fourth embodiment.

In the foreign matter inspection, there are many cases where a foreign matter contained in an object being examined is smaller in size than the object or a foreign matter has an effective atomic number which is not so much different from that of the elements (i.e., tissues and/or elements having ordinal contrast due to the X-ray transmission) composing an object being examined. In such a case, it can be assumed that there is a case in which the positional shift amount $\Delta d$ detected in the foregoing fourth embodiment is small so that it is difficult to determined that the positional shift amount $\Delta d$ indicates presence of a foreign matter. In this fifth embodiment, by taking such a case into account, the gravity-center comparing method is provided. The hardware configuration in this embodiment is identical to that explained in the foregoing embodiments.

Figure 32:
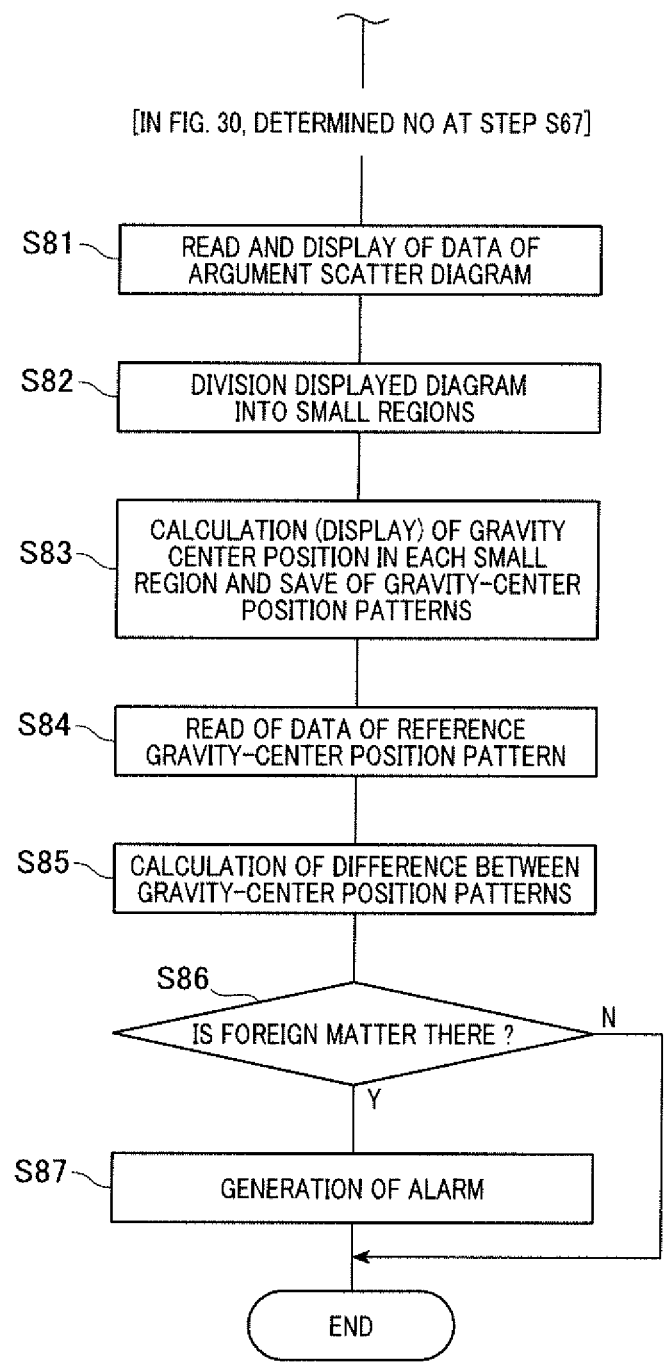
FIG. 32 is a partial flowchart outlining an image process for a foreign matter inspection performed by the data processor in a fifth embodiment.

In the foregoing process shown in FIG. 30, the data processor 35 proceeds to the process shown in FIG. 32 when it is determined to be $\Delta d \leq \Delta d_{ref}$ in step S67 (i.e., NO at step S67). That is, this determination of NO expresses no foreign matter contained in the object or even if being contained, the positional change amount $\Delta d$ of the gravity center is small due to the foregoing reason. Hence, if it is desired to conduct a foreign matter examination more accurately, the process shown in FIG. 32 can be performed.

Figure 33:
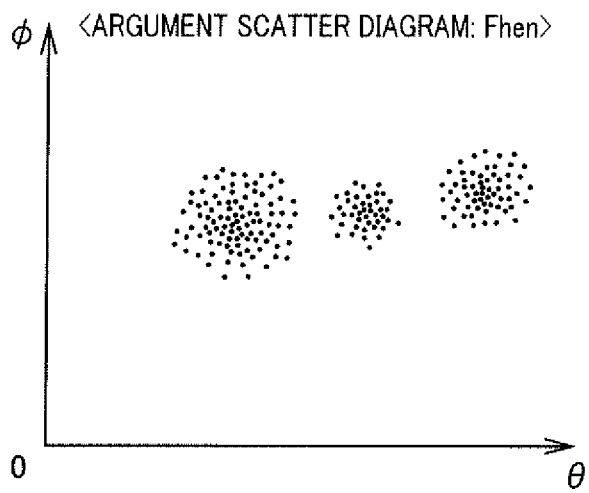
FIG. 33 is a diagram explaining one step of the image process in the fifth embodiment.
Figure 34:
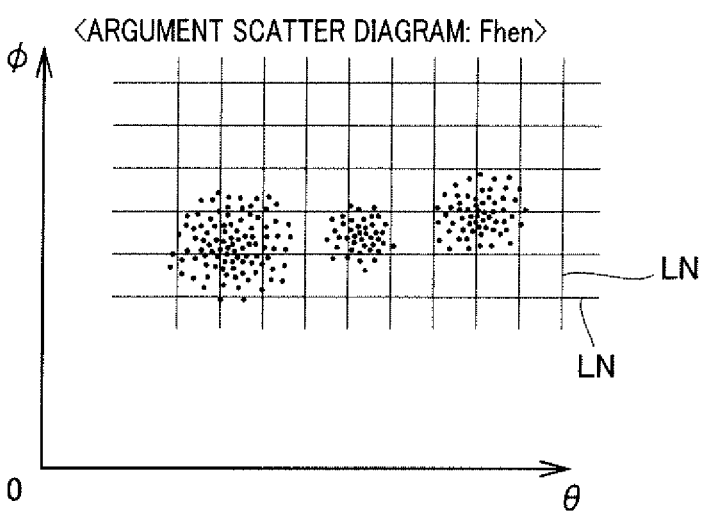
FIG. 34 is a diagram explaining another step of the image process in the fifth embodiment.

When proceeding to the process of FIG. 32, the data processor 35 reads the scatter diagram image $F_{hen}$ composed of the argument data (refer to FIG. 33), and displays that image on the display unit 38 (refer to FIG. 32, step S81). Then, by the data processor 36, this scatter diagram image $F_{hen}$ is divided in a plurality of grid-shaped small areas by division lines LN (refer to step S82 and FIG. 34). In this stage, the image with the division lines can be presented on the display unit 38 or, with no such presentation, can only be stored in the memory. The size and shape of each the small areas, and the numbers of such small areas can be set arbitrarily, so that the factors of the small areas are decided with taking it into account a balance between desired accuracy of determining foreign-matter contamination and an amount of necessary calculation. The data processor 35 then calculates the gravity center position of gray levels of the respective pixels in every small area divided, and stores the calculated gravity center position as a gravity-center position pattern $PT_G$ and, if necessary, displayed (step S83). This gravity-center position pattern $PT_G$ also shows information originated from inherent information showing substances, with the result that, in a theoretical view point, this pattern is the same among the subjects as long as the types or properties of substances are the same, i.e., substances or objects are composed of elements whose effective atomic numbers are the same.

Figure 35:
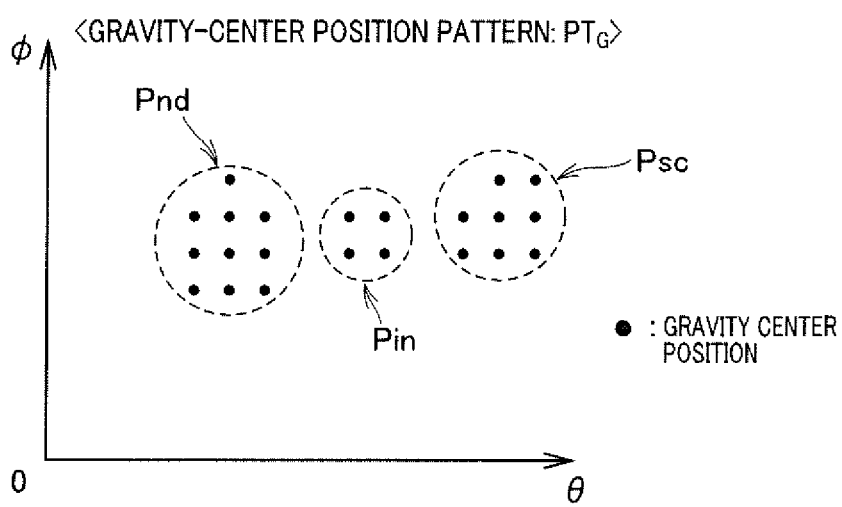
FIG. 35 is a diagram explaining another step of the image process in the fifth embodiment.

This gravity-center position pattern PTG can be exemplified as shown in FIG. 35. In this pattern, if a foreign matter is erroneously contained in the noodle pot, there are provided not only the gravity-center position pattern Pnd resulting from the noodle itself and a gravity-center position pattern Psc resulting from the sauce but also the gravity-center position pattern Pin resulting from the foreign matter. Unless there is no foreign matter, the gravity-center position pattern Pin showing the presence of a foreign matter will not be presented.

After detection of the gravity-center position pattern $PT_G$, the data processor 35 reads, into its work area, reference data $PT_{Gref}$ (refer to FIG. 36(A)) showing the gravity-center position pattern, in which the reference data $PT_{Gref}$ indicate the gravity-center position pattern which was previously set in a state with no foreign matter contaminated (step S84). Then a difference (and any other difference information) between these two gravity-center position patterns $PT_G$ and $PT_{Gref}$ is calculated to obtain difference information (step S95), and based on the resultant difference, and whether or not there exists a foreign matter is determined (step S86). When it is determined that there is mixed with the foreign matter (specifically, the foregoing gravity-center position pattern Pin showing presence of the foreign matter exists on the image: refer to FIG. 36(B)), an alarm for noticing that abnormality is issued (step S87).

In this way, the present embodiment uses the inherent information (arguments θ and φ) provided due to the type or property of a substance (, which is also due to an effective atomic number of the elements of the substance), and employs the gravity-center position pattern. Use of this the gravity-center position pattern makes it easier to detect a difference among varieties of the inherent information even in a case where the difference is small. Therefore, presence of a mixed foreign matter can be checked with higher precision.

Accordingly, it is possible to enrich modes for observing how the scattering points are scattered to provide X-ray energy information in an X-ray examination. Namely, as described before, the argument scatter diagram can provide an analysis with no dependency on directions in observing the diagram.

Sixth Embodiment

A sixth embodiment relates to an example in which the subtraction technique is applied to the foregoing contour-line display, and particularly, to an example which can examine the property of the substance, which is also categorized into the technical field of identifying substances. A practical example referred in this embodiment is for tracking the healing process of broken bones in a human body (or an animal) (, which is to check changes in broken bones). Information resulting from the tracking process can be helpful for cure and/or rehabilitation.

Figure 37:
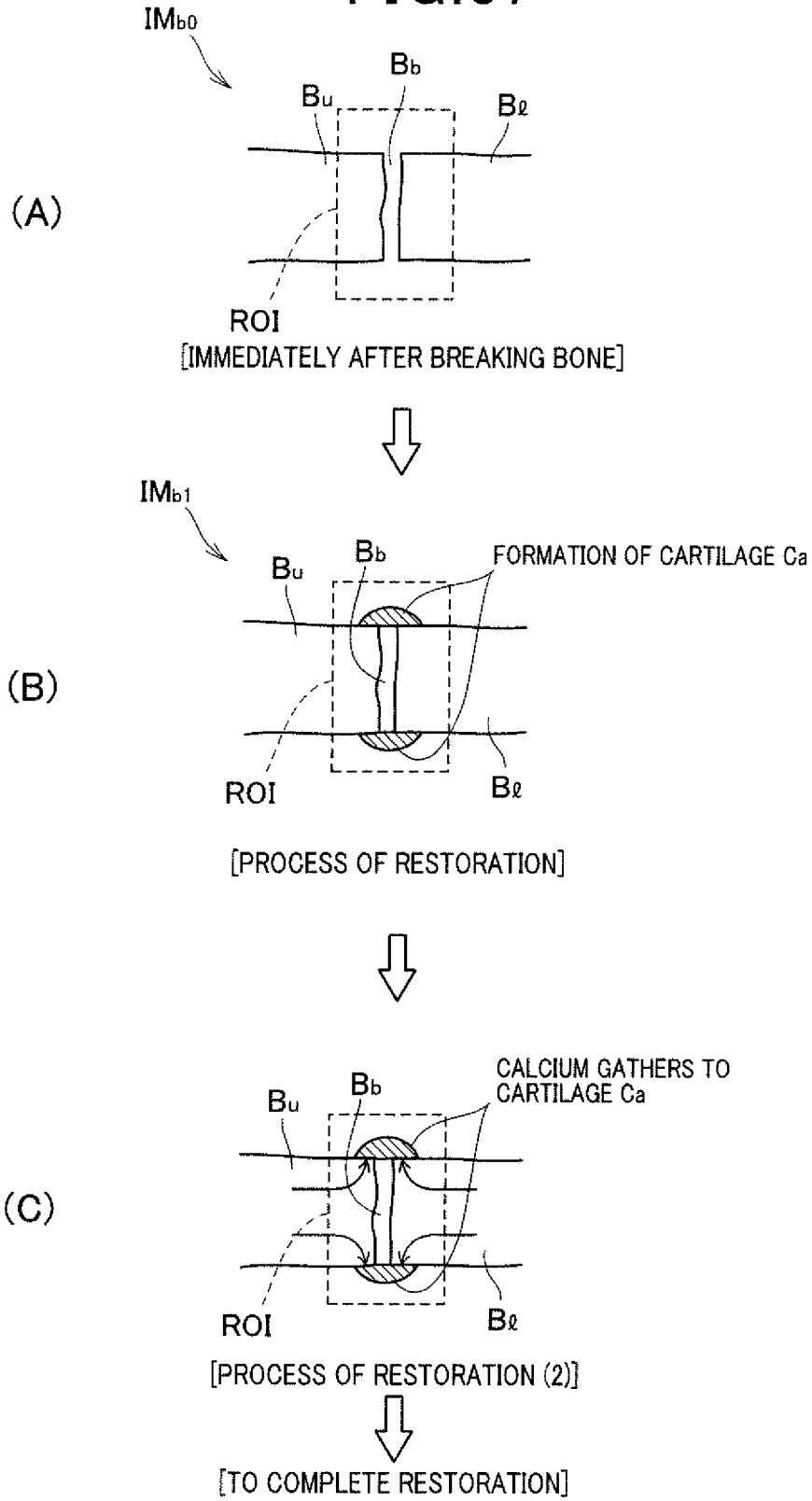
FIG. 37 is a pictorial illustration explaining broken bones of the human body, which are shown as an object for substance identification in a six embodiment.

For example, when bones in a human body are completely fractured, there can be provided cure steps advancing from a state 10 illustrated in FIG. 37(A) in which bones Bu and Bl are separated from each other to a state illustrated in FIG. 37(B) in which cartilage Ca is gradually formed at the broken position as the cure advances, which steps are of course dependent on where such bone broken occurs in the human body. As the cure advances, calcium collects to the cartilage portion Ca (refer to FIG. 37(C)), which makes the bones Bu and Bl connects to each other, thus being returned to the original no-broken state. For this cure process, conventional X-ray transmission images are not always suitable for tracing how the cartilage Ca has been formed and checking whether or not the broken bones have been connected or nearly connected to each other. An interpreter needs more experience in order to read the X-ray images in the observation. At least, the conventional X-ray transmission images are difficult to provide quantitative data indicating how the cartilage Ca is formed from an immediately-after broken state of bones to a fully healed state thereof.

Figure 38:
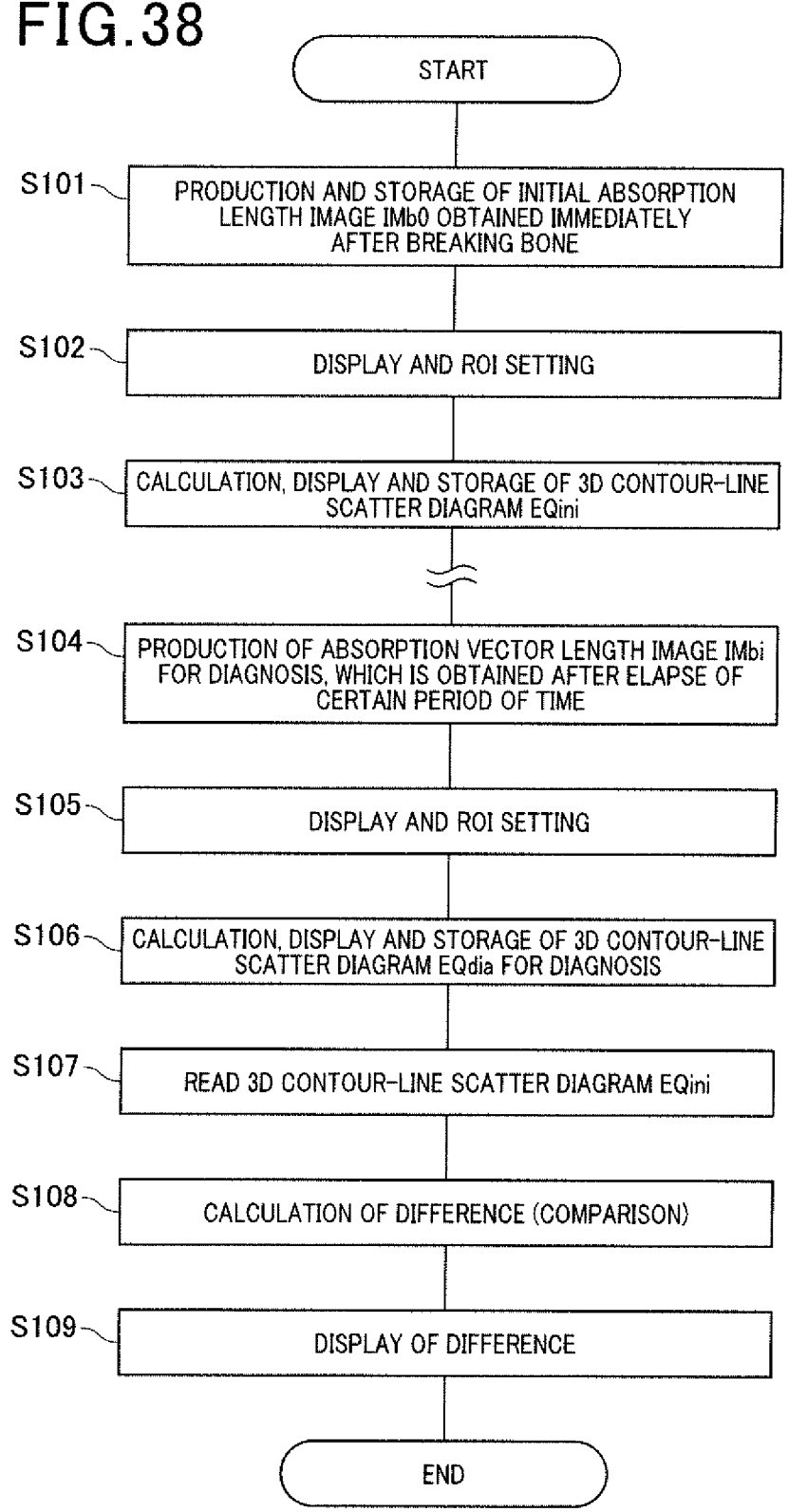
FIG. 38 is a flowchart outlining an image process for the substance identification, which is performed by the data processor in the sixth embodiment.

In order to improve this conventional situation, the substance identification technique according to the present invention can be used. In practice, the data processor 35 uses fame data of a broken bone portion Bb, which are scanned by the X-rays as described (refer to FIG. 37(A)), so as to generate an absorbance vector image length $IM_{bo}$ of the broken bone portion Bb, as described (FIG. 38; step S101). The data processor 35 then sets a ROI (region of interest) which encloses the broken bone portion Bb on this absorbance vector image length $IM_{bo}$ (step S102), calculates data of an initial three-dimensional contour-line diagram $EQ_{ini}$ (refer to FIG. 39(A)), as described, and then display the diagram on the display unit 38 and stores the diagram data in the image memory 36 (step S103). In this initial three-dimensional contour-line diagram $EQ_{ini}$, not only distributions resulting from the bones Bu and Bl but also a distribution $B_{others}$ resulting from portions other than the bones are depicted.

Figure 39:
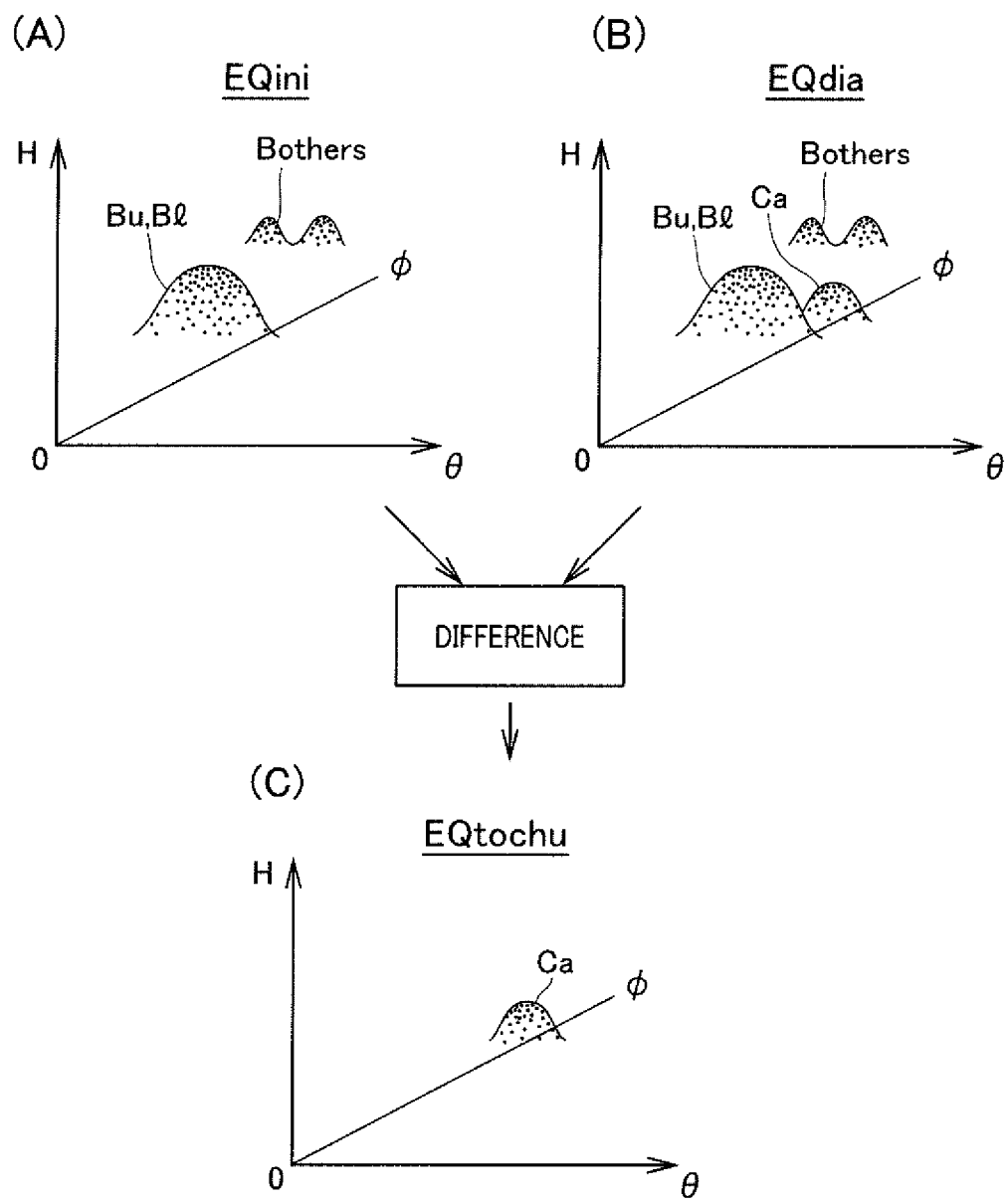
FIG. 39 is a diagram explaining one step of the image process in the sixth embodiment.

After an elapse of a required period of time (for example, 1 week), the data processor 35 generates again an absorbance vector image length $IM_{b1}$ from frame data X-ray scanned at the same broken bone portion Bb (step S104). This image $IM_{b1}$ is subjected again to setting a ROI (step S105), and a three-dimensional contour-line diagram $EQ_{dia}$ for diagnosis is calculated, displayed and stored (step S106). When the cure has advances, this three-dimensional contour-line diagram $EQ_{dia}$ depicts thereon a distribution resulting from cartilage Ca which has been formed or which shows that calcium has begun to collect, in addition to the initially depicted distributions, as illustrated in FIG. 39(B).

The data processor 35 then reads, from the image memory 36, the data indicating both the initial three-dimensional contour-line diagram $EQ_{dia}$ and the three-dimensional contour-line diagram $EQ_{dia}$ for the diagnosis (step S107), and calculates differences for every coordinate position, between both images (step S108).

Furthermore, the data processor 35 represents the results of the difference calculation on the display unit 38 in a form of a three contour-line diagram $EQ_{tochu}$ which provides information showing until which state the cure advances, and stores the results in the image memory 36 (step S109; representing diagnostic information). Because of this difference calculation, only a distribution Ca is depicted in the three-dimensional contour-line diagram $EQ_{tochu}$, in which the distribution Ca newly appears in the three-dimensional diagnostic contour-line diagram $EQ_{dia}$, as shown in FIG. 39(C).

In the present embodiment, the cartilage formation process of broken bones, which has not always been obtained or was difficult to be read by the conventional X-ray imaging, can be visualized in a timely manner. In addition, portions of distributions on the three-dimensional contour-line diagram $EQ_{tochu}$ resulting from the difference calculation can be evaluated quantitatively in terms of their movement distances and densities, with the result that it is possible to easily check the stage of the cartilage formation process, i.e., whether or not the cure has advanced. As the cure advances in which calcium collects in the cartilage Ca, the property of the cartilage Ca will return to the original stages of the bones Bu and Bl. In a composition view point, the effective atomic number of the cartilage will approach to its original number. In this way, a small progress in the growing process of the cartilage (i.e., a change in its property) can be tracked timely, which was not easy for the conventional technique, thus providing helpful information for treating broken bones, thus making it possible to decide quickly whether or not, for example, a further surgery is required in the cure process.

In addition, the foregoing three-dimensional mass attenuation vector $(\mu_{1m}, \mu_{2m}, \mu_{3m})$ or the three-dimensional linear attenuation vector $(\mu_1 t, \mu_2 t, \mu_3 t)$ is used to produce the contour-line distribution diagram. This is advantageous in that it is not necessary to become so nervous about positioning a ROI on the images when the ROI is set on both of the initial and diagnostic absorption vector length images $IM_{b0}$ and $IM_{b1}$. In other words, provided that the ROI encircles a broken portion Bb, the ROI is sufficient for the interpretation, thereby reducing burden on the user's operation work.

In a broader meaning, the present embodiment can provide a scheme which can be understood that, a three-dimensional or two-dimension mass or liner (X-ray) attenuation vector is obtained by X-ray scanning the same subject portion at different timings, three-dimensional or two-dimensional contour-line diagrams are calculated based on such a attenuation vector obtained at the different timings, and the calculated contour-line diagrams are subjected to difference calculation in order to estimate changes of properties at the examined portion. This estimation can be applied not only by observing how broken legs have been cured, as explained in the embodiment, but also a subject or a portion of the subject which provide time-sequential state changes.

As a result, it is possible to enrich modes for observing scattered states of the scattering points which provide energy information. Practically, as described, an analysis of time-sequentially obtained argument scatter diagrams, which eliminate dependency on the observing direction, can be eased.

Seventh Embodiment

A seventh embodiment relates to an analysis technique which can categorize two substances on a scatter diagram, to which the present inventors refers as a categorizing (classifying or border-dividing) line technique. In this analysis, the foregoing two-dimensional argument data ($\theta$, $\phi$) (for example, refer to FIG. 22) can be used.

Figure 40:
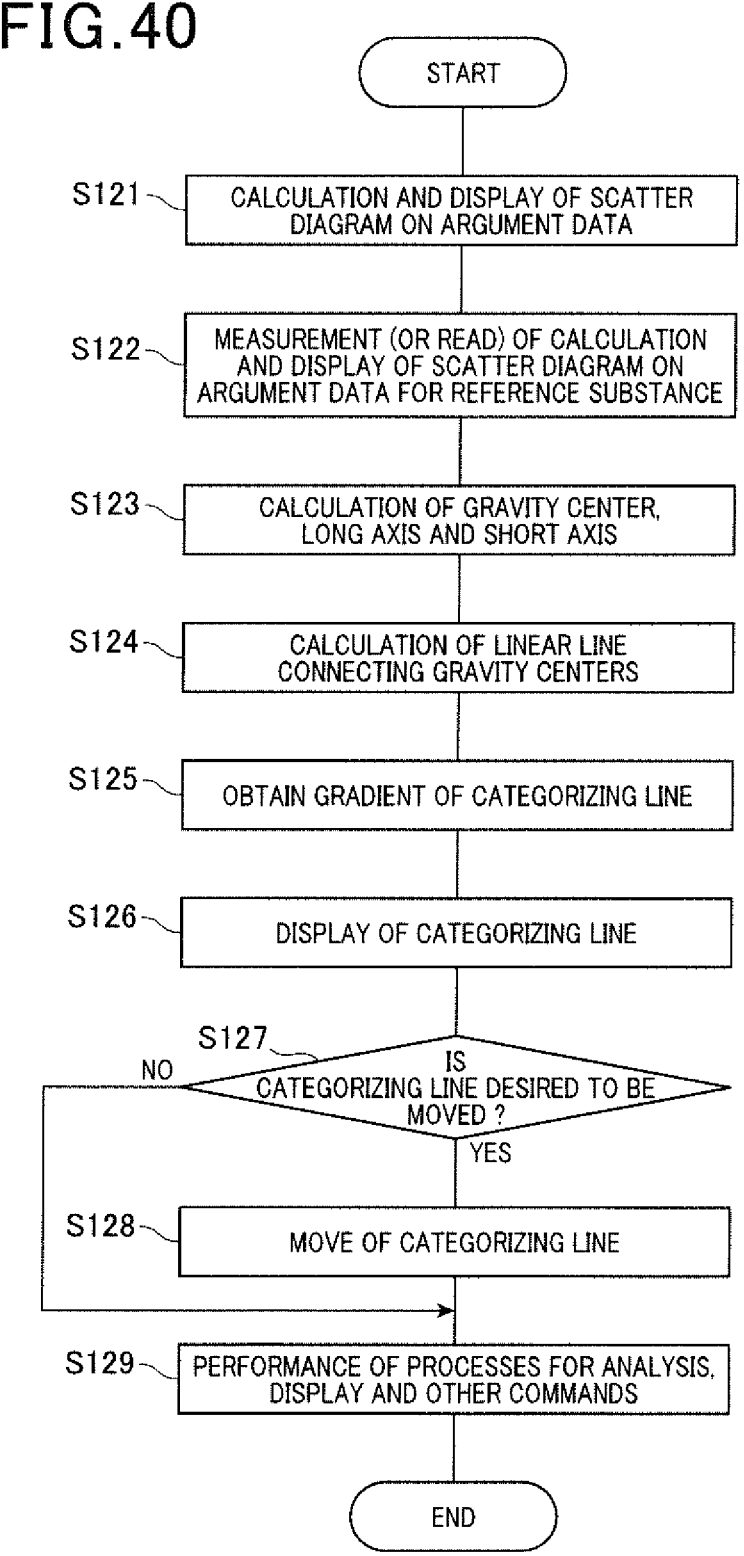
FIG. 40 is a flowchart outlining an image process for inspecting a substance property, which is carried out for substance identification by the data processor in a seventh embodiment.
Figure 41:
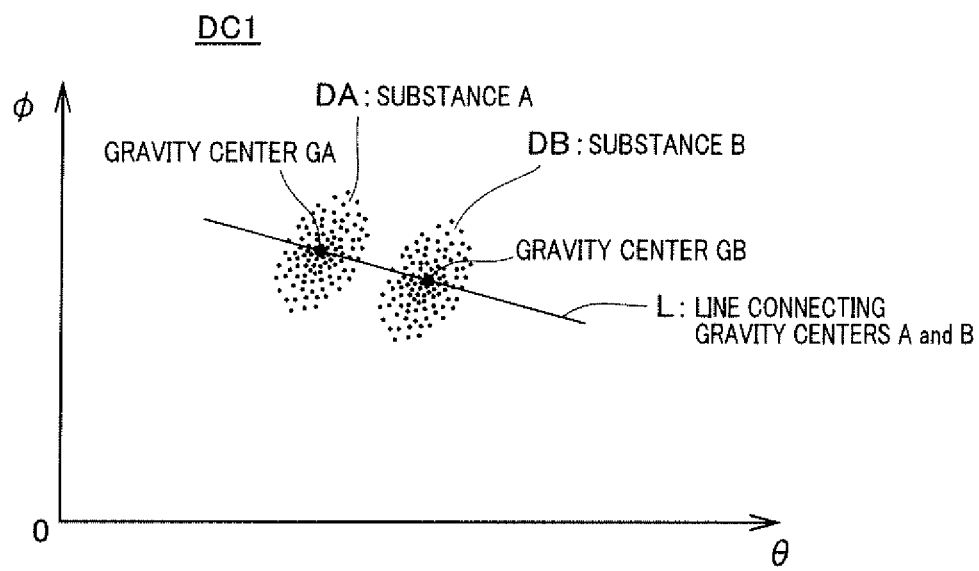
FIG. 41 is a diagram explaining one step of the image process in the seventh embodiment.

It is now assumed that two substances A and B whose types are mutually different are mixed in their compositions into a one object being examined and X-ray scanned. In this case, at step S121 of FIG. 40, as described before, the data processor 35 calculates an argument-data scatter diagram DC1 based on frame data acquired by X-ray scanning or X-ray imaging (a shot imaging with no scanning) the object. As described, the diagram DC1, which is composed of argument data ($\theta$, $\phi$), is presented on the display unit 38. FIG. 41 exemplifies this presented image. In FIG. 41, distributions DA and DB indicate spreads (group or aggregate) of scattering points of the substances A and B, respectively. These distributions DA and DB are normally not separated distinctly in the diagram, but frequently partly mixed with each other so that the border between the distributions are not clear. In such a case, the categorizing line according to the present embodiment is effective.

For this purpose, the data processor 35 proceeds to step S122, in which, interactively with an operator, the data processor 35 measures the thickness of a reference substance C (or reads the thickens measured in advance) and displays an argument-data scatter diagram DC2 in the same as before. The reference substance C is selected as a substance whose competitions are almost the same as those of the substances A and B (in this case, the types of substances A and B (i.e., the effective atomic numbers) are known) and indicates X-ray absorption values which are almost the same as those of the substances A and B in the respective energy regions Bin1 to Bin3. FIG. 60 exemplifies this argument-data scatter diagram DC2.

Then, at step S123, in one of the scatter diagrams, DC1, gravity points GA and GB in the scattering point distributions of the substances A and B are decided respectively. In addition, in the other scatter diagram, DC2, a gravity center FC, a major axis LA, and a minor axis SA in the scattering point distribution of the reference substance C are also decided. As a modification, the two scatter diagrams DC1 and DC2 are can be presented on a single display unit 38 or separately displayed on two display units 38. Additionally, these two scatter diagrams DC1 and DC2 can be presented on a single two-dimensional coordinate ($\theta$, $\phi$).

Figure 42:
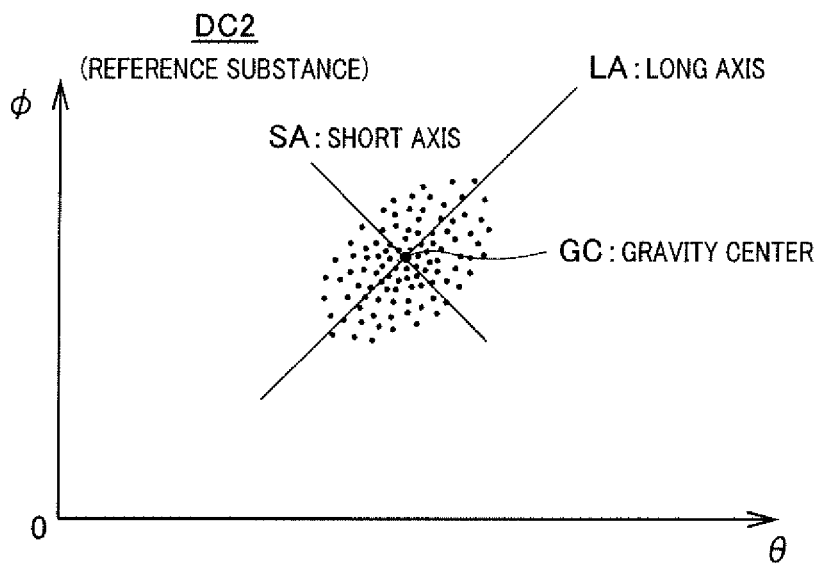
FIG. 42 is a diagram explaining another step of the image process in the seventh embodiment.
Figure 43:
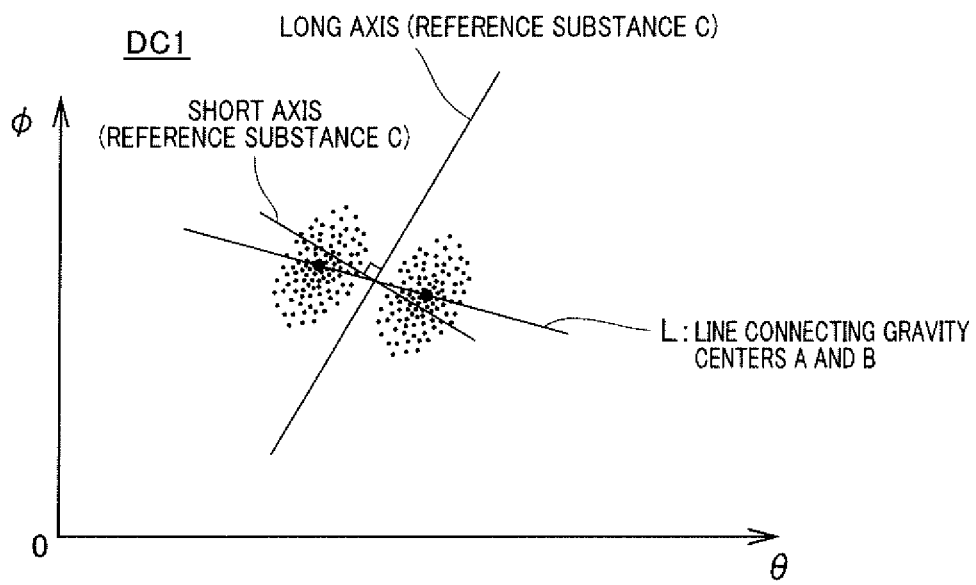
FIG. 43 is a diagram explaining another step of the image process in the seventh embodiment.
Figure 44:
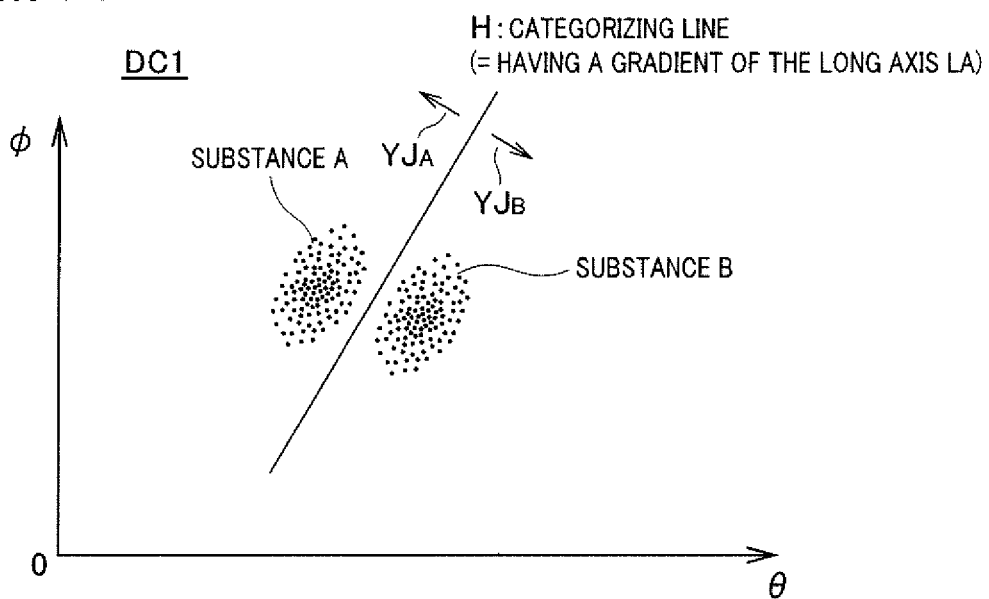
FIG. 44 is a diagram explaining another step of the image process in the seventh embodiment.

Further, the data processor 35 calculates a straight line L connecting the gravity centers GA and GB on the one scatter diagram DC1 (step S124) and a gradient of a desired categorizing line H described below (step S125: refer to FIG. 43). That is, when the gradient of the categorizing line H is decided such that the major and minor axes LA and LB of the reference substance C are made to cross the straight line L, with their coordinates ($\theta$, $\phi$) matched with each other, the major or minor axis of the reference substance C is selected which has a crossing angle closer to 90 degrees than the other is, and the gradient of the selected axis is set to the gradient of the desired categorizing line H. In this example, based on the data indicating FIGS. 41 and 42, the gradient of the major axis LA from the reference substance C is stored as the gradient of the categorizing line H. As shown in FIG. 44, the straight line having the gradient of the major axis LA decided is presented at its default position in one scatter diagram DC1 (step S126).

Moreover, the data processor 35 determines whether or not it is necessary to the displayed categorizing line H on the scatter diagram DC1, which is performed interactively with the user (step S127). When being necessary to move the line H, the data processor 35 responds to a user's manual operation interactively such that the categorizing line H is moved on the scatter diagram DC1 (step S128). As a result, the categorizing line H, which has been at its default position, is made to move parallel towards the distribution from the substance A or B (refer to arrows $YJ_A$ and $YJ_B$ in FIG. 44). After this adjustment of movement of the categorizing line H, the data processor conducts a desired distribution analysis and/or a representation process on the scatter diagram DC1 (step S129). When it is determined a NO at step S127, the process at step 129 is executed before ending the process.

Figure 45:
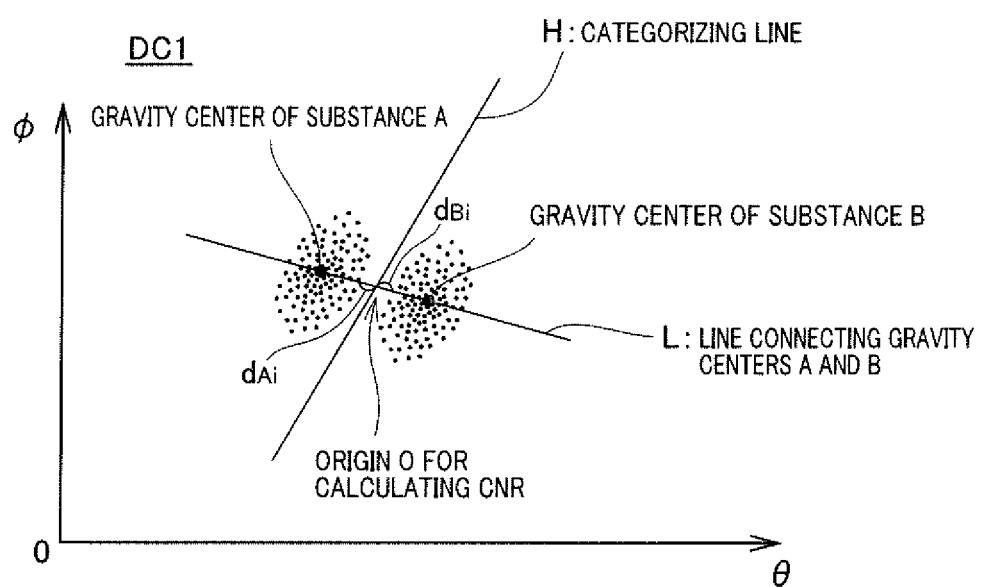
FIG. 45 is a diagram explaining another step of the image process in the seventh embodiment.

One desired analysis of the distribution on the scatter diagram DC1 is provided as a technique of calculating CNRs (signal-to-noise ratios) of the scatter diagrams, and based on the calculated values, checking how far the two distributions of the substances A and B are separated from each other. As shown in FIG. 45, the scatter-diagram CNR shows a geometry, in which a point at which the categorizing line H and the line L connecting the gravity centers GA and GB of the substances A and B is defined as the origin O; parallel lines are drawn from each of the scattering points of the respective substances A and B towards the categorizing line H so as obtain intersections of the respective drawn parallel lines to the categorizing line H; distances between those intersections and the origin are thus expressed as $d_{Ai}$, $d_{Bj}$ (j=1, 2, . . . ; i=1, 2, . . . : i and j denote the number of scattering points in each distribution) are obtained; and the obtained distances are then subjected to calculation of root-mean values. Such root-mean values indicate one of the factors which evaluates the noise-to-signal ratio. As an example, if the categorizing line H is positioned such that the line H is able to provide the same root-mean value for the two distributions of the substances A and B, it can be understood that the distributions of the substances A and B are sufficiently separated on the scatter diagram DC1 from each other.

For this reason, a calculated scatter-diagram CNR can be used to correct the position of the foregoing categorizing line H.

Alternatively, the scattering points divided in the vertical or lateral direction by the categorizing line H on the scatter diagram DC1 can be colored in red and blue, for example, to show mutually distinguished colors. This distinguished coloring display may make it possible to observe, in a comparative manner, how the substances A and B are mixed with each other. Hence, even if the scatter diagram DC1 shows indistinctly combined distributions of the substances A and B, use of the categorizing line makes it clearer how the substances are mixed with each other.

In this way, the substances A and B comprising an object being examined can be divided steadily on the scatter diagram. This enables two group of scattering points to be divided, mutually compared, and analyzed, thereby providing information indicative of a mixed degree of the substances A and B in a specified portion of the object.

It is therefore possible to enrich modes which can be used for observing how the scattering points showing X-ray energy information are distributed. More concretely, as described, the argument scatter diagram, which is able to remove the directional dependency in observing displayed images, can be analyzed more easily.

Eighth Embodiment

An eighth embodiment exemplifies positional association and coloring display associated, position by position, between an image of an object being examined and its scatter diagram. This is one application provided when the three-dimensional mass attenuation vectors ($\mu_{1m}$, $\mu_{2m}$, $\mu_{3m}$) or the three-dimensional linear attenuation vectors ($\mu_1 t$, $\mu_2 t$, $\mu_3 t$).

In the present embodiment, there are provided examples such that an object being examined is a human breast, the image is a two-dimensional absorption vector image, and the scatter diagram is provided as a two-dimensional argument-data scatter diagram.

Alternatively, in the applications of the present invention, an object being examined is not always limited to a mammography image but may be for images obtained from other portions of the human body or an animal, food items, industrial products, or others. Still alternatively, images produced to show a contour by pixel gray levels and used for associated color imaging may be a mere X-ray transmission image or a two- or three-dimensional optimally focused X-ray transmission image of an object. Moreover, such images may be an image obtained by an X-ray flat panel, or a CT tomographic image reconstructed as projection images of absorption vector length images acquired by CT imaging.

Figure 46:
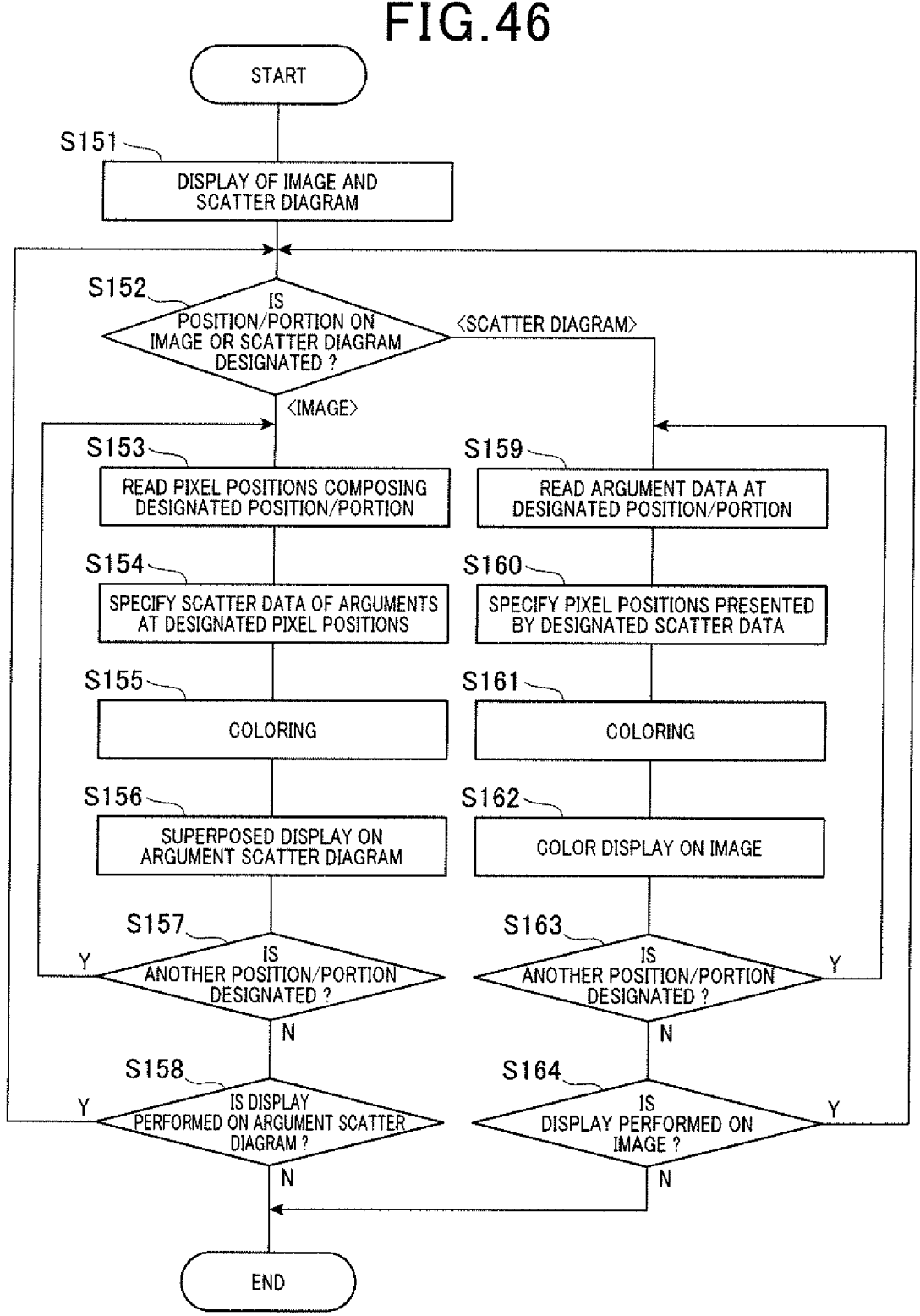
FIG. 46 is a flowchart outlining an image process for mammography, which is another example for substance identification carried out by the data processor in an eighth embodiment.

In the present embodiment, by way of example, the data processor 35 makes the display unit 38 represent thereon a two-dimensional absorption vector length image and two-dimensional argument data ($\theta$, $\phi$), both acquired by imaging a human breast and processing acquired data (FIG. 46; step S131). The data processor 35 then determines whether or not an operator desires to interactively designate a position or a portion on the image, or designate a position or a portion on the scatter diagram (step S132). In this case, the position or portion is referred to as an area composed of a plurality of pixels.

Figure 47:
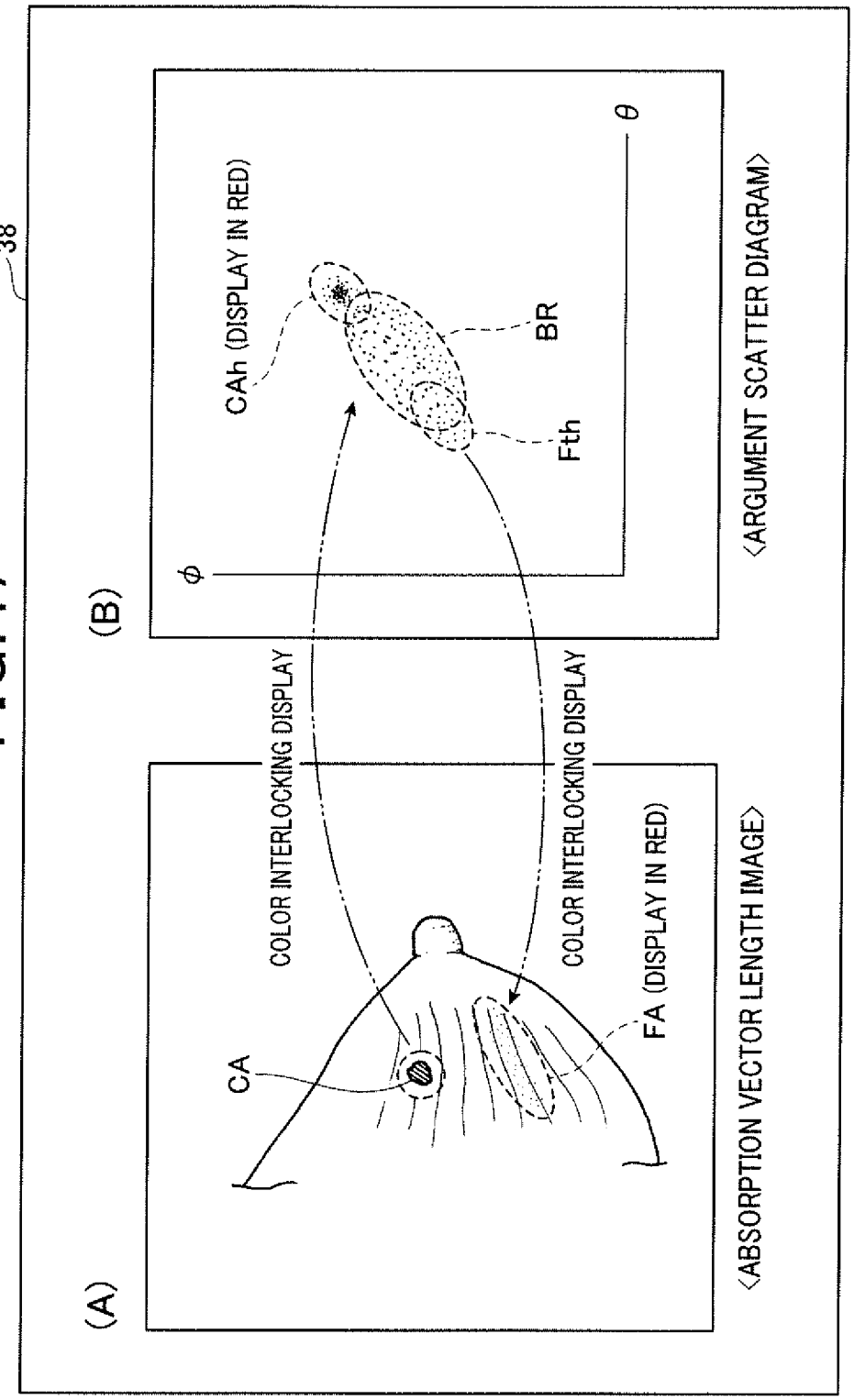
FIG. 47 is a pictorial illustration explaining the image process in the eighth embodiment.

For instance, the operator designates a ROI at a suspected portion CA to tumor mass on the morphological image, as shown in FIG. 47(A). In this case, the data processor 35 reads information about the positions of pixels which compose the designated portion CA (step S133). The data processor 35 then specifies argument scatter data corresponding to the specified pixel positions among the data showing the two-dimensional argument-data scatter diagram which is calculated in advance (refer to FIG. 47(B)) (step S134). The specified argument scatter data are then colored by a specified hue (for example, red) (step S135). The colored argument scatter data are then superimposedly displayed on the argument scatter diagram which has already been displayed, as shown in FIG. 47(B) (step S136).

As a result of this superimposed display, in FIG. 47(B), a reference symbol CAh represents color display of the suspected portion CA. The reference symbol BR indicates the portion of mammary gland which is affected by dense breast. An interpreter observes the position of the red portion CAh and a spread thereof on the argument scatter diagram, in order to obtain information for determining that the portion CAh is simply read as mammary gland or a lesion such as cancer. This enables the interpreter to check the suspected portion on the absorption vector length image in terms of the type or property of the substance in the sense of X-ray energy analysis, thus providing improvement in diagnostic accuracy.

The data processor 35 then determines whether or not another portion on the absorption vector length image should be designated or the analysis should be performed on the scatter diagram (steps S137, S138). From this determination, the interlocking (or coordinating, associating) display process is returned to step S133 or S132, thus making the foregoing steps repeat.

Meanwhile, when it is determined at step S132 that the analysis mode specifies the position or the portion on the argument scatter diagram, the data processor 35 reads argument data ($\theta$, $\phi$) pointed out by the specified position or portion (step S139). Then, the read argument data ($\theta$, $\phi$) is used to specify corresponding pixel positions representing the read argument data ($\theta$, $\phi$) on the morphological image (step S140), the read pixel positions are given color information (for example, red) (step S141), and the corresponding pixels on the morphological image is then color-displayed based on that color information (step S142).

Accordingly, on the argument scatter diagram shown in FIG. 47(B), for instance, the portion FA whose pixels correspond to the portion FTh designated by the ROI is colored and displayed (refer to FIG. 47(A)). By this associated coloring display, it is thus easily obvious to the interpreter that a region of interest on the argument scatter diagram corresponds to which position on the morphological image of the object. Hence, as described, this enables the interpreter to confirm both information indicating the type or property of a substance, which results from X-ray energy analysis, and an image morphology in a mutually associated manner, thus providing improvement of the diagnosed information. Of course, the color used in this interlocking (or coordinating, associating) display can be another hue other than red. As an alternative to the color, changes in gray levels of pixels can be employed as well.

The data processor 35 then determines whether another portion being analyzed on the argument scatter diagram is determined or a portion being analyzed is changed to that on the absorption vector length image (step S143, S144).

Depending on this determination, this interlocking display process is returned to step S133 or S132 and to repeat the foregoing steps.

In the present embodiment, it is thus possible to enrich the modes for observing how the scattering points are spread, from which the X-ray energy information is still given. Practically, as described, the argument scatter diagram, which can remove the directional dependency in observing the scatter diagram, can be used to provide an associated color display to and from the homological image, thus making it possible to interpret the type of property of tissues (substances) in an object being examined in a steadier and more reliable manner.

MODIFICATIONS

First Modification 1

The present invention can also be applied to a technique, referred to as a DEXA (Dual Energy X-ray Absorptiometry) technique, which involves radiation of two types of X-rays whose energy amounts are different from each other and measurement of a bone density based on the difference between absorption rates of the bone and a soft tissues.

Second Modification 2

The substance identification technique according to the foregoing embodiments is not always limited to its performance in the three-dimensional coordinate space. For example, in the frequency spectrum shown in FIG. 3, if using the first and second energy ranges $Bin_1$, $Bin_2$; $Bin_2$, $Bin_3$; or $Bin_2$, $Bin_3$ to perform the substance identification in the same way as that explained before, a two-dimensional scatter diagram and an absorption vector length image can be obtained. By this modification, a gradient (substance-inherent information) and a length (absorption amount) of the two-dimensional mass attenuation vector, which is simplified into a two-dimension, can be used for the substance identification in the same way as the foregoing.

Third Modification 3

The formula (8), which is for generating the foregoing absorption vector length image, can be generalize as below.

$$(a \times (\mu_1 t)^2 + b \times (\mu_2 t)^2 + c \times (\mu_3 t)^2)^{1/2} \quad (8')$$

In this formula (8'), symbols a, b and c are coefficients which are any numbers for performing weighing addition. An absorption vector length image produced on this formula can be used for, for example, designing the radiation conditions of an X-ray tube, which design enables the X-ray tube to have an energy spectrum of X-rays radiated to an object depending on the types or specific gravity of the object.

Fourth Modification 4

An additional modification concerns with default display on the monitor and changes of displayed states by rotation and shift operations.

The data processor 35 functionally provides a display control structure which allows the display unit 38 to represent thereon a scatter diagram in its predetermined default display state. In addition, the data processor 35 functionally provides a display state commanding structure capable of commanding another display state different from the already displayed state of the scatter diagram. Responsively to the displayed state commanded by the display state commanding structure, the display of the scatter diagram represented on the monitor 38 can be changed by a display change structure functionally provided by the data processor 35. This display state commanding structure can include a coordinate converting structure which coordinate-converts two types of scatter diagrams by at least one of rotation and shift operations. This coordinate conversion is intended to visually compare the two scatter diagrams on the display unit.

The foregoing various embodiment and modifications can be practiced solely or in an adequate combination.

Experimental Example

Incidentally, the present inventors conducted an experiment and considered applications thereto. In the experiment, yellowtail, which is categorized into relatively larger-size fish, was selected as an object being examined, the raw yellowtail was subjected to an X-ray examination to determine whether or not a foreign-matter detection and property check are possible as the substance identification according to the invention. Three raw yellowtail in which parasitic insects were put as foreign matters were prepared as specimen and the experiment was targeted to whether the parasitic insects were able to be detected. Because this is an experiment, the positions of the parasitic insects were previously known. Generally, since one of factors for good quality of the yellowtail is a degree of fat included, the inventors decided to check a property (the degree of fat) of a substance (fat).

For this purpose, the three raw yellowtail were subjected to scanning by the X-ray examination apparatus shown in FIG. 1. Data resulting from this scanning were used to produce a vector-length image (refer to FIG. 48) according to the foregoing technique, and the data were displayed. As a result, the displayed image showed shades of the parasitic insects PA.

In addition, in order to check how fat the yellowtail are, an argument-data scatter diagram (θ, φ) were drawn by the data process described before (refer to FIG. 49(A)). The resultant scatter diagram showed three large distributions approximately consisting of a distribution R1 with more fat, a distribution R2 mainly with lean tissue and bones, and a distribution R3 mainly with fins (bone property). On this scanner diagram, the foregoing categorizing line LA was applied to divide the distributions into a fat distribution and a distribution of components other than the fat. Furthermore, this diagram was made to associated with the absorption vector length image shown in FIG. 48, in which scattering points within the fat distribution divided by the categorizing line LA were interlocking displayed to correspond to portions (or areas) on the absorption vector image such that such portions are displayed in red (refer to FIG. 49(B)). When the categorizing line LA was moved on the diagram in a direction along the effective atomic number changes, it was also confirmed that the red portions on the vector length image change in its spreads and positions. As described, the categorizing line LA can be set to make a separation among a plurality of distributions of scattering points (θ, φ), although noise is included in this separation. Hence, the red portions on the vector length image shown in FIG. 49(B) indicate fat portions of the yellowtail. It was thus confirmed that observing and processing this image provides an estimation about how the fish is fat.

Figure 50:
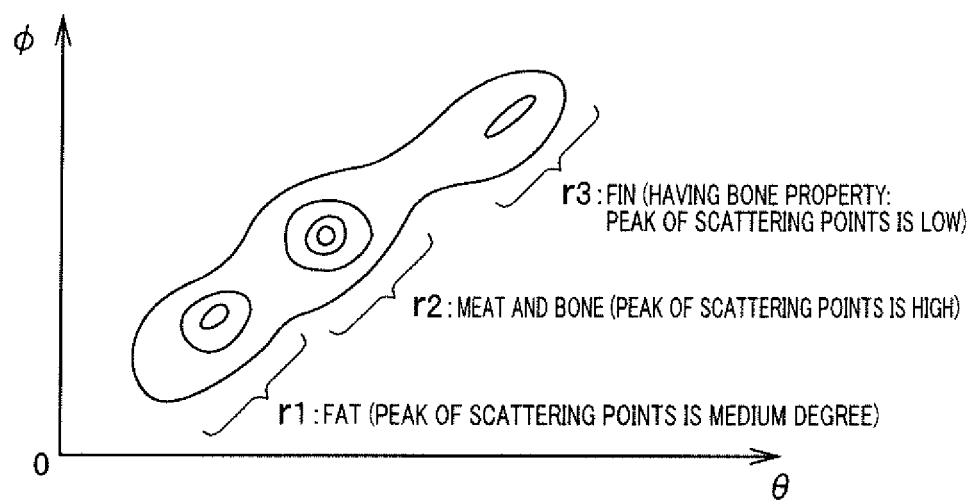
FIG. 50 is a diagram showing a two-dimensional contour-line image, which is exemplified based on an image process carried out in the applied example.

The present investors also devised a two-dimensional contour-line representation diagram, in which another dimension H (i.e., indicating the number of scattering points within each preset region) is added to the argument scattering points to generate data for displaying the number of scattering points. This diagram is pictorially shown in FIG. 50. As the intervals of the contour lines becomes narrower and denser, a peak value which is the number of scattering points becomes higher. In FIG. 50, there are drawn peaks of scattering distributions r1 (mainly fat), r2 (lean tissue and bones), and r3 (mainly bone properties due to fins) corresponding to the distributions R1, R2, and R3, respectively. It was thus confirmed that the two-dimensional contour-line display can be combined with the vector length image, argument data starter diagram, and those interlocking display in order to examine (or check) how fat the fish is and whether the fish is contaminated with foreign matters. Of course, although a degree of fat depends on individual yellowtail, it is also possible to identify differences of the degree of fat among the individual yellowtail.

Fifth Modification 5

Another modification will now be described, which concerns with display of the two-dimensional argument-data scatter diagram. This modification will be described with use of the argument-data scatter diagram shown in FIG. 49(A), which was obtained by the experiment performed with the foregoing yellowtail.

A displaying process in this modification is intended to facilitate local analysis of the argument-data scatter diagram and, for this purpose, to provide a tool which enables to divide freely, but until a preset division maximum number, the argument-data scatter diagram and display the respective divided regions of the diagram in various modes. This modification is based on involving the divided regions, in addition to associating with the foregoing various display processes. In the argument-data scatter diagram, this division is correspondent on dividing a region covered by the scattering points into a plurality of regions in the largeness direction of the effective atomic number Zeff.

Figure 51:
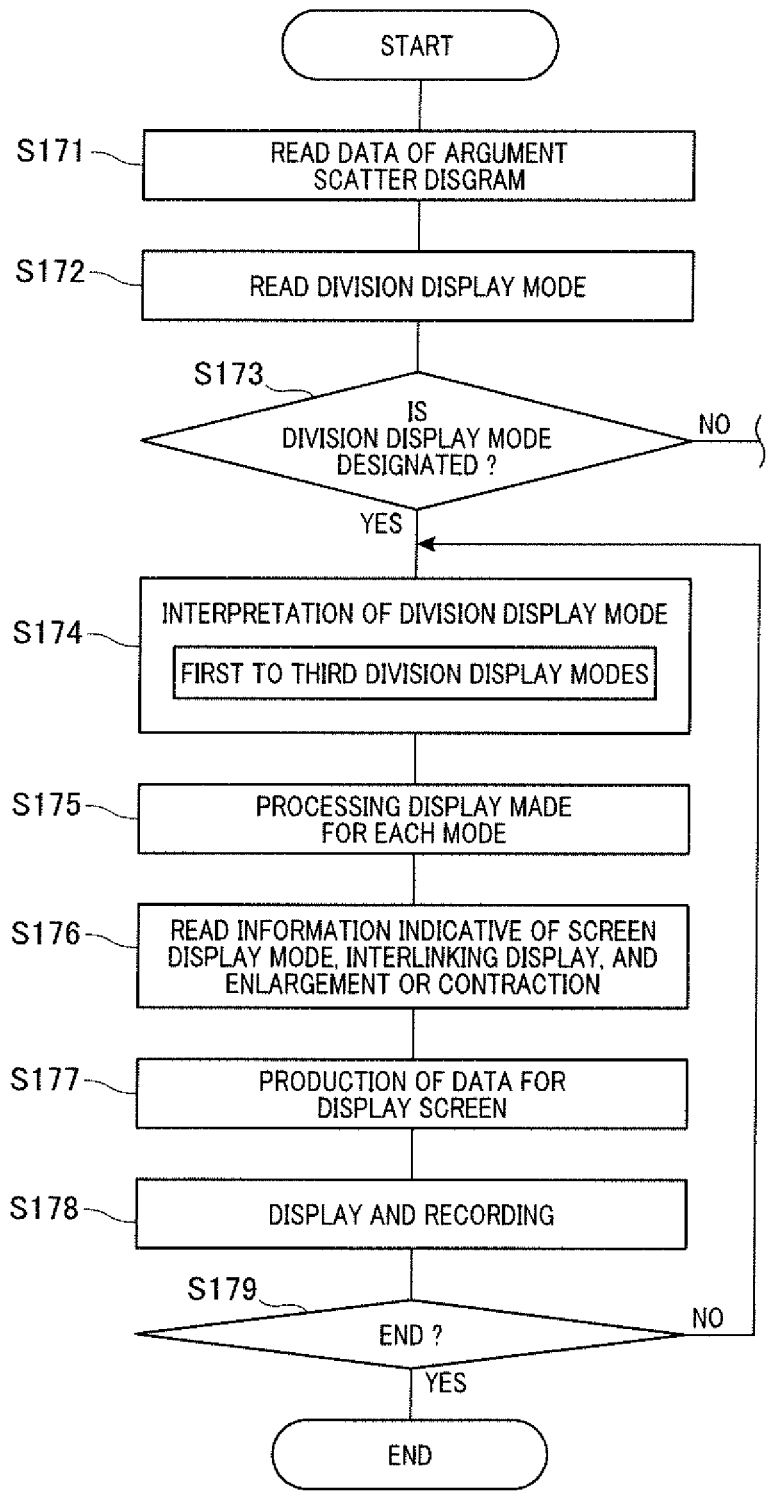
FIG. 51 is a flowchart outlining a display mode according to a fifth modification, in which an argument-data scatter diagram is displayed in a divided manner.

To perform this display, a display process outlined in FIG. 51 is executed, in an interactive manner with an operator, by the data processor 35, the image memory 36, the display unit 38, and the input unit 37. Attentively, the display process can be executed in a default procedure preset for each of display modes.

The data processor 35 first reads into its work area data of the argument-data scatter diagram (θ, φ) shown in FIG. 49(A), from the image memory 36 (FIG. 51, step S171). Then, the data processor 35 perform an interactive process with the operator using the input unit 37 and the display unit 38 in order to read information for selective an operator's desired display mode (step S172).

The data processor 35 responds to this process by determining whether or not the read information includes a display order requiring division of the argument-data scatter diagram (step S173). When it is determined NO at this step, it can be found that the request does not involve division of the display. In this case, the processing of the data processor 35 proceeds to other necessary processes. In contrast, if it is determined YES at step S173, any of designated display modes involves regional division of the diagram, so that the processing proceeds to sequential performances at steps S174 and thereafter.

First, at step S175, a designated divided-display mode is interpreted in terms of its contents. In this modification, first to third divided-display modes are prepared in advance, which are as follows:

First Divided-Display Mode

Figure 52:
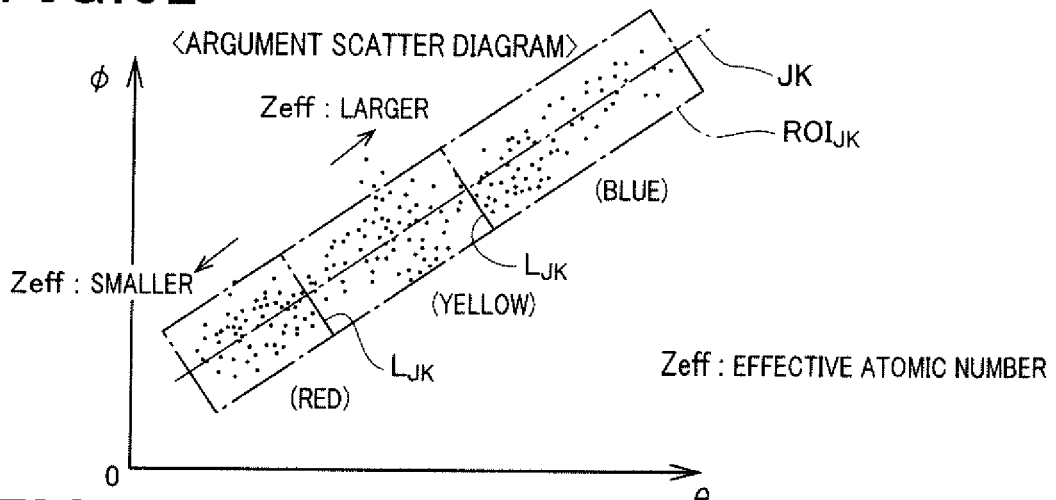
FIG. 52 a screen image exemplifying a first divided display mode according to the fifth modification.

In this first divided-display mode, as illustrated in FIG. 52, an argument-data scatter diagram (θ, φ) is represented on the display unit 38 and a fixed or non-fixed shaped ROI (region of interest): $ROI_{JK}$ which encloses the scattering points is set on the representation.

The $ROI_{JK}$ can be withdrawn by hand freely, or can be given as a default-set fixed shaped region on the scatter diagram based on a target point thereon. Of course, this fixed shaped region may be modified as being able to be adjusted by hand. This ROI: $ROI_{JK}$ is also able to remove nose scattering points from being taken in the calculation. Hence, an adequately set ROI: $ROI_{JK}$ enclosing necessary scattering points is set in a superposed display manner.

After setting the ROI: $ROI_{JK}$, an adequate manner is used to set a central axis JK along the largeness direction of the effective atomic number Zeff within the ROI: $ROI_{JK}$. This central axis JK can be withdrawn by hand or set as a linear or curved line passing a gravity center calculated in each of distributions of the scattering points. When drawing this central axis JK, the foregoing categorizing line can be used to calculate the position of the gravity center of each of the respective distributions composed of the scattering points.

After deciding the central axis JK, by way of example, one or more liner lines $L_{JK}$ which are perpendicular to the central axis JK are drawn at equal or unequal intervals to divide the area of the ROI: $ROI_{JK}$ into a plurality of regions. Further, the scattering points belonging to the divided regions are colored in mutually different tunes, and color-displayed, as exemplified in FIG. 52.

In this divided display, an operator can select other alternative factors such as the number of divided regions, the lengths of the divided regions, and color tunes in the color display (for example, how gradation of the color tunes are set in a descending- or ascending order direction of the effective atomic numbers Zeff. These factors may be decided by default setting. Alternatively, instead of the color display, gradations of gray levels can be used in this display. Moreover, the lengths of the divided regions can be set such that a divided region given to intermediate effective atomic numbers Zeff is smaller than those given to the other effective atomic numbers.

Second Divided-Display Mode

Figure 53:
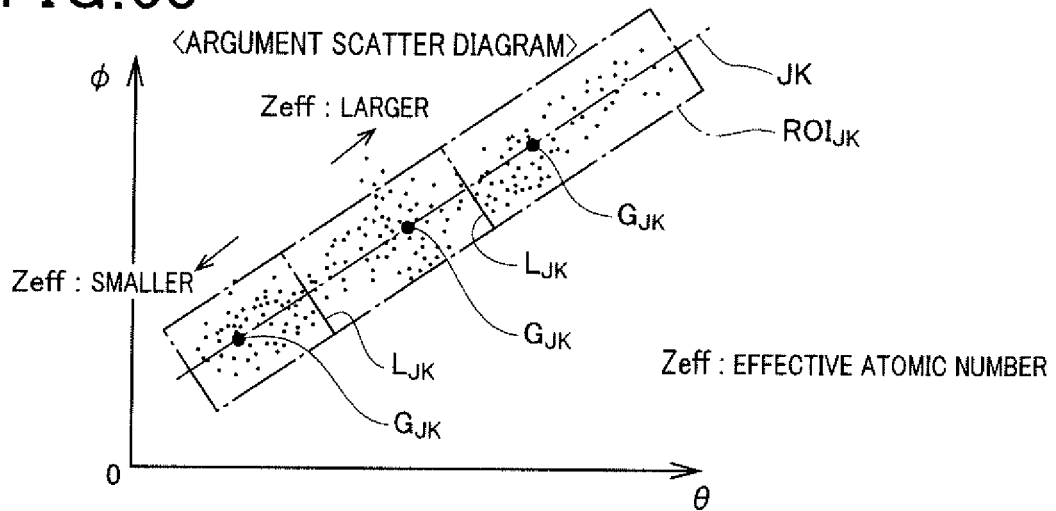
FIG. 53 a screen image exemplifying a second divided display mode according to the fifth modification.

As illustrated in FIG. 53, a second divided-display mode relates to representing a gravity center point in each of the divided regions. For this representation, in the second divided-display mode, the argument-data scatter diagram (θ, φ) is displayed on the display unit 38, as described before. Then a fixed or non-fixes ROI (region of interest): $ROI_{JK}$ is set so as to enclose the scattering points represented on the screen.

When this ROI: $ROI_{JK}$ is fixed, a known technique is used appropriately to draw a central axis JK in the largeness direction of the effective atomic numbers Zeff.

Then, in the same manner as the foregoing, as one example, lines perpendicular to the central line JK are drawn to divide the area of ROI: $ROI_{JK}$ into two or more regions. Then, for each of the divided regions, a gravity center position $G_{JK}$ of data indicative of the scattering points which are present in each divided region is calculated, the calculated position GJK is marked by a black circle symbol in each divided region and superimposed-displayed on the scattering points presented on the screen.

Third Divided-Display Mode

This third divided-display mode is provided by merging the foregoing first and second divided-display modes with each other, whereby the gravity center positions $G_{JK}$ in the respective divided regions are displayed under the color display as illustrated in FIG. 53. By this third divided-display mode, even if the scattering points in the respective divided regions are scattered in a wider area, the display of the gravity center positions $G_{JK}$ makes it easier to find out an effective atomic number Zeff which is a representative of the main compositions.

A further modification is representing the gravity center positions $G_{JK}$ on the respective divided regions each having a gradation of gray levels, in a superposed manner. In addition, in the same way as the first divided-display mode, the factors concerning the divided display, such as the number of divisions, the division lengths (variable lengths in the same scatter diagram), and/or hues of display colors, can be changed and employed in the second and third divided-display modes.

The data processor 35 then produces data indicative of scatter diagram display according to a designated divided-display mode, at step S175.

Then, at step S176, the data processor 35 reads interactively information showing a display screen mode, information about whether or not interlocking display with other images is necessary, and/or information about whether or not display enlargement or reduction is necessary. In this case, the display screen mode includes a one-monitor display mode, a two-monitor display mode, and/or a one-monitor display mode which additionally includes two divided display screens or an ordinary one-screen. The other images here are for example the foregoing absorption vector-length image or an ordinary X-ray transmission image. Then, data indicative of a display screen are produced based on the read information (step S177), and the produced data are displayed on the display unit 38 and also recorded in a memory medium (e.g., the image memory 36) (step S178). These steps are repeated until receiving a command for ending the image display process (step S179).

In this way, the present modification makes it possible to freely, but within a specified number of regions, divide the argument-data scatter diagram into a plurality of regions to display the scattering data in the various modes, every divided region. As a result, the argument-data scatter diagram can be analyzed locally with an easier manner, thereby leading to various kinds of use of the diagram, contributing to finely analyzing the substance identification.

Figure 54:
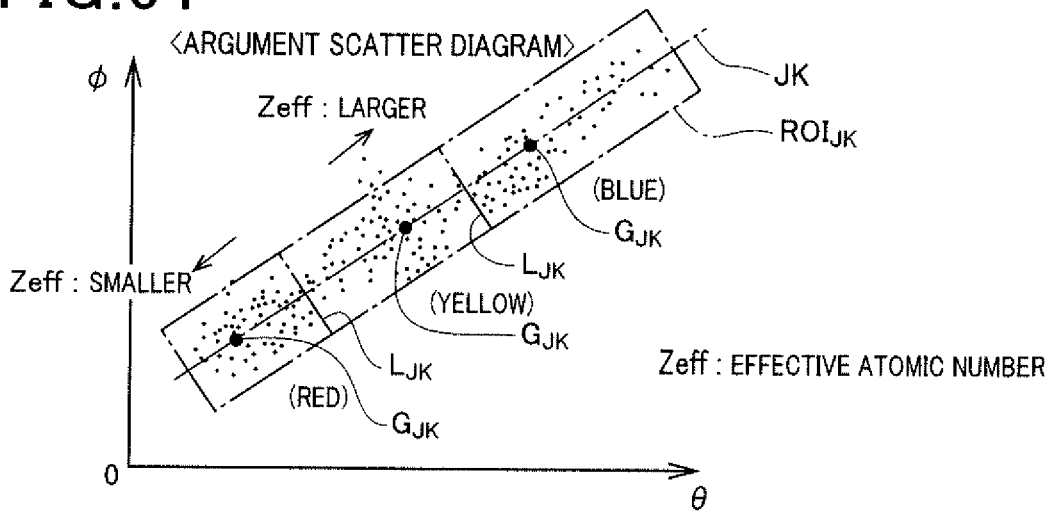
FIG. 54 a screen image exemplifying a third divided display mode according to the fifth modification.

In the foregoing argument-data scatter diagram shown in FIGS. 52 to 54, the number of divided regions is set to three, but this number may be set arbitrarily, such as an upper limit (fixed number) of ten. In addition, the argument-data scatter diagram may be subjected to a Gaussian filter process, before performing the foregoing divided-region display.

In the foregoing embodiments and modifications, the processes shown in FIGS. 6, 8, 10, 13, 21, 27, 30, 32, 38, 40 and 46 executed by the data processor 35 realizes various kinds of means (also referred to as blocks or units) provided as functional configurations. That is, the data processing apparatus 12 is able to be provided with functional or hardware configurations of count acquiring means, image data calculating means, attenuation information calculating means, inherent information producing means, scattering point calculating means, display means, coordinate converting means, data acquiring means, first display means, second display means, region-of-interest setting means, background removing means, display state instructing means, display changing means, added-information calculating means (including contour-line data calculating means), coordinate data calculating means (including difference calculating means, difference outputting means), added-information displaying means, gravity center calculating means, gravity-center positional information providing means, reference information storing means, gravity center calculating means, categorizing-line setting means, image receiving means, first specifying means, first association displaying means, second specifying means, and second association displaying means.

The data processing apparatus, data processing method and X-ray examination system according to the present invention has been described in terms of various modes. As a matter of course, the present invention will not be restricted to the foregoing examples, but can be developed into other various modes within not departing from the gist of claims.

PARTIAL REFERENCE SIGNS LIST

10 X-ray examination apparatus functioning as X-ray examination system, which is provided with data processing apparatus
12 data processing apparatus (computer system)
21 X-ray tube
24 detector
25 data acquisition circuit
26 detection unit
32 butter memory (storage means)
33 ROM
34 RAM
35 data processor (CPU)
36 image memory (storage means)
37 input unit
38 display unit

The invention claimed is:

1. A data processing apparatus characterized in that the data processing apparatus comprises:
   count acquiring means configured to acquire a count of photons of an X-ray beam, the X-ray beam being radiated from an X-ray generator and transmitted through an object, and detected by a photon counting detector, the photons being counted every pixel of the detector and every one of n-pieces (n is a positive integer of two or more) energy ranges in a spectrum of the X-ray beam or every one of energy ranges whose number is less than n;
   image data calculating means configured to calculate image data indicative of a transmission state of the X-ray beam through the object, based on the count acquired by the count acquiring means;
   attenuation information calculating means configured to calculate attenuation information indicative of how the X-ray beam is attenuated during transmission through the object, based on the image data calculated by the image data calculating means, every one of the n-piece energy ranges or every one of the energy ranges whose number is less than n and every one of the pixels or every one of pixel groups into each of which the pixels are grouped, the attenuation information including i) inherent information inherently depending on a type or a property of the object, the inherent information being indicated by a quantity of a vector in an n-dimensional coordinate whose dimension is equal in number to the n-piece energy ranges or in a coordinate whose dimension is less in number the number n; and ii) associated information being associated with the inherent information and depending on a length of a path along which the X-ray beam passes though the object;
inherent information producing means configured to produce only the inherent information which is independent of the associated information, from the attenuation information calculated by the attenuation information calculating means; and
scattering point calculating means configured to calculate scattering points to be mapped in the n-dimensional coordinate or a desired coordinate which is less in dimension than the n-dimensional coordinate, the scattering points depending on the inherent information produced by the inherent information producing means, wherein
the inherent information producing means is configured to produce, as the inherent information, information excluding a factor indicating a length component of the vector, from the information calculated by the attenuation information calculating means; and
the scattering point calculating means is configured to calculate the inherent excluding the factor indicating the length component, into scattering points mapped in the desired coordinate which is less in dimension than the n-dimensional coordinate.

2. The data processing apparatus according to claim 1, wherein the image data calculating means is configured to calculate, based on the count, image data of the object every one of the energy ranges and every one of the pixels.

3. The data processing apparatus according to claim 1, wherein
the inherent information producing means is configured to produce, as the inherent information, information showing a normalized length component of the vector from the information calculated by the attenuation information calculating means; and
the scattering point calculating means is configured to calculate the inherent information having the normalized length component, into scattering points mapped in the n-dimensional coordinate.

4. The data processing apparatus according to claim 1, wherein the scattering point calculating means is configured to calculate a scatter diagram having coordinate axes to which one or more of arguments of data in the polar coordinate are assigned, when the inherent information excluding the factor of the length component being expressed by the polar coordinate.

5. The data processing apparatus according to claim 1, comprising:
a monitor; and
display means configured to display, on the monitor, the information calculated or produced by at least one of the attenuation information calculating means, the inherent information producing means, and the scattering point calculating means.

6. The data processing apparatus according to claim 5, wherein the inherent information producing means comprises:
coordinate converting means configured to convert the attenuation information calculated by the attenuation information calculating means, to polar coordinate data expressed in a polar coordinate; and
data acquiring means configured to acquire, as the inherent information, a scatter diagram having coordinate axes to which one or more arguments of the polar coordinate data are assigned, from the polar coordinate data converted by the coordinate converting means.

7. The data processing apparatus according to claim 1, wherein the n-dimension is a three dimension, and the dimension whose dimensional numbers are lower than the n-dimension is a two dimension.

8. The data processing apparatus according to claim 1, comprising vector length calculating means configured to calculate, as the associated information, information of a vector length indicating a magnitude of the vector and an attenuated degree of the X-ray beam transmitted through the object at each of the pixels.

9. The data processing apparatus according to claim 1, comprising
added-information calculating means configured to calculate the added information based on information showing the one or more arguments composing the scatter diagram calculated by the scatter point calculating means; and
coordinate data calculating means configured to calculate data indicating a coordinate system in which the added information calculated by the added-information calculating means is added to the scatter diagram, the coordinate system having dimensions larger, by one, than dimensions of the scatter diagram.

10. The data processing apparatus according to claim 9, comprising added-information displaying means configured to enable the monitor to the data indicating the coordinate system calculated by the coordinate data calculating means.

11. The data processing apparatus according to claim 9, wherein
the information indicating the one or more arguments consists of information indicating two arguments;
the added-information calculating means comprises scattering-point number calculating means configured to calculate the number of scattering points per a predetermined area in a two-dimensional coordinate, based on the scatter diagram in the two-dimensional coordinate to which the information indicating the two arguments is assigned to respective coordinate axes thereof.

12. The data processing apparatus according to claim 11, wherein the added-information displaying means is configured to display the added information as data provided in a three-dimensional coordinate created by adding a third axis functioning as a one dimension to the two-dimensional coordinate.

13. The data processing apparatus according to claim 12, wherein
the added-information calculating means comprises contour-line data calculating means configured to calculate contour-line data indicating that values assigned to the third axis show height information; and
the added-information displaying means is configured to display both lines showing the contour-line data and data showing the three-dimensional coordinate.

14. The data processing apparatus according to claim 12, wherein the coordinate data calculating means comprises
difference calculating means configured to calculate a difference between the data of the coordinate systems obtained by acquiring the counts respectively in two or more times of X-ray imaging operations; and
difference outputting means configured to calculate and output data of the coordinate systems depending on the calculated difference.

15. The data processing apparatus according to claim 12, comprising:
gravity center calculating means configured to detect a collection of the scattering points and calculate a position of a gravity center of the collection, based on scattered conditions of the scattering points, calculated by the scattering point calculating means; and gravity-center positional information providing means configured to provide information indicative of a position of the gravity center of the collection of the scattering points.

16. The data processing apparatus according to claim 15, comprising identification means configured to identify a foreign matter contained in or attached on the object or an abnormal state of the object, based on a difference occurring about the position of the gravity center in the coordinate.

17. The data processing apparatus according to claim 16, comprising reference information storing means configured to have reference information in advance, the reference information indicating positional information of the gravity center of a reference object in the coordinate, the reference object having no foreign matter included or attached or being in a normal state, wherein the identification means is configured to identify the foreign matter by comparing, with the reference information, the positional information of the gravity center in the coordinate acquired by actually imaging the object.

18. The data processing apparatus according to claim 1, wherein the one or more arguments consist of two arguments;

the data acquiring means is configured to acquire a two-dimensional scatter diagram having two coordinate axes to which two arguments of the polar coordinate are assigned, data indicating the polar coordinate being converted by the coordinate converting means, the two-dimensional scatter diagram having no directional dependency; and the processing apparatus comprises:

gravity center calculating means configured to detect a collection of the scattering points and calculate a position of a gravity center of the collection in the two-dimensional scatter diagram, based on scattered conditions of the scattering points, calculated by the scatter diagram calculating means; and categorizing-line setting means configured to set a categorizing line based on the position of the gravity center in the collection of the scattering points, calculated by the gravity center calculating means, the categorizing line drawing a border between distributions of the scattering points in the two-dimensional scatter diagram, the scattering points being obtained from a plurality of types of substances which are present inside or outside the object.

19. The data processing apparatus according to claim 1, wherein the one or more arguments consist of two arguments;

the data acquiring means is configured to acquire a two-dimensional scatter diagram having two coordinate axes to which two arguments of the polar coordinate are assigned, data indicating the polar coordinate being converted by the coordinate converting means, the two-dimensional scatter diagram having no directional dependency; and the processing apparatus comprises:

image receiving means configured to receive, as the object, a mammography image of a human body;

first specifying means configured to specify scatter diagram data corresponding to the two-dimensional scatter diagram in accordance with a designated region on the mammography image;

first interlocking displaying means configured to enable the monitor to interlocking-display the two-dimensional scatter diagram with a distinguished portion, responsively to the scatter diagram data specified by the specifying means;

second specifying means configured to specify pixels of the mammography, which have pixel values corresponding to a designated region on the two-dimensional scatter diagram; and second interlocking displaying means configured to enable the monitor to interlocking-display the mammography image with a distinguished portion having the specified pixels, specified by the second specifying means.

20. An X-ray examination system comprising:

a data processing apparatus comprising:

count acquiring means configured to acquire a count of photons of an X-ray beam, the X-ray beam being radiated from an X-ray generator and transmitted through an object, and detected by a photon counting detector, the photons being counted every pixel of the detector and every one of n-pieces (n is a positive integer of two or more) energy ranges in a spectrum of the X-ray beam or every one of energy ranges whose number is less than n;

image data calculating means configured to calculate image data indicative of a transmission state of the X-ray beam through the object, based on the count acquired by the count acquiring means;

attenuation information calculating means configured to calculate attenuation information indicative of how the X-ray beam is attenuated during transmission through the object, based on the image data calculated by the image data calculating means, every one of the n-piece energy ranges or every one of the energy ranges whose number is less than n and every one of the pixels or every one of pixel groups into each of which the pixels are grouped, the attenuation information including i) inherent information inherently depending on a type or a property of the object, the inherent information being indicated by a quantity of a vector in an n-dimensional coordinate whose dimension is equal in number to the n-piece energy ranges or in a coordinate whose dimension is less in number the number n; and ii) associated information being associated with the inherent information and depending on a length of a path along which the X-ray beam passes though the object;

inherent information producing means configured to produce only the inherent information which is independent of the associated information, from the attenuation information calculated by the attenuation information calculating means; and scattering point calculating means configured to calculate scattering points to be mapped in the n-dimensional coordinate or a desired coordinate which is less in dimension than the n-dimensional coordinate, the scattering points depending on the inherent information produced by the inherent information producing means, and analysis means configured to analyze at least one of a type or a property of the object based on data indicative of the scattering points calculated by the scattering point calculating means, wherein the inherent information producing means is configured to produce, as the inherent information, information excluding a factor indicating a length component of the vector, from the information calculated by the attenuation information calculating means; and the scattering point calculating means is configured to calculate the inherent excluding the factor indicating the length component, into scattering points mapped in the desired coordinate which is less in dimension than the n-dimensional coordinate.

21. A data processing method characterized in that the data processing method comprises:

acquiring a count of photons of an X-ray beam, the X-ray beam being radiated from an X-ray generator and transmitted through an object, and detected by a photon counting detector, the photons being counted every pixel of the detector and every one of n-pieces (n is a positive integer of two or more) energy ranges in a spectrum of the X-ray beam or every one of energy ranges whose number is less than n;

calculating image data indicative of a transmission state of the X-ray beam through the object, based on the acquired count;

calculating attenuation information indicative of how the X-ray beam is attenuated during transmission through the object, based on the calculated image data, every one of the n-piece energy ranges or every one of the energy ranges whose number is less than n and every one of the pixels or every one of pixel groups into each of which the pixels are grouped, the attenuation information including i) inherent information inherently depending on a type or a property of the object, the inherent information being indicated by a quantity of a vector in an n-dimensional coordinate whose dimension is equal in number to the n-piece energy ranges ranges or in a coordinate whose dimension is less in number the number n; and ii) associated information being associated with the inherent information and depending on a length of a path along which the X-ray beam passes though the object; and producing only the inherent information which is independent of the associated information, from the calculated attenuation information, and calculating scattering points to be mapped in the n-dimensional coordinate or a desired coordinate which is less in dimension than the n-dimensional coordinate, the scattering points depending on the produced inherent information, wherein the inherent information producing step produces, as the inherent information, information excluding a factor indicating a length component of the vector, from the calculated information calculated in the attenuation information calculating step; and the scattering point calculating step calculates the inherent excluding the factor indicating the length component, into scattering points mapped in the desired coordinate which is less in dimension than the n-dimensional coordinate.

* * * * *